(12) United States Patent
Menon et al.

(10) Patent No.: US 11,083,915 B2
(45) Date of Patent: *Aug. 10, 2021

(54) ANTIPERSPIRANT SPRAY DEVICES AND COMPOSITIONS

(71) Applicant: The Procter & Gamble Company, Cincinnati, OH (US)

(72) Inventors: Elton Luis Menon, Mason, OH (US); David Frederick Swaile, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/307,447

(22) Filed: Jun. 17, 2014

(65) Prior Publication Data

US 2015/0023885 A1    Jan. 22, 2015

Related U.S. Application Data

(60) Provisional application No. 61/846,951, filed on Jul. 16, 2013.

(51) Int. Cl.
| | |
|---|---|
| *A61Q 15/00* | (2006.01) |
| *A61K 8/04* | (2006.01) |
| *B65D 83/48* | (2006.01) |
| *A61K 8/37* | (2006.01) |
| *A61K 8/891* | (2006.01) |
| *A61K 8/02* | (2006.01) |
| *B05B 7/04* | (2006.01) |
| *A61K 8/26* | (2006.01) |
| *B65D 83/14* | (2006.01) |
| *A61K 8/42* | (2006.01) |
| *B05B 15/50* | (2018.01) |
| *B65D 83/46* | (2006.01) |
| *B65D 83/54* | (2006.01) |

(52) U.S. Cl.
CPC ............ *A61Q 15/00* (2013.01); *A61K 8/0241* (2013.01); *A61K 8/046* (2013.01); *A61K 8/26* (2013.01); *A61K 8/37* (2013.01); *A61K 8/891* (2013.01); *B05B 7/0483* (2013.01); *B65D 83/48* (2013.01); *B65D 83/752* (2013.01); *A61K 8/42* (2013.01); *A61K 2800/59* (2013.01); *A61K 2800/87* (2013.01); *B05B 15/50* (2018.02)

(58) Field of Classification Search
None
See application file for complete search history.

(56) References Cited

U.S. PATENT DOCUMENTS

| | | | |
|---|---|---|---|
| 868,791 A | 10/1907 | Macgregor | |
| 4,110,428 A | 8/1978 | Kuhn et al. | |
| 4,152,416 A | 5/1979 | Spitzer et al. | |
| 4,278,655 A | 7/1981 | Elmi | |
| 4,396,152 A | 8/1983 | Abplanalp | |
| 4,411,883 A | 10/1983 | Kenkare | |
| 4,806,338 A | 2/1989 | Smith | |
| 4,840,786 A | 6/1989 | Johnson et al. | |
| 4,889,711 A | 12/1989 | Kai et al. | |
| 4,904,463 A | 2/1990 | Johnson et al. | |
| 4,935,224 A | 6/1990 | Russo et al. | |
| 5,082,652 A | 1/1992 | Mayfield et al. | |
| 5,156,834 A * | 10/1992 | Beckmeyer | ............ A61K 8/585 424/47 |
| 5,294,447 A | 3/1994 | Mackles et al. | |
| 5,298,236 A * | 3/1994 | Orr | .......................... A61K 8/28 424/47 |
| 5,444,096 A | 8/1995 | McCrea et al. | |
| 5,605,682 A | 2/1997 | Ross et al. | |
| 5,806,338 A | 9/1998 | Schwartz et al. | |
| 5,814,309 A | 9/1998 | Panitch | |
| 5,840,289 A | 11/1998 | Hall | |
| 5,961,963 A * | 10/1999 | Temple | .................. A61K 8/046 424/400 |
| 6,136,303 A | 10/2000 | Ruebusch et al. | |

(Continued)

FOREIGN PATENT DOCUMENTS

| | | |
|---|---|---|
| DE | 2118368 A1 | 10/1971 |
| DE | 2741819 A1 | 3/1978 |

(Continued)

OTHER PUBLICATIONS

Derek L. Ho et al., Effects of Solvent Solubility Parameters on Organoclay Dispersions, Chem. Mater., vol. 15, No. 6, 2003, pp. 1309-1312.
U.S. Appl. No. 14/307,433, filed Jun. 18, 2014, Elton Luis Menon et al.
U.S. Appl. No. 14/307,438, filed Jun. 18, 2014, Elton Luis Menon et al.

(Continued)

*Primary Examiner* — John Pak
*Assistant Examiner* — Daniel L Branson
(74) *Attorney, Agent, or Firm* — Kathleen Y. Carter

(57) ABSTRACT

A hand held spray device is disclosed. The spray device has a body with a reservoir to house a total fill of material, an actuator having an actuator exit orifice, a valve in fluid communication with the actuator exit orifice and the reservoir, and a propellant and antiperspirant composition stored in the reservoir. The propellant has a concentration from 30% to 70% by weight of the total fill of materials stored within the reservoir. The antiperspirant composition includes a non-volatile silicone fluid having a concentration from about 30% to about 70% by weight of the antiperspirant composition, an antiperspirant active, an organoclay material and at least one liquid activation enhancer, and optionally a liquid fragrance material.

32 Claims, 27 Drawing Sheets

(56) References Cited

U.S. PATENT DOCUMENTS

| | | | |
|---|---|---|---|
| 6,726,901 B2 | 4/2004 | Yin et al. | |
| 7,569,170 B2 | 8/2009 | Minor | |
| 7,597,818 B2 | 10/2009 | Singh | |
| 7,815,899 B2 | 10/2010 | Smith | |
| 7,951,358 B2 | 5/2011 | Smith | |
| 8,008,244 B2 | 8/2011 | Knopeck et al. | |
| 8,075,796 B2 | 12/2011 | Rao et al. | |
| 8,097,181 B2 | 1/2012 | Leck | |
| 8,101,094 B2 | 1/2012 | Howell et al. | |
| 8,114,828 B2 | 2/2012 | Bowman et al. | |
| 8,133,407 B2 | 3/2012 | Zyhowski et al. | |
| 8,147,709 B2 | 4/2012 | Mahler et al. | |
| 8,333,902 B2 | 12/2012 | Mahler et al. | |
| 8,388,857 B2 | 3/2013 | Elsheikh et al. | |
| 8,393,554 B2 | 3/2013 | Yamamoto et al. | |
| 8,394,286 B2 | 3/2013 | Leck et al. | |
| 8,399,713 B2 | 3/2013 | Bartelt et al. | |
| 8,496,846 B2 | 7/2013 | Rao et al. | |
| 8,518,384 B2 | 8/2013 | Fletcher et al. | |
| 8,529,786 B2 | 9/2013 | Leck et al. | |
| 8,535,555 B2 | 9/2013 | Howell et al. | |
| 8,628,681 B2 | 1/2014 | Low | |
| 8,637,443 B2 | 1/2014 | Basu et al. | |
| 8,691,107 B2 | 4/2014 | Elsheikh et al. | |
| 8,692,037 B2 | 4/2014 | Mahler et al. | |
| 8,747,691 B2 | 6/2014 | Hulse et al. | |
| 8,815,114 B2 | 8/2014 | Rao et al. | |
| 10,076,474 B2 | 9/2018 | Swaile et al. | |
| 2005/0169850 A1 | 8/2005 | Smith | |
| 2006/0104918 A1* | 5/2006 | Brown | A61K 8/046 424/47 |
| 2006/0134037 A1 | 6/2006 | Cropper et al. | |
| 2006/0210502 A1 | 9/2006 | Galante et al. | |
| 2006/0269484 A1 | 11/2006 | Knopeck et al. | |
| 2007/0098646 A1 | 5/2007 | Nappa et al. | |
| 2007/0292460 A1 | 12/2007 | Schiemann et al. | |
| 2008/0157022 A1 | 7/2008 | Singh et al. | |
| 2008/0292564 A1 | 11/2008 | Singh et al. | |
| 2010/0122545 A1 | 5/2010 | Minor et al. | |
| 2010/0200799 A1 | 8/2010 | Mouli | |
| 2011/0031436 A1 | 2/2011 | Mahler et al. | |
| 2011/0232939 A1 | 9/2011 | Luly et al. | |
| 2011/0253927 A1 | 10/2011 | Minor et al. | |
| 2011/0257282 A1 | 10/2011 | Alexander | |
| 2012/0003284 A1* | 1/2012 | Arnaud | A61K 8/0229 424/401 |
| 2012/0126187 A1 | 5/2012 | Low | |
| 2012/0168663 A1 | 7/2012 | Singh | |
| 2012/0305480 A1 | 12/2012 | Low | |
| 2013/0032751 A1 | 2/2013 | Low | |
| 2013/0187078 A1 | 7/2013 | Low | |
| 2013/0193368 A1 | 8/2013 | Low | |
| 2013/0295024 A1* | 11/2013 | Hammer | A61Q 19/00 424/45 |
| 2013/0305830 A1 | 11/2013 | Takahashi et al. | |
| 2014/0026056 A1 | 3/2014 | Swaile et al. | |
| 2014/0077003 A1 | 3/2014 | Swaile et al. | |
| 2014/0079649 A1 | 3/2014 | Swaile et al. | |
| 2014/0193470 A1 | 7/2014 | Arnaud et al. | |
| 2014/0348756 A1 | 11/2014 | Doering et al. | |
| 2015/0023887 A1 | 1/2015 | Swaile et al. | |
| 2015/0283044 A1 | 10/2015 | Swaile et al. | |
| 2015/0283046 A1 | 10/2015 | Swaile et al. | |

FOREIGN PATENT DOCUMENTS

| | | |
|---|---|---|
| DE | 102009027050 A1 | 12/2010 |
| DE | 102009055255 A1 | 6/2011 |
| DE | 102011066019 A1 | 8/2012 |
| EP | 0028853 A2 | 5/1981 |
| EP | 0485012 A1 | 5/1992 |
| EP | 0 684 038 A2 | 11/1995 |
| EP | 0 674 899 B1 | 8/2001 |
| EP | 1803660 A1 | 7/2007 |
| EP | 2574327 A1 | 4/2013 |
| FR | 2978032 A1 | 1/2013 |
| GB | 1341618 A | 12/1973 |
| GB | 1476117 A | 6/1977 |
| GB | 2296189 A | 6/1996 |
| GB | 2 299 507 A | 10/1996 |
| GB | 2456028 A | 7/2009 |
| GB | 2477865 A | 8/2011 |
| JP | 2009-102271 A | 5/2009 |
| JP | 2011-126862 A | 6/2011 |
| JP | 2011184585 A | 9/2011 |
| WO | 96/04884 A1 | 2/1996 |
| WO | 9711678 A1 | 4/1997 |
| WO | 2004/014330 A1 | 2/2004 |
| WO | 2005103192 A1 | 11/2005 |
| WO | 2006101882 A2 | 9/2006 |
| WO | 2007/000184 A1 | 1/2007 |
| WO | 2008009922 A2 | 1/2008 |
| WO | 2008/025524 A2 | 3/2008 |
| WO | 2008027512 A2 | 3/2008 |
| WO | 2008027513 A2 | 3/2008 |
| WO | 2008027516 A1 | 3/2008 |
| WO | 2008027595 A1 | 3/2008 |
| WO | 2008027596 A2 | 3/2008 |
| WO | 2010035701 A1 | 4/2010 |
| WO | 2012085055 A2 | 6/2012 |
| WO | 2013013999 A2 | 1/2013 |
| WO | 2013079349 A1 | 6/2013 |
| WO | 2013098141 A2 | 7/2013 |
| WO | 2013111912 A1 | 8/2013 |
| WO | 2014043487 A2 | 3/2014 |

OTHER PUBLICATIONS

U.S. Appl. No. 14/307,455, filed Jun. 17, 2014, Elton Luis Menon et al.
U.S. Appl. No. 14/307,457, filed Jun. 18, 2014, Elton Luis Menon et al.
U.S. Appl. No. 14/307,462, filed Jun. 17, 2014, Elton Luis Menon et al.
U.S. Appl. No. 14/307,466, filed Jun. 17, 2014, David Frederick Swaile et al.
All Office Actions, U.S. Appl. No. 14/307,457.
All Office Actions, U.S. Appl. No. 14/307,433.
All Office Actions, U.S. Appl. No. 14/307,438.
All Office Actions, U.S. Appl. No. 14/307,455.
All Office Actions, U.S. Appl. No. 14/307,462.
All Office Actions, U.S. Appl. No. 14/307,466.
All Office Actions, U.S. Appl. No. 14/656,118.
All Office Actions, U.S. Appl. No. 14/656,144.
All Office Actions, U.S. Appl. No. 15/404,692.
International Search Report and Written Opinion of the International Searching Authority, PCT/US2014/046577, dated Dec. 3, 2014, 17 pages.
A comparison of smectite clays in underarm products, Elementis-Specialties published on 2008, p. 16.
Bentone Gel® IPM V Data Sheet published on 1999, 4 Pages.
Bentone Gel® IPM V, Questions & Answers published on 2008, 15 Pages.
Database GNPD [Online] Mintel, "Anti-White Marks Anti-PerspirantDeodorant", Feb. 2013, 3 Pages, XP00273029.
Excerpt from "Handbook on Cosmetics" by S.K. Singh, 2010, 4 Pages.
Excerpt from the INCI Dictionary, 13th Edition, vol. 3, 2010, 2 Pages.
Experimental Data Report EP3021821, Jan. 22, 2019, pp. 1-8.
Experimental Data Report EP3021824B1, Aug. 2, 2019, pp. 1-8.
Experimental Report EP3021825, 3 Pages.
Extract for Ethylene Brassylate from the International CosmeticIngredient Dictionary and Handbook published on 2010, pp. 1-6.
Garnier Mineral Ultra Dry (Deodorant Spray), Mintel DatabaseZugangsnummer (Record ID): 1288406, 1 Page.
International Cosmetic Ingredient Dictionary and Handbook, 13thEd., vol. 1, 2010, 5 Pages.
International Search Report and Written Opinion; Application Serial No. PCT/US2014/046576, dated Nov. 20, 2014, 20 pages.

(56) References Cited

OTHER PUBLICATIONS

International Search Report and Written Opinion; Application Serial No. PCT/US2014/046577, dated Dec. 3, 2014, 31 pages.
International Search Report and Written Opinion; Application Serial No. PCT/US2014/046578, dated Nov. 24, 2014, 14 pages.
Perfumer's Apprentice, Carriers and Diluting Oils, extracted from https://shop.perfumetsapprentice.com/c-63-ci.mier-and-diluting.,oils.aspx, 5 Pages.
Photo of calcium chloride in silicone oil.
Poucher's—Perfumes, Cosmetics and Soaps, 10th Edition, 2000, 1 Page.
Product specifications of Sigma Aldrich for Ethylene Brassylate, 1 Page.
Sigma-Aldrich, Product Specification, W308307.
Supplementary experimental report EP3021821, Oct. 2, 2019, 5 Pages.
Xiameter PMX-1501 Fluid, 1 Page, XP055385527.

\* cited by examiner

ANTIPERSPIRANT SPRAY DEVICES AND COMPOSITIONS

TECHNICAL FIELD

One aspect of the invention relates generally to spray devices containing an antiperspirant composition and a propellant. Yet another aspect of the invention relates generally to methods of using antiperspirant spray devices.

BACKGROUND OF THE INVENTION

Spray devices are generally well known in the art, some examples of which are disclosed in U.S. Pat. Nos. 4,396,152 and 5,082,652. Aerosol spray devices that dispense an antiperspirant composition are also known in the art. Various examples are described in U.S. Pat. Nos. 4,152,415; 4,806,338; 4,840,786; 4,904,463; 4,935,224; 5,298,236; 5,605,682; 5,814,309; 7,815,899; EP 674,899; and WO 96/04884; WO/2004/014330; WO 2007/00184, commonly assigned U.S. Ser. No. 61/701,201 filed Sep. 14, 2012 and U.S. Ser. No. 61/789,480 filed Mar. 15, 2013, the substances of which are incorporated herein by reference.

Many aerosol antiperspirant users desire a product that provides one or more of the following benefits: minimizes the appearance of residue on the skin, has a dry rather than wet feel, has rapid perceived drying, is not sticky, provides a cool/fresh feeling at time of application, provides long lasting wetness and/or odor protection, is provided in a form that is easily portable in purses or small bags (as some users may apply the antiperspirant composition more than once a day) and minimizes the gassy cloud that forms during dispensing. While the relative importance/desirability of these characteristics may vary by geographical region and gender and not all users desire all or the same set of characteristics, there appears to be a generally universal desire among aerosol antiperspirant users for a dry rather than wet feel, minimizing the appearance of residue, and providing long lasting wetness/odor protection or efficacy.

While some currently marketed aerosol spray devices may provide at least some of these benefits to varying degrees, there are often a series of tradeoffs involved depending on the combination of ingredients used.

Significant settling and/or agglomeration of particulates in an antiperspirant composition may complicate delivery of a uniform dose of the antiperspirant active from an aerosol spray device.

It may thus be desirable, in some instances, for these antiperspirant compositions to contain a clay material as a bulking or suspending agent in order to reduce settling/caking of particulates, particularly the antiperspirant active, and to aid redispersion of the particulates by shaking of the package prior to use.

The use of bulking and suspending agents, such as smectite clays and silicas, in antiperspirant compositions is well known (see, e.g., A Comparison of Smectite Clays in Underarm Products, Elementis Specialites brochure © 2008 and U.S. Pat. Nos. 5,298,236; 4,935,224; 4,904,463; 4,806,338; 4,152,416; and WO 96/04884). Smectite clays are typically layered minerals that comprise closely agglomerated individual platelets (see, e.g., Additives Reference Guide, Claytone® and Tixogel® Organoclays, Southern Clay Products brochure). In some instances, the smectite clays used in antiperspirant compositions are organoclays, which are clays that have been modified by the addition of organic moieties (e.g., alkyl quaternary materials such as dimethyl distearyl ammonium chloride) to a portion of the platelet faces. The platelets are typically separated in a shearing operation and then chemically activated (e.g., by the addition of triethyl citrate, propylene carbonate, etc.). The chemical activator facilitates the formation of hydrogen bonds between the edges of adjacent platelets (see, e.g., Rheological Additives in Cosmetics, Elementis Specialties brochure), thereby creating a network with a much larger volume than the original raw material. This network may act as a bulking or suspending matrix that may reduce the settling and/or caking of particulates in the composition and aid redispersion of the particulates upon shaking of the spray device. This may be particularly useful in an antiperspirant composition, as the aluminum salts are dense and tend to settle quickly and/or may be prone to caking in the presence of moisture. Significant settling and/or agglomeration of particulates in an antiperspirant composition may complicate delivery of a uniform dose of the antiperspirant active from an aerosol spray device. This may in turn negatively impact skin feel or contribute to the appearance of a white residue. Further, poor activation of the clay material may reduce flow of the antiperspirant composition into a dip tube and/or agglomerates may enter the dip tube and clog small orifices within the valve.

The use of liquid fragrance is also desirable in antiperspirant compositions. While there are benefits to including a liquid fragrance material in an antiperspirant composition, it is believed that at least some liquid fragrance materials may negatively affect activation of a clay material. This may become more apparent as the liquid fragrance material concentration increases.

Many currently available aerosol antiperspirant compositions also incorporate a volatile liquid (e.g., cyclopentasiloxane) as a carrier for the antiperspirant active. The volatile liquid evaporates following application to the skin, resulting in a dry skin feel, but sometimes leaves behind a visible residue (the antiperspirant active) that is subject to flaking and/or transfer to clothing. Flaking (or transfer) of the antiperspirant active may also reduce antiperspirant efficacy. It may be possible to overcome this visible residue problem with the use of non-volatile silicones which may increase the substantivity of the antiperspirant composition and actives on the skin as well as decrease the propensity for forming visible residue on skin. However, avoiding a perception of wetness post application, which is sometimes associated with the inclusion of non-volative silicones, must also be minimized.

Also in some instances it may be desirable to use different ranges of propellant concentrations. One the one hand some consumers like current antiperspirant aerosol spray devices that are typically large (greater than 150 ml). These devices accommodate high propellant concentrations and may contain a larger amount of antiperspirant composition. On the other hand some consumers like to use smaller spray devices that may be carried in small purses and the like. Like antiperspirant composition components, there are additional product tradeoffs involved with the selection of different propellant levels. For example, high propellant concentrations (e.g., greater than 75% and often greater than 80%), may dilute the antiperspirant composition, which in turn may help reduce the risk of clogging by particulates in the antiperspirant composition (e.g., the antiperspirant active, silica, clays etc.). Higher propellant concentration enhances the cool/fresh feeling at time of application due to more liquid propellant depositing on the skin and subsequently vaporizing there from. However, a high propellant concentration also produces a large volume of gas upon exiting the spray device resulting in a gassy cloud and/or a turbulent spray. Deposition efficiency (e.g., the amount of antiperspirant active and/or fragrance deposited on skin compared to the amount dispensed) may in turn be reduced due to the large amount of antiperspirant active and/or fragrance lost to the environment via the gassy cloud rather than deposited on the skin. A high propellant concentration may also result in solubilization of liquid fragrance materials into the propellant during storage, resulting in more of the liquid fragrance material being lost to the environment with the propellant rather than deposited on the skin. These disadvantages may be minimized depending on the selected propellant levels.

It is believed that antiperspirant compositions comprising a non-volatile silicone fluid, a clay material, a liquid activation enhancer and optionally a clay activator and/or a liquid fragrance material, in combination with a range of propellant concentrations for use in a spray device, may be useful for addressing one or more of the above-described tradeoffs. These compositions may provide enhanced dispersion and uniform dosing of actives, minimize interactions between the liquid fragrance and the clay, and decrease visible residue problems via use of non volatile silicones, etc.

Therefore, there is a continuing desire to provide an antiperspirant composition comprising a non-volatile silicone fluid, a clay material, a liquid activation enhancer, and optionally a liquid fragrance material and/or a clay activator, for use in a spray device having a propellant concentration. Still further, there is a continuing desire to provide an antiperspirant composition comprising a non-volatile silicone fluid, a clay material, a liquid activation enhancer, and optionally a liquid fragrance material and/or clay activator, for use in a spray device having a propellant concentration less than about 70%. Still further yet, there is a continuing desire to provide improved making and filling methods for an antiperspirant composition comprising a non-volatile silicone fluid, a clay material, and optionally a liquid activation enhancer, a liquid fragrance material, and/or a clay activator. Various non-limiting antiperspirant compositions and spray devices and methods are described hereafter which may be suitable for addressing one or more of these desires.

SUMMARY OF THE DISCLOSURE

In one aspect, a hand held spray device is disclosed, comprising: a body comprising a reservoir to house a total fill of material; an actuator comprising an actuator exit orifice; a valve in fluid communication with the actuator exit orifice and the reservoir; a propellant stored in the reservoir, the propellant having a concentration from 30% to 70% by weight of the total fill of materials stored within the reservoir; an antiperspirant composition stored in the reservoir, the antiperspirant composition comprising a non-volatile silicone fluid having a concentration from about 30% to about 70% by weight of the antiperspirant composition, an antiperspirant active, an organoclay material and at least one liquid activation enhancer having a Hansen Solubility Parameter for Hydrogen Bonding, $\delta_h$, between about 2 and about 6 and a light transmittance value greater than 90%, and optionally a liquid fragrance material.

In another aspect a hand held spray device is disclosed, comprising: a body comprising a reservoir to house a total fill of materials; an actuator comprising an actuator exit orifice; a valve in fluid communication with the actuator exit orifice and the reservoir; a propellant stored in the reservoir, the propellant having a concentration from 30% to 70% by weight of the total fill of materials stored within the reservoir; and an antiperspirant composition stored in the reservoir, the antiperspirant composition comprising a non-volatile silicone fluid having a concentration from about 30% to 70% by weight of the antiperspirant composition, an antiperspirant active, an organoclay material and at least one liquid activation enhancer having the following formula (I):

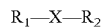

wherein $R_1$ contains from about 8 to about 20 carbon atoms, X is selected from the group consisting of an alcohol, ester, amide and aryl group, and $R_2$ is selected from the group consisting of null, H, 1 to 4 carbon atoms, and $C_6H_5$.

In another aspect a hand held spray device is disclosed, comprising: a body comprising a reservoir to house a total fill of material; an actuator comprising an actuator exit orifice;

a valve in fluid communication with the actuator exit orifice and the reservoir; a propellant stored in the reservoir, the propellant having a concentration from 72% to 90% by weight of the total fill of materials stored within the reservoir; an antiperspirant composition stored in the reservoir, the antiperspirant composition comprising a non-volatile silicone fluid having a concentration from about 30% to about 70% by weight of the antiperspirant composition, an antiperspirant active, greater than 1% substantially inert particulates, an organoclay material and at least one liquid activation enhancer having a Hansen Solubility Parameter for Hydrogen Bonding, $\delta_h$, between about 2 and about 6 and a light transmittance value greater than 90%, and optionally a liquid fragrance material.

In another aspect a hand held spray device is disclosed, comprising: a body comprising a reservoir to house a total fill of materials; an actuator comprising an actuator exit orifice; a valve in fluid communication with the actuator exit orifice and the reservoir; a propellant stored in the reservoir, the propellant having a concentration from 72% to 90% by weight of the total fill of materials stored within the reservoir; and an antiperspirant composition stored in the reservoir, the antiperspirant composition comprising a non-volatile silicone fluid having a concentration from about 30% to about 70% by weight of the antiperspirant composition, an antiperspirant active, greater than 1% substantially inert particulates, an organoclay material and at least one liquid activation enhancer having the following formula (I):

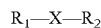

wherein $R_1$ contains from about 8 to about 20 carbon atoms, X is selected from the group consisting of an alcohol, ester, amide and aryl group, and $R_2$ is selected from the group consisting of null, H, 1 to 4 carbon atoms, and $C_6H_5$.

In another embodiment a method for filling a hand held spray device is disclosed, comprising: providing a body with a reservoir having a total fill of materials;

mixing a non-volatile silicone fluid, an antiperspirant active, at least one liquid activation enhancer and a first portion of an organoclay material to form a first composition, wherein the liquid activation enhancer has a Hansen Solubility Parameter for Hydrogen Bonding, $\delta_h$, between about 2 and about 6 and a light transmittance value greater than 90%; mixing a liquid fragrance material and a second portion of an organoclay material to form a second composition; filling the reservoir by either mixing the first composition and the second composition to form an antiperspirant composition or by filling the reservoir with the first composition and thereafter filling the reservoir with the second composition after the reservoir is filled with the first composition, to form an antiperspirant composition; providing a valve and attaching the valve to the body; and filling the reservoir with a propellant having a concentration of from about 30% to about 90% by weight of the total fill of materials.

In another embodiment a method of filling a hand held spray device is disclosed, comprising: providing a body having a reservoir comprising a total fill of materials; filling the reservoir with a first composition comprising a non-volatile silicone fluid, an antiperspirant active, an organo-clay material, and at least one liquid activation enhancer having a Hansen Solubility Parameter for Hydrogen Bonding, $\delta_h$, between about 2 and about 6 and a light transmittance value greater than 90%; filling the reservoir with a second composition comprising a liquid fragrance material after the reservoir is filled with the first composition to form an antiperspirant composition, wherein the non-volatile silicone fluid has a concentration from about 30% to about 70% by weight of the antiperspirant composition; providing a valve and attaching the valve to the body; and filling the reservoir with a propellant, wherein the hand held spray device has a propellant concentration after filling from about 30% to about 90% by weight of the total fill of materials within the reservoir.

In another embodiment a hand held spray device is disclosed, comprising: a body comprising a reservoir comprising a total fill of materials including a propellant and an antiperspirant composition; an actuator comprising an actuator exit orifice; a valve in fluid communication with the actuator exit orifice and the reservoir; the propellant having a concentration from about 30% to about 70% by weight of the total fill of materials and a boiling point at 1 atmosphere from about −10° C. to about 10° C.; and the antiperspirant composition comprising a liquid carrier and an antiperspirant active.

BRIEF DESCRIPTION OF THE DRAWINGS

While the specification concludes with claims, it is believed that the same will be better understood from the following description taken in conjunction with the accompanying drawings wherein like numbers illustrate like elements throughout the views and in which:

Figure 1:
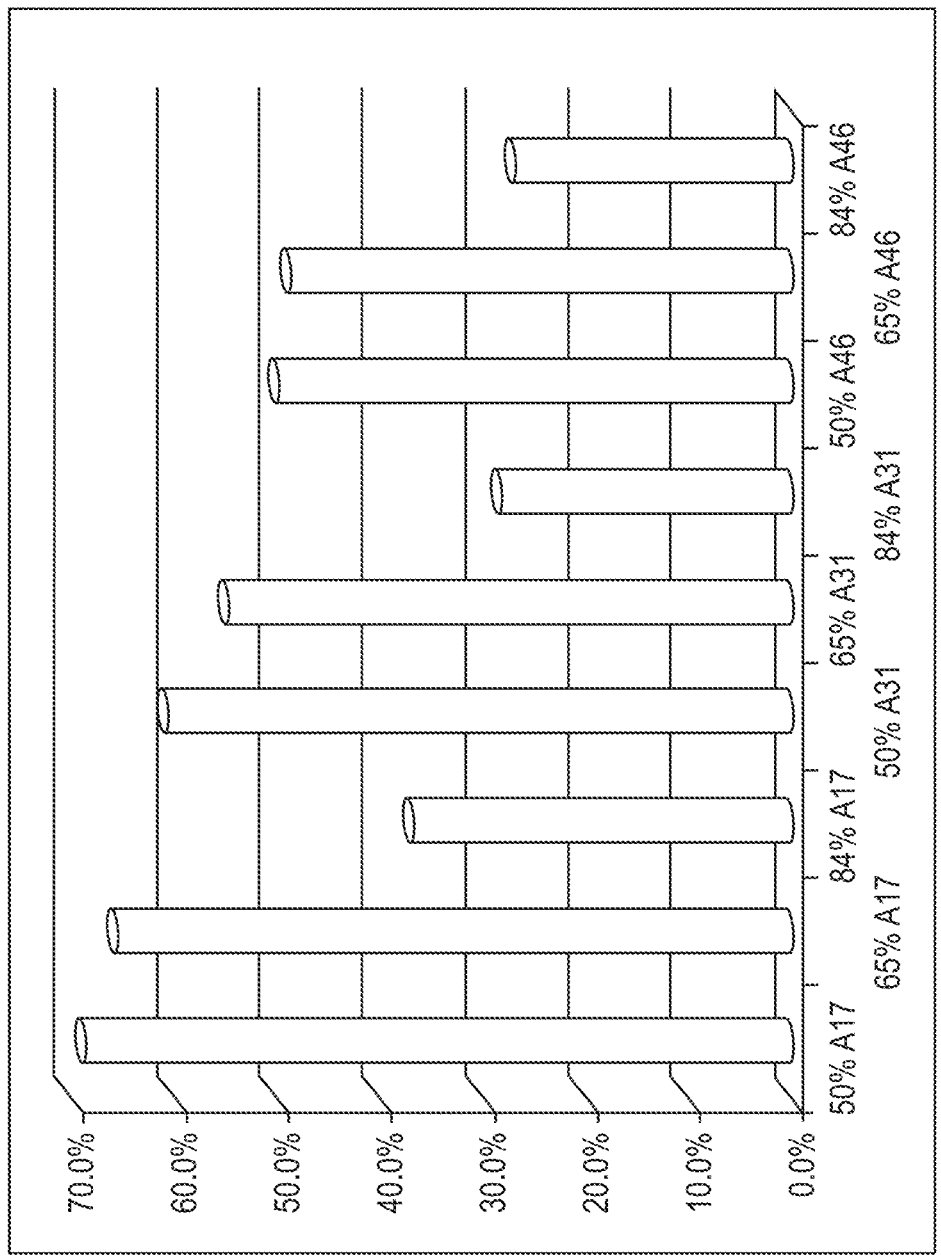
FIG. 1 is a bar graph illustrating various propellant concentrations v. percent fragrance deposition.

The patent or application file contains at least one photograph executed in color. Copies of this patent or patent application publication with color photographs will be provided by the Office upon request and payment of the necessary fee.

DETAILED DESCRIPTION

A spray device, container, composition, propellant, etc. may comprise, consist essentially of, or consist of, various combinations of the materials, features, structures, and/or characteristics described herein.

Reference within the specification to "embodiment(s)" or the like means that a particular material, feature, structure and/or characteristic described in connection with the embodiment is included in at least one embodiment, optionally a number of embodiments, but it does not mean that all embodiments incorporate the material, feature, structure, and/or characteristic described. Furthermore, materials, features, structures and/or characteristics may be combined in any suitable manner across different embodiments, and materials, features, structures and/or characteristics may be omitted or substituted from what is described. Thus, embodiments and aspects described herein may comprise or be combinable with elements or components of other embodiments and/or aspects despite not being expressly exemplified in combination, unless otherwise stated or an incompatibility is stated.

In all embodiments of the present invention, all percentages are by weight of the antiperspirant composition (or formulation), unless specifically stated otherwise. All ratios are weight ratios, unless specifically stated otherwise. All ranges are inclusive and combinable. The number of significant digits conveys neither a limitation on the indicated amounts nor on the accuracy of the measurements. All numerical amounts are understood to be modified by the word "about" unless otherwise specifically indicated. Unless otherwise indicated, all measurements are understood to be made at approximately 25° C. and at ambient conditions, where "ambient conditions" means conditions under about 1 atmosphere of pressure and at about 50% relative humidity. The term "molecular weight" or "M.Wt." as used herein refers to the number average molecular weight unless otherwise stated.

The term "aerosol antiperspirant composition" refers to an antiperspirant composition that is pressurized and/or atomized by a propellant.

The term "aerosol spray device" refers to a spray device that uses a propellant to pressurize an antiperspirant composition and/or atomize an antiperspirant composition when sprayed.

The term "activated" refers to a clay material which has undergone a volume increase.

The term "antiperspirant composition" refers to any composition containing an antiperspirant active and which is intended to be sprayed onto skin, exclusive of a propellant. An antiperspirant composition may be provided in the form of a single phase, liquid dispersion (including suspensions, colloids, or solutions) as opposed to a two phase emulsion.

The term "antiperspirant efficacy" refers to the amount of wetness protection provided by application of an antiperspirant composition to an underarm area (or axillia) by a spray device. Antiperspirant efficacy may be quantified by the amount (mg) of sweat collected following exposure to a hot room compared to a baseline amount.

The term "at the time of making" refers to a characteristic (e.g., viscosity) of a raw material ingredient just prior to mixing with other ingredients.

The term "bulking or suspending material" refers to a material which is intended to reduce settling of a particulate from a liquid and/or reduce the severity of particulate caking post settling.

The terms "clay" and "clay material" refer generally to a variety of: i) clay minerals, including but not limited to the following groups: kaolin (e.g., kaolinite, dickite, halloysite, and nacrite), smectites (e.g., montmorillonite, bentonite, nontronite, hectorite, saponite and sauconite), illites and chlorites; and ii) organoclay materials.

The term "clay activator" refers to a polar material which increases the volume fraction fraction of the clay material and/or the viscosity or yield point of the antiperspirant composition.

The term "clogging" refers to: i) either a blocked passage, orifice, hole or other opening resulting in little or no mass flow out of a container when the actuator is activated, or ii) a valve stuck at least partially open from accumulated composition, resulting in semi-continuous or continuous leakage of the antiperspirant composition and/or a propellant from the spray device, or iii) accumulation of antiperspirant composition within a portion of the flow path of the container which substantially impacts performance of the spray device.

The term "container" and derivatives thereof refers to the package that is intended to store and dispense an antiperspirant composition in a spray type form. A container may typically comprise a reservoir for storing the antiperspirant composition, a valve for controlling flow of the antiperspirant composition, and an actuator by which a user can actuate the valve.

The term "deposition efficiency" refers to the percentage of a material (e.g., antiperspirant active, fragrance material, antiperspirant composition, etc.) that is deposited on a target surface compared to the amount of material that exits in a spray device.

The term "particulate", as used herein, refers to a material that is solid or hollow or porous (or a combination thereof) and which is substantially or completely insoluble in the liquid materials of an antiperspirant composition.

The term "propellant" refers to one or more gases that are used to pressurize the antiperspirant composition to facilitate egress of the antiperspirant composition from the container. Some propellants may be a mixture of gases (e.g., A-46 which is a mixture of isobutane, butane and propane). A propellant may be in the form of a liquid (i.e., a liquefied gas) when under pressure within the reservoir of a spray device. In addition, a propellant may be in its gaseous state within the head space of the reservoir. A propellant may be present in both a liquefied form and its gaseous state within the reservoir. Unless specified otherwise (e.g., liquid propellant or gaseous propellant), the term propellant is intended to encompass the liquefied form and the gaseous state individually and collectively.

The term "substantially free of" refers to an amount of a material that is less than 1%, 0.5%, 0.25%, 0.1%, 0.05%, 0.01%, or 0.001% by weight of an antiperspirant composition. "Free of" refers to no detectable amount of the stated ingredient or thing.

The term "total fill" or "total fill of materials" refers to the total amount of materials added to or stored within a reservoir(s) of a container. For example, total fill includes the propellant and antiperspirant composition stored within a spray device after completion of filling and prior to first use.

The term "viscosity" means dynamic viscosity (measured in centipoise, cPs, or Pascal-second, Pa·s) or kinematic viscosity (measured in centistokes, cSt, or m$^2$/s) of a liquid at approximately 25° C. and ambient conditions. Dynamic viscosity may be measured using a rotational viscometer, such as a Brookfield Dial Reading Viscometer Model 1-2 RVT available from Brookfield Engineering Laboratories (USA) or other substitutable model known in the art. Typical Brookfield spindles which may be used include, without limitation, RV-7 at a spindle speed of 20 rpm, recognizing that the exact spindle may be selected as needed by one skilled in the art. Kinematic viscosity may be determined by dividing dynamic viscosity by the density of the liquid (at 25° C. and ambient conditions), as known in the art.

Without intending to be bound by any theory, it is believed that significant antiperspirant efficacy and/or odor protection may be provided by an antiperspirant composition comprising a non-volatile silicone fluid (to provide good skin adherence) and optionally a liquid fragrance material optionally in combination with a propellant concentration of from about 30% to about 90%, and in another embodiment less than about 70%, and in another embodiment less than 65% or 60%, by weight of the total fill of materials. In some embodiments, it may be desirable for the antiperspirant composition to further comprise a clay material as a bulking/suspending agent to reduce particulate caking and/or aid particulate redispersion and thereby reduce the risk of clogging in the spray device and/or over-dosing and/or inconsistent dosing of the antiperspirant composition.

I. Propellants

A spray device comprises a propellant stored in one or more reservoirs of the container. The propellant may be stored in the same reservoir as an antiperspirant composition or a separate reservoir, although it is preferred that the propellant is stored within the same reservoir as the antiperspirant composition. The propellant may be present in a liquefied form that is miscible with liquid carriers of the antiperspirant composition as well as gaseous state within a head space of the reservoir. The liquid propellant and the antiperspirant composition form a mixture that travels thru container, eventually exiting the container where the liquid propellant vaporizes to form a spray.

The propellant may have a concentration from about 30%, 32%, 34% 36%, 38%, 40%, or 42% to about 90%, 85%, 80%, 75%, or 70%, by weight of the total fill of materials (i.e., propellant and antiperspirant composition) stored within the spray device.

In an embodiment, the propellant may have a concentration from about 72%, 74%, or 76%, to about 80%, 85% or 90% by weight of the total fill of materials (i.e., propellant and antiperspirant composition).

In another embodiment the propellant may have a concentration from about 30%, 32%, 34% 36%, 38%, 40%, or 42% to about 70%, 65%, 60%, 58%, 56%, 54%, 52%, 50%, 48%, 46%, 44%, or 42% by weight of the total fill of materials (i.e., propellant and antiperspirant composition) stored within the spray device.

In one embodiments the amount of liquid propellant (in grams) stored within a container may be from about 4 g, 6 g, 8 g, 10 g to about 45 g, 25 g, 20 g, or 15 g. The volume of liquid propellant stored within the container may be from about 10 mL, 20 mL, 30 mL, or 40 mL to about, 80 mL, 70 mL, 60 mL, or 50 mL.

In another embodiment the propellant may have a concentration from 71%, 72%, 74% 75%, 76%, 77%, or 79% to about 90%, 88%, 86%, 85%, 82%, or 80% by weight of the total fill of materials (i.e., propellant and antiperspirant composition) stored within the spray device. The amount of liquid propellant (in grams) stored within a container may be from about 50 g, 60 g, 70 g, 75 g, 80 g or 85 g to about 135 g, 125 g, 115 g, 105 g, 95 g, or 90 g. The volume of liquid propellant stored within the container may be from about 81 mL, 90 mL, 100 mL, 120 mL, 140 mL or 140 mL to about 225 mL, 200 mL, 180 mL, 170 mL, 160 mL, or 150 mL.

Propellant concentration is one of many design variables that may affect performance of an antiperspirant spray device. For example, propellant concentration may impact the mass flow of the antiperspirant composition. The antiperspirant composition mass flow refers to that portion of the total mass flow of the liquid propellant/antiperspirant composition mixture that is attributable to the antiperspirant composition. As propellant concentration decreases, the density of the liquid propellant/antiperspirant composition mixture increases. Said another way, the antiperspirant composition is less diluted by the liquid propellant. As a consequence, the ratio of antiperspirant composition to liquid propellant in the total mass flow of the mixture increases with decreasing propellant concentration. This effect is most pronounced for hydrocarbon propellants (e.g., butane, isobutene, propane, etc.), which may have a density below that of the antiperspirant composition resulting in a larger volume fraction of the total mass flow. Decreasing propellant concentration may improve antiperspirant efficacy by: 1) increasing antiperspirant composition mass flow (and hence the amount of antiperspirant active deposited on skin per use), and ii) reducing the amount of antiperspirant composition lost to the environment in the form of a gassy cloud (due to less liquid propellant vaporizing and/or a less turbulent spray).

Propellant concentration may also affect the amount of fragrance deposited on skin. Many liquid fragrance materials are soluble in common propellants. As propellant concentration decreases, less of the liquid fragrance material may solubilize in the propellant during storage. Less solubilization may mean less of the fragrance material is lost to the environment as the liquid propellant turns to gas, and therefore more liquid fragrance material may be deposited on the skin as part of the antiperspirant composition. This effect may be seen in FIG. 1, which is a graph of the amount of fragrance deposited on a blotter card for various propellant concentrations (e.g., 84%, 65%, and 50%) and different propellants (e.g., A-46, A-31, and A-17, each propellant having a different equilibrium vapor pressure). The antiperspirant composition comprised dimethicone and a liquid fragrance material comprising known fragrance accords (at a total concentration of ~5.5% by weight of the antiperspirant composition). The antiperspirant composition was sprayed onto commercially available aerosol perfume blotter cards for a period of three seconds from a distance of ~152 mm (6 inches). The total weight dispensed was determined by weighing both the spray device and the blotter cards before and after dispensing. The blotter cards were then individually placed in 125 ml I-chem jars, and the perfume accords were extracted using hexane followed by analysis via liquid injection gas chromatography with mass spectrometric detection to determine the total amount of fragrance deposited, represented in FIG. 1 along the y-axis as the percent deposited.

There appears to be a non-linear relationship in FIG. 1 between the amount of fragrance deposited at 84% propellant concentration and 65% propellant concentration compared to the amount of fragrance deposited at the 65% propellant concentration and the 50% propellant concentration. This relationship appears generally consistent across the three propellant types. It is believed that, in some instances, an improvement in fragrance deposition may be achieved at propellant concentrations less than about 70%, 68%, 65%, 60%, 55%, or 50% by weight of the total fill of materials. This data might also suggest that it is possible to reduce the concentration of the liquid fragrance material by about 40% to 50% as propellant concentration drops from 84% to within the range of 70% to 65% while still maintaining about the same amount of liquid fragrance deposition on skin.

Confoundingly, decreasing propellant concentration may involve a number of negative tradeoffs. First, the lower antiperspirant composition dilution that accompanies decreasing propellant concentration may result in an antiperspirant composition/liquid propellant mixture that has a higher concentration of particulates than a more diluted mixture. This may increase the risk of clogging within the small passages and orifices of a spray device, and further increases the desirability of providing a bulking/suspending system that reduces caking of particulates and aids redispersion thereof upon shaking. Second, increasing the antiperspirant composition mass flow rate too much may lead to over-dosing, which in turn can negatively impact skin feel (e.g., lead to a wet or sticky feel from the presence of too much antiperspirant active on skin) and/or increase the likelihood of a visible residue. Third, it may be desirable to reduce the size of the one or more orifices and/or other flow areas within the container in order to prevent too high of an antiperspirant mass flow. Reducing the size of these flow areas may increase the risk of clogging however and is another reason for the desirability of providing a bulking/suspending system that reduces caking of particulates and aids redispersion thereof upon shaking. Fourth, decreasing the propellant concentration may diminish the cool/fresh feeling at time of application due to less liquid propellant depositing on the skin and subsequently vaporizing there from.

Propellant pressure is another design variable that may also affect the mass flow of the antiperspirant composition/liquid propellant mixture. Different propellants will have different equilibrium pressures within the head space of a reservoir. For example, A-46 (which is a mixture of isobutane, butane and propane) has an equilibrium pressure of 46 psig (317 kPa) while A-31 (which is isobutane) has an equilibrium pressure of 31 psig (213 kPa). As propellant pressure within the head space decreases, the mass flow of the antiperspirant composition/liquid propellant mixture correspondingly decreases (all other variables such as flow path design being constant).

It is believed that propellant concentrations less than 30% by weight of the total fill of the container may result in too high of a mass flow of the antiperspirant composition and/or poor spray characterisitics (i.e. a narrow spray pattern). While reducing the controlling orifice size/area within the container may help offset some of the antiperspirant composition mass flow increase from reducing propellant concentration, propellant concentrations less than 30% may require orifice sizes that are so small that they may become susceptible to clogging and/or which may be more challenging to manufacture in a cost effective manner for commercial products.

A wide variety of propellants may be used with the spray devices and antiperspirant compositions described herein, although in some embodiments the spray device is substantially free of compressed gas propellants such as nitrogen, air and carbon dioxide. Some suitable primary propellants may have a boiling point (at atmospheric pressure) within the range of from about −45° C. to about 5° C. Some suitable propellants may include chemically-inert hydrocarbons such as propane, n-butane, isobutane and cyclopropane, and mixtures thereof, as well as halogenaed hydrocarbons such as dichlorodifluoromethane (propellant 12) 1,1-dichloro-1,1,2,2-tetrafluoroethane (propellant 114), 1-chloro-1,1-difluoro-2,2-trifluoroethane (propellant 115), 1-chloro-1,1-difluoroethylene (propellant 142B), 1,1-difluoroethane (propellant 152A), dimethyl ether and monochlorodifluoromethane, and mixtures thereof. Some propellants suitable for use include, but are not limited to, A-46 (a mixture of isobutane, butane and propane), A-31 (isobutane), A-17 (n-butane), A-108 (propane), AP70 (a mixture of propane, isobutane and n-butane), AP40 (a mixture of propane, isobutene and n-butane), AP30 (a mixture of propane, isobutane and n-butane), Br-46 (a mixture of butane, propane and isobutane), HFO1234 (trans-1,3,3,3-tetrafluoropropene) and 152A (1,1 difluoroethane).

While a wide variety of propellants may be used, there can be some tradeoffs associated with different propellants. For example, utilizing a propellant having boiling point less than −15° C. as a primary propellant may, in some instances, be beneficial, because these propellants quickly expand to form a gas upon exiting the container thereby creating a fine spray and higher spray forces (compared to higher boiling point propellants) to deliver the antiperspirant composition to the target skin surface. Moreover, a propellant having a low boiling point and which is used at a high propellant concentration may result in adiabatic cooling of the antiperspirant composition upon exiting the spray device, aiding the creation of a desirable cool/fresh sensation during application. However, it is believed that the use of these propellants at lower concentrations can result in less adiabatic cooling of the antiperspirant composition and a diminishment in the cool/fresh sensation. It is believed that propellants having boiling points higher than −15° C., used at lower propellant concentrations (e.g., less than about 70%), may provide improved cool/fresh sensation as more of the propellant deposits on the skin and evaporates therefrom, thereby aiding the creation of a cool/fresh sensation. However, too much higher boiling point propellant may deposit on the skin at higher propellant concentrations, resulting in burning or irritation.

At propellant concentrations less than about 70% by weight of the total fill of materials, it may be desirable in some instances for the primary propellant to have a boiling point higher than −12° C., or from about −10° C., −5° C., 0° C. to about 10° C., 5° C. or 0° C. at 1 atmosphere. Propellants comprising n-butane, isobutane, pentane and isopentane may be suitable for use at lower propellant concentrations. In some embodiments, the propellant may comprise more than 50% n-butane. In some embodiments, the propellant comprises a hydrocarbon blend having a vapor equilibrium pressure between about 45 kPa (about 6.5 psig) to about 175 kPa (about 25 psig) at 25° C. Some non-limiting examples of preferred propellants include A-17 and A-20. While these propellants may be suitable for use with the non-volatile silicone fluid antiperspirant compositions described herein, it is believed that these propellants may be suitable for use with other antiperspirant compositions (e.g., comprising other liquid carriers, such as for example a volatile silicone fluid in place of the non-volatile silicone fluid) at propellant concentrations less than about 70%, or 65%, or 60% or 55% to provide a clean/fresh sensation. Some non-limiting examples of other aerosol antiperspirant compositions that may be used are described in U.S. Pat. Nos. 7,951,358; 2007/036,738; 2006/104,918; and 2003/211,060.

In some embodiments, it may also be desirable to provide a mixture of propellants having different boiling points. Combining a primary propellant(s) having a boiling point less than 5° C. with a secondary propellant(s) having a boiling point above 5° C. may increase the likelihood of more liquid propellant reaching the skin surface. This in turn may enhance the cool/fresh sensation at time of application due to the vaporization of the additional liquid propellant (e.g., the secondary propellant) from the skin. The secondary propellant may have a concentration from about 1% to about 20%, or from about 1% to about 15%, or from about 2% to about 10% by weight of the total fill of materials in the product. The secondary propellant(s) may have a boiling point from about 5° C., 10° C., 15° C., 20° C., or 25° C. to about 40° C., 35° C., or 30° C. In some embodiments, the secondary propellant(s) may have a boiling point greater than room temperature, or from 25° C. to 40° C., which can further increase the likelihood that the secondary propellant (s) reaches the skin and vaporizes thereat. Two non-limiting propellants suitable for use as secondary propellants include pentane and isopentane, although other propellants having boiling points within the ranges described herein may also be used.

In some embodiments, it may be desirable to utilize a propellant having an equilibrium pressure, at about 25° C., from about 10 psig (69 kPa), 15 psig (103 kPa), 20 psig (138 kPa), or 25 psig (172 kPa) to about 48 psig (331 kPa), 46 psig (317 kPa), 40 psig (276 kPa), 34 psig (234 kPa) or 32 psig (220 kPA). A-46, A-31, A-20, A-17, and Br-46 are some preferred propellants having equilibrium pressures within these ranges. In some instances, selecting a propellant with a lower equilibrium pressure may permit increasing the size of flow path restrictions to help reduce the risk of clogging without a concomitant increase in the antiperspirant composition mass flow that can accompany increasing the size of a restriction. In some specific embodiments, A-31, A-20 or A-17 may be preferred propellants for helping manage these interdependent tradeoffs.

II. Antiperspirant Compositions

A. Antiperspirant Composition Viscosity

In some embodiments, it may be desirable for the viscosity of the antiperspirant composition to be from about 1,000 centipoise, 2,000 centipoise, or 3,000 centipoise to about 50,000 centipoise 40,000 centipoise, or 30,000 centipoise, or 20,000 centipoise, or 10,000 centipoise, or 5,000 centipoise or 4,000 centipoise at 25° C. (1 centipose being equal to $1\times10^{-3}$ Pa·s). It is believed that a viscosity lower than 1,000 centipoise may lead to an antiperspirant composition, which when spayed, results in a runny or drippy effect on skin. This may be perceived by a user as having a wet rather than dry feel. For comparison, roll-on type antiperspirant compositions often have viscosities below 1,000 centipoise, because the roll-on applicator utilizes a roller ball to apply a thin film of the antiperspirant composition thereby minimizing a runny or drippy effect. Since an antiperspirant composition should be flowable so that it may be sprayed effectively from a spray device, the antiperspirant composition may be devoid of ingredients in sufficient concentrations that provide an antiperspirant stick-type rheology. Some common agents which may be excluded in meaningful amounts include hydrogenated castor oil, solid paraffins, silicone waxes, and mixtures thereof.

B. Non-Volatile Silicone Fluids

The antiperspirant compositions comprise one or more non-volatile silicone fluids. The non-volatile silicone fluid may function as the primary or principal liquid carrier for the antiperspirant active. As used herein, the term "non-volatile" refers to a material that has a boiling point above 250° C. (at atmospheric pressure) and/or a vapor pressure below 0.1 mm Hg at 25° C. Conversely, the term "volatile" refers to a material that has a boiling point less than 250° C. (at atmospheric pressure) and/or a vapor pressure about 0.1 mm Hg at 25° C. Incorporating a non-volatile silicone fluid in an antiperspirant composition may provide several benefits. First, non volatile silicone fluids can be more effectively deposited on the skin than volatile silicone fluids from aerosol antiperspirant compositions containing high levels of propellant, such as greater than 70% or 80% propellant. Deposition of high concentrations of a non-volatile carrier fluid in the antiperspirant composition is believed to reduce visible white residue at application, reduce visible white residue throughout the day and reduce antiperspirant composition transfer to clothes while dressing. This can be illustrated by comparing the deposition of liquids from two test samples. The first test sample comprises 85% A 46 propellant and 15% cyclopentasiloxane by weight of the antiperspirant composition, and the second comprises 85% A 46 and 15% of 50 centistoke dimethicone by weight of the antiperspirant composition. Both test samples used the same valve and actuator combination. The first test sample comprising cyclopentasiloxane had a deposition efficiency of about 24% and the second test sample comprising 50 centistoke dimethicone had a deposition efficiency of about 42%. This represents a 65% improvement in deposition by replacing the cyclopentasilcone with 50 cst dimethicone. While not being bound by any theory, it is believed that the lower deposition of antiperspirant composition comprising cyclopentasiloxane may result from both inherent volatility of the volatile silicone fluid which can allow it to begin evaporating prior to deposition and a higher solubility of the antiperspirant composition in the propellant resulting in an increase in the evaporation rate as the antiperspirant composition is co-vaporized with the propellant as both are expelled from the container. Second, incorporating a non-volatile silicone fluid may increase the substantivity of the antiperspirant composition on skin, thereby potentially increasing antiperspirant efficacy, as the antiperspirant composition may form a film that more readily adheres to skin rather than flaking off or transferring to clothing throughout the day. Third, incorporating a non-volatile silicone fluid may also decrease the propensity for a visible residue to appear on skin (compared to using a volatile silicone fluid), as the non-volatile silicone fluid does not evaporate thereby leaving behind the white antiperspirant active as a visible residue. However, incorporating a non-volatile silicone fluid is not without potential tradeoffs. A perception of wetness post application (which may be undesirable for some consumers) is one tradeoff that may be associated with high concentrations of a non-volatile silicone fluid in an antiperspirant composition.

The total concentration of non-volatile, silicone fluids may be from about 30%, 35%, 40%, 45%, 50% to about 70%, 65%, 60%, 55% or 50% by weight of an antiperspirant composition. In some embodiments, the total concentration of non-volatile, silicone fluids may be from about 35% to about 55% by weight of an antiperspirant composition. The liquid materials of the antiperspirant composition may consist essentially of or primarily comprise a non-volatile, silicone fluid(s). Some non-volatile, silicone fluids that may be used include, but are not limited to, polyalkyl siloxanes, polyalkylaryl siloxanes, and polyether siloxane copolymers, and mixtures thereof. Some preferred non-volatile silicone fluids may be linear polyalkyl siloxanes, especially polydimethyl siloxanes (e.g., dimethicone). These siloxanes are available, for example, from Momentive Performance Materials, Inc. (Ohio, USA) under the tradename Element 14 PDMS (viscosity oil). Silicones Fluids from Dow Corning Corporation (Midland, Mich., USA) available under the trade name Dow Corning 200 Fluid series (e.g., 3 to 350 centistokes). Other non-volatile silicone fluids that can be used include polymethylphenylsiloxanes. These siloxanes are available, for example, from the General Electric Company as SF 1075 methyl phenyl fluid or from Dow Corning as 556 Fluid. A polyether siloxane copolymer that may be used is, for example, a dimethyl polyoxyalkylene ether copolymer fluid. Such copolymers are available, for example, from the General Electric Company as SF-1066 organosilicone surfactant. The non-volatile, silicone fluid may have an average viscosity from about 3 centistokes, 5 centistokes, 10 centistokes, 20 centistokes, or 50 centistokes to about 350 centistokes, 200 centistokes, 100 centistokes, 50 or 30 centistokes at 25° C. (1 centistoke being equal to $1 \times 10^{-6}$ m$^2$/s). In some specific embodiments, the silicone fluid may have a viscosity from about 5 centistokes to about 100 centistokes or 5 centistokes to about 50 centistokes or about 5 centistokes to about 30 centistokes. In some instances, the non-volatile silicone fluid is a polydimethylsiloxane fluid (also commonly referred to as dimethicone). It will be appreciated that a polydimethylsiloxane fluid may be further characterized by, optionally, its viscosity or its molecular weight or its formula or a combination thereof. In some instances, the polydimethylsiloxane fluid may have the following characteristics:

TABLE 1

| Viscosity | Approximate Molecular Weight[1] | Approximate Average Number of Monomer Units in the Polymer[1] |
|---|---|---|
| 3 Centistokes | 500 | 6 |
| 5 Centistokes | 800 | 9 |
| 10 Centistokes | 1200 | 13 |
| 20 Centistokes | 2000 | 27 |
| 30 Centistokes | 2600 | 35 |
| 50 Centistokes | 3800 | 50 |
| 100 Centistokes | 6000 | 80 |
| 200 Centistokes | 9400 | 125 |
| 350 Centistokes | 13,700 | 185 |

[1]The compositions of Examples 1 to 24 and FIGS. 1 to 12, to the extent they contained a dimethicone fluid, were formulated utitlizing a Dow Corning DC200 series fluid, which is believed to have had average molecule weights and average number of monomer subunits falling within the approcximate values of above-described table.

The polydimethylsiloxane fluid may have the following formula (II):

$$M\text{-}D_X\text{-}M$$

wherein M is (CH$_3$)$_3$SiO and D is 2CH$_3$(SiO) and X is equal to the average number of monomer units (see, e.g., Table 1) in the polymer minus 2. In some embodiments, X may be from about 6 to about 185, from about 9 to about 125, from about 9 to about 80, from about 9 to about 50, from about 13 to about 50 or from about 27 to about 50. In other embodiments, X may be from about 6 to about 35, from about 9 to about 35 or from about 13 to about 35. The term "approximate" as used in Table 1 refers to ±10% of a given value.

Figure 2:
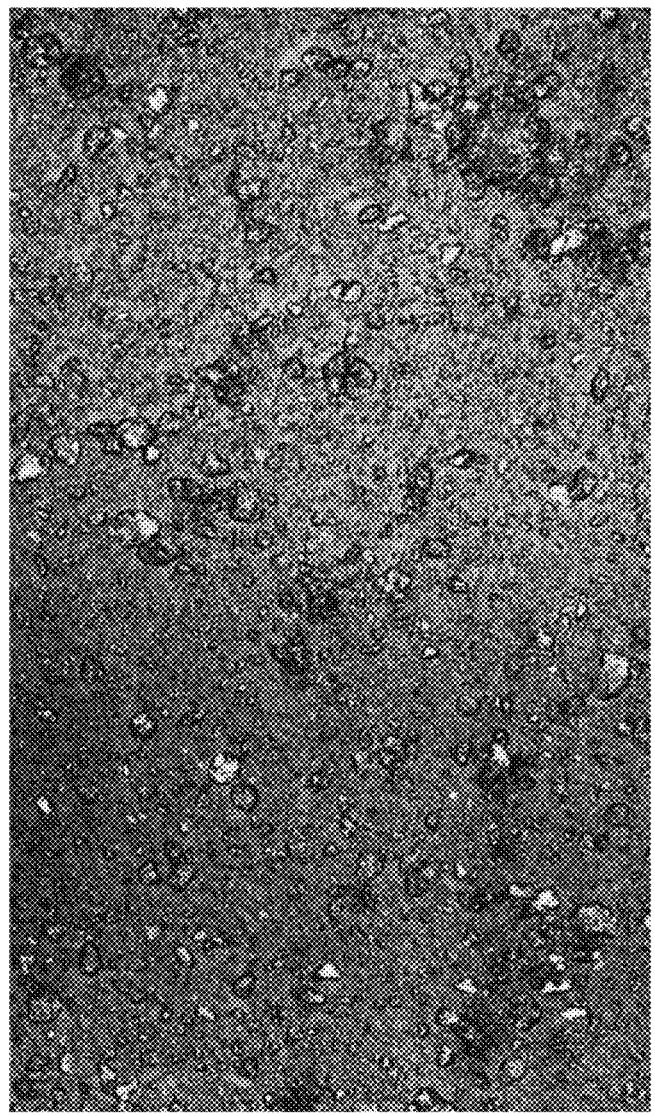
FIG. 2 is a 50× photomicrograph, taken using differential interference contrast, of a composition comprising 50 centistoke dimethicone, disteardimonium hectorite and triethyl citrate.
Figure 3:
FIG. 3 is a 50× photomicrograph, taken using differential interference contrast, of a composition comprising cyclopentasiloxane, disteardimonium hectorite and triethyl citrate.

While there are benefits to including a non-volatile silicone fluid, it is believed that a non-volatile silicone fluid may in some instances negatively affect activation of a clay material compared to a more traditional liquid carrier, such as cyclopentasiloxane. An example of this effect may be seen by comparing FIGS. 2 and 3. FIG. 2 is a photomicrograph illustrating the nature of the clay activation in a composition comprising 50 centistokes dimethicone (about 86.5% w/w), disteardimonium hectorite (about 10.2% w/w) and triethyl citrate (about 3.3% w/w), while FIG. 3 is a comparative photomicrograph illustrating the nature of clay activation in a composition comprising cyclopentasiloxane (about 86.5% w/w), disteardimonium hectorite (about 10.2% w/w) and triethyl citrate (about 3.3% w/w). The composition of FIG. 2 contains numerous agglomerations of the clay material (compared to FIG. 3), illustrating the relatively poorer activation of the clay material compared to FIG. 3. Without intending to be bound by any theory, it is believed that this poorer activation may result from weak interactions between the dimethicone and the clay material. Dimethicone, like many non-volatile silicone fluids, has weak hydrogen bonding and Van der Waal forces, and as a result may be unable to easily interact with or loosely bind to the modified or native portions of the clay material. This lack of interaction may result in clay platelets interacting too strongly with other clay platelets and formation of the agglomerates that are seen in FIG. 3.

This relatively poorer activation is further illustrated by comparative Examples 1 and 4. The antiperspirant composition of Example 1 comprised, in part, cyclopentasiloxane (about 52.5% w/w), disteardimonium hectorite (about 4.25% w/w) and triethyl citrate (about 1.38% w/w). The antiperspirant composition of Example 4 comprised, in part, 50 centistoke dimethicone (about 52.5% w/w), disteardimonium hectorite (about 4.25% w/w) and triethyl citrate (about 1.38% w/w). The dispersion/redispersion characteristics of an antiperspirant composition may be quantitatively/qualitatively assessed by measuring the height of the antiperspirant composition after long term settling (24 hours) and short term settling (2 minutes) of the antiperspirant composition and/or by the number of rotations or turns of a glass bottle containing the antiperspirant composition that are needed to redisperse the antiperspirant composition. Better clay activation may be evidenced by greater heights and/or lower turns. The antiperspirant composition of Example 1 redispersed well with an average (n=3) of 6.3 turns, a long term settling height of 17 mm and a short term settling height of 32 mm. In contrast, the antiperspirant composition of Example 4 dispersed more poorly (in clumps) with an average (n=3) of 8 turns, a long term settling height of 12 mm and short term settling height of 14 mm, substantially less than Example 1.

C. Liquid Fragrance Materials

An antiperspirant composition may also optionally comprise one or more liquid fragrance materials. Liquid fragrance materials are typically a mixture of perfume or aromatic components that are optionally mixed with a suitable solvent, diluent or carrier. Some or many of the perfume components, when combined, may result in a highly polar liquid fragrance material. Some suitable solvents, diluents or carriers for the perfume components may include ethanol, isopropanol, diethylene glycol monoethyl ether, dipropylene glycol, diethyl phthalate, triethyl citrate, isopropyl myristate and mixtures thereof. An antiperspirant composition may comprise from about 2%, 3% or 4% to about 10%, 8%, 6%, or 4% by weight of a liquid fragrance material.

Without intending to be bound by any theory, it is believed that, in some instances, a liquid fragrance concentration less than about 2% by weight of the antiperspirant composition may not deliver sufficient long lasting scent throughout the day For example, in some instances, it may be desirable for the fragrance to last greater than 8 hrs, 10 hrs, 12 hrs, 14 hrs or 16 hrs. Two antiperspirant formulas were tested in a fragrance longevity test involving 68 panelists, who were employees of the assignee. This was a randomized, blinded, paired comparison test where half the panelists applied a control aerosol antiperspirant composition on the right underarm and half applied a control aerosol antiperspirant composition on the left underarm. Two blinded, test antiperspirant compositions were tested. The first antiperspirant composition comprised 50 centistoke dimethicone (49.5% w/w), aluminum chlorohydrate (about 26.4% w/w), a tapioca material (about 12% w/w), disteardimonium hectorite (about 4.2% w/w), isopropyl myristate (about 4% w/w), a liquid fragrance material (about 2% w/w), triethyl citrate (about 1.4% w/w) and dimethicone/dimethiconol (about 0.5% w/w). The liquid fragrance material also contained small amounts (about 15% or less by w/w of the liquid fragrance material) of isopropyl myristate as a diluent. The second antiperspirant composition comprised 50 centistoke dimethicone (about 46.5% w/w), aluminum chlorohydrate (about 26.4% w/w), tapioca material (about 12% w/w), distreardimonium hectorite (about 4.2% w/w), isopropyl myristate (about 4% w/w), a liquid fragrance material (about 5% w/w), triethyl citrate (about 1.4% w/w) and dimethicone/dimethiconol (about 0.5% w/w). The liquid fragrance material also contained small amounts (about 15% or less by w/w of the liquid fragrance material) of isopropyl myristate as a diluent. The antiperspirant composition was added to the reservoir of a spray device along with A-31 propellant to achieve a 35% w/w concentration of the antiperspirant composition and 65% w/w concentration of the propellant. The difference between the first and second antiperspirant composition was the concentration of liquid fragrance material and the concentration of the dimethicone. Table 2 below sets forth the mean values (on a scale from 0 to 8, wherein 8 represents the strongest or most noticeable experience) of the fragrance ratings by the panelists for the first and second antiperspirant compositions at the time of application, at 4 hrs, at the "change of shirt" (which may be from 8 to 16 hrs) and at the following morning.

TABLE 2

|  | First Antiperspirant Composition (2% w/w Liquid Fragrance Material) | Second Antiperspirant Composition (5% w/w Liquid Fragrance Material) |
| --- | --- | --- |
| Fragrance at application | 5.7 | 7 |
| Fragrance at 4 hrs | 3.7 | 5.2 |
| Fragrance at change of shirt | 2.4 | 3.5 |
| Fragrance at 24 hrs | 0.8 | 1.1 |
| Fresh/clean scent at application | 6.4 | 7.5 |
| Fresh/clean scent at 4 hrs | 5 | 6.1 |
| Fresh/clean scent at change of shirt | 3.6 | 4.4 |
| Fresh/clean scent at 24 hrs | 2.9 | 3.3 |

It is believed that a mean value greater 3.5 may be desirable for providing an acceptable fragrance experience. It appears that, in at least some instances, liquid fragrance material concentrations less than about 2% by weight of the antiperspirant composition may be less desirable for providing a long lasting scent experience at a "change of shirt" time point and/or 24 hrs after application in antiperspirant compositions comprising a non-volatile silicone fluid and propellant concentration less than about 70% by weight of the total fill of materials. Furthermore it is believed that fragrance levels less than about 4% may be less desirable for providing a long lasting scent experience in antiperspirant compositions comprising a non-volatile silicone fluid and propellant concentration more than 71% by weight of the total fill of materials.

The perfume component may be any natural or synthetic perfume component known to one skilled in the art of creating fragrances including, but not limited to, essential oils, citrus oils, absolutes, resinoids, resins, concretes, etc., and synthetic perfume components such as hydrocarbons, alcohols, aldehydes, ketones, ethers, acids, esters, acetals, ketals, nitriles, etc., including saturated and unsaturated compounds, aliphatic, carbocyclic and heterocyclic compounds. Some non-limiting examples of perfume components include: geraniol, geranyl acetate, linalool, linalyl acetate, tetrahydrolinaloool, citronellol, citronellyl acetate, dihydromyrcenol, dihydromyrcenyl acetate, tetrahydromyrcenol, terpineol, terpinyl acetate, nopol, nopyl acetate, 2-phenylethanol, 2-phenylethyl acetate, benzyl alcohol, benzyl acetate, benzyl salicylate, benzyl benzoate, styrallyl acetate, amyl salicylate, dimethylbenzyl carbinol, trichloromethylphenyl-carbinyl acetate, p-tert.butyl-cyclohexyl acetate, isononyl acetate, vetiveryl acetate, vetiverol, alpha-n-amylcinammic aidehyde, alpha-hexylcinammic aldehyde, 2-methyl-3-(p-tert.butylphenyl)-propanol, 2-methyl-3-(p-isopropylphenyl)-propanal, 3-(p-tert.butylphenyl)-propanal, tricyclodecenyl acetate, tricyclodecenyl propionate, 4-(4-hydroxy-4-methylpentyl)-3-cyclohexene carbaldehyde, 4-(4-methyl-3-pentenyl)-3-cyclohexene carbaldehyde, 4-acetoxy-3-pentyltetrahydropyran, methyldihydrojasmonate, 2-n-heptylcyclopentanone, 3-methyl-2-pentylcyclopentanone, n-decanal, 9-decenol-1, phenoxyethyl isobutyrate, phenyl-acetaldehyde dimethyl acetal, phenylacetaldehyde diethyl acetal, geranonitrile, citronellonitrile, cedryl acetate, 3-isocamphylcyclohexanol, cedryl methyl ether, isolongifolanone, aubepine nitrile, aubepine, heliotropine, coumarin, eugenol, vanillin, diphenyl oxide, hydroxycitronellal, ionones, methylionones, isomethylionones, irones, cis-3-hexenol and esters thereof, indane musk fragrances, tetralin musk fragrances, isochroman musk fragrances, macrocyclic ketones, macrolactone musk frangrances, ethylene brassylate, aromatic nitro-musk fragrances. Some perfume components are also described in Arctander, Perfume and Flavour Chemicals (Chemicals), Vol. I and II (1969) and Arctander, Perfume and Flavour Materials of Natural Origin (1960).

Figure 4:
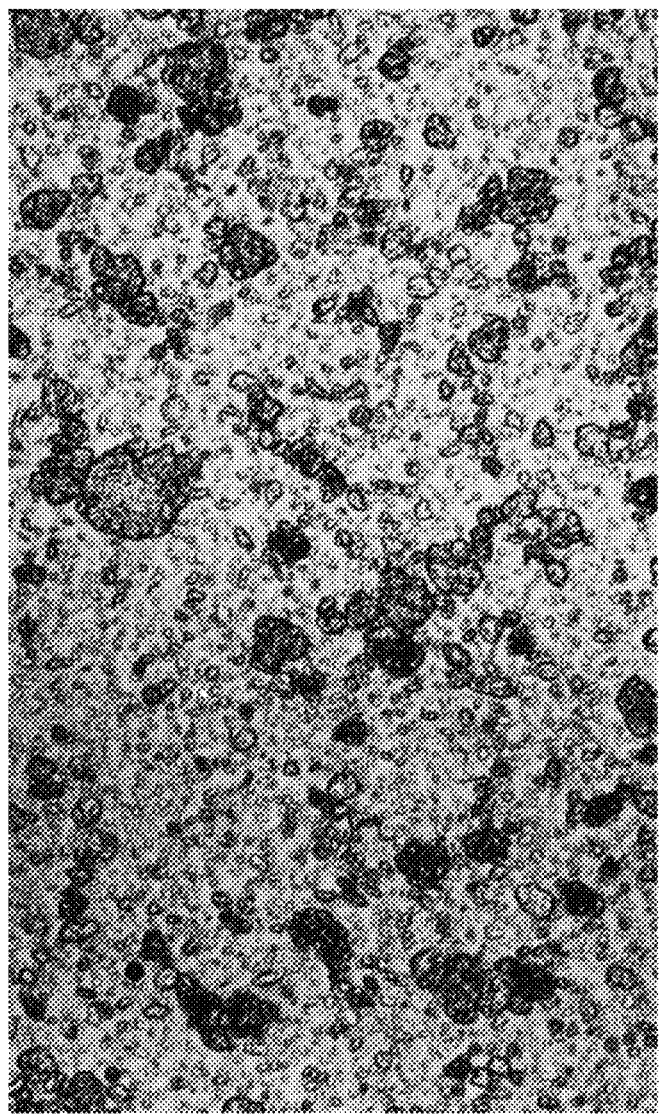
FIG. 4 is a 50× photomicrograph, taken using differential interference contrast, of a composition comprising 50 centistoke dimethicone, disteardimonium hectorite, triethyl citrate and a liquid fragrance material.
Figure 5:
FIG. 5 is a 50× photomicrograph, taken using differential interference contrast, of a composition comprising cyclopentasiloxane disteardimonium hectorite, triethyl citrate and a liquid fragrance material.

While there are benefits to including a liquid fragrance material in an antiperspirant composition, it is believed that at least some fragrance materials may negatively affect activation of a clay material and thereby further compound the negative effect introduced by a non-volatile silicone fluid. This may become more apparent as the liquid fragrance material concentration increases, particularly at higher liquid fragrance material concentrations (e.g., greater than about 2% w/w) that may be desirable in some instances. FIG. 4 is a photomicrograph illustrating the nature of the clay activation in a composition comprising 50 centistoke dimethicone (about 76.4% w/w), disteardimonium hectorite (about 9% w/w), triethyl citrate (about 2.9% w/w) and a liquid fragrance material (about 11.7% w/w). It is believed that the liquid fragrance material also contained small amounts (about 10% or less by w/w of the liquid fragrance material) of isopropyl myristate as a diluent. FIG. 5 is a comparative photomicrograph illustrating the nature of clay activation in a composition comprising cyclopentasiloxane (about 76.4% w/w), disteardimonium hectorite (about 9% w/w/), triethyl citrate (about 2.9% w/w) and a liquid fragrance material (about 11.7% w/w). It is believed that the liquid fragrance material also contained small amounts (about 10% or less by w/w of the liquid fragrance material) of isopropyl myristate as a diluent. The composition of FIG. 4 contains numerous agglomerations of the clay material compared to FIG. 5 (and even larger agglomerations than observed in FIG. 2), illustrating the relatively poorer activation of the clay material.

This relatively poorer activation associated with the addition of a liquid fragrance material is further illustrated by comparative Examples 2 and 5. The composition of Example 2 comprised, in part, cyclopentasiloxane (about 47% w/w), disteardimonium hectorite (about 4.25% w/w), triethyl citrate (about 1.38% w/w) and a liquid fragrance material (about 5.5% w/w). The antiperspirant composition of Example 5 comprised, in part, 50 centistoke dimethicone (about 47% w/w), disteardimonium hectorite (about 4.25% w/w), triethyl citrate (about 1.38% w/w) and a liquid fragrance material (about 5.5% w/w). The antiperspirant composition of Example 2 redispersed well with an average (n=3) of 10 turns, a long term settling height of 15 mm and a short term settling height of 42 mm. In contrast, the antiperspirant composition of Example 5 dispersed more poorly (with clumps of the composition remaining stuck on the bottom of the bottle even after 5 turns) with an average (n=3) of 19 turns, a long term settling height of 10 mm and a short term settling height of 19 mm4. Without intending to be bound by any theory, it is believed that the combination of a non-volatile silicone fluid, a liquid fragrance material and a clay material may result in less desirable clay activation compared to the combination of a volatile silicone fluid, a liquid fragrance material and a clay material. It is further believed that polar liquid fragrance materials may more negatively impact clay activation, with the negative effect increasing as the degree of polarity increases and as the concentration of the liquid fragrance material increases. These disadvantages may be minimized, however, by including liquid activation enhancer, clay activator, and/or by the method of addition steps, discussed herein.

D. Clay Materials and Clay Activators

An antiperspirant composition comprises a clay material as a bulking or suspending agent. The concentration of clay material may be from about 1%, 2%, 3% to about 8%, 6%, 5%, or 4% by weight of the antiperspirant composition. In some embodiments, the concentration of the clay material is from about 2% to about 6% by weight of the antiperspirant composition. In some embodiments, the total particulates of antiperspirant composition may comprise from about 5% to about 20% or 5% to 15% of a clay material. In some embodiments clay materials are organoclays, which may be derived from clay minerals in which a portion of the inorganic cationic counter ions (e.g., sodium cations) of the clay mineral have been exchanged for organocations (e.g., quartenary ammonium chloride) thereby rendering the material organophilic rather than hydrophilic. Shearing/milling of the clay material deagglomerates the clay material platelets after which a polar clay activator may be added in some instances to further separate the platelets and promote the formation of hydrogen bonds between the edges of adjacent platelets. This enables formation of a higher volume three dimensional clay structure that suspends the particulates of the antiperspirant composition. This also increases the volume of the clay material in the antiperspirant composition, thereby increasing the volume or bulk of the total powder of the antiperspirant composition. This is also why the settling height of an antiperspirant composition may be one quantitative/qualitative measure of the amount/quality of activation of a clay material.

Some non-limiting examples of clay materials include montmorillonite clays and hydrophobically treated montmorillonite clays. Montmorillonite clays are those which contain the mineral montmorillonite and may be characterized by a having a suspending lattice. Some examples of these clays include but are not limited to bentonites, hectorites, and colloidal magnesium aluminum silicates. Some non-limiting examples of organoclays include modified bentonite, modified hectorite, modified montorlinite and combinations thereof, some examples of which are available under the trade names Bentone 27 (stearalkonium bentonite), Bentone 34 (stearalkonium bentonite) and Bentone 38 (disteardimonium hectorite) from Elementis Specialities Plc. and Tixogel VPV (quaternium 90-bentonite), Tixogel VZV (stearalkonium bentonite), Tixogel LGM (stearalkonium bentonite) and Claytone SO (stearalkonium bentonite) from Southern Clay Products. In some instances, the bulking and suspending material consists substantially of, essentially of and/or primarily of a clay material and more preferably an organoclay material. In these instances, the antiperspirant composition may be substantially or completely free of silica materials used as a bulking/suspending material.

The antiperspirant composition may also comprise a clay activator, such as propylene carbonate, triethyl citrate, methanol, ethanol, acetone, water and mixtures and derivatives thereof. Without intending to be bound by any theory, it is believed that the clay activator enhances the hydrogen bonds between the edges of adjacent clay platelets. Too little clay activator may provide insufficient hydrogen bonding between clay platelets while too much may create very strong interactions resulting in formation of agglomerates and loss of the desired bulking benefit. The clay activator may have a concentration ranging from 1:3 to 2:3 parts clay activator to clay material. Clay activators may also strongly interact with an antiperspirant active (e.g., leading to clumping or coating of the antiperspirant active and/or changes in active polymer structure which may reduce antiperspirant efficacy). Therefore, it may be desirable to limit the amount of clay activator present in the antiperspirant composition to between about 0.5%, 0.75%, 1%, 1.25%, or 1.5% to about 3%, 2%, or 1.75% by weight of the antiperspirant composition.

E. Liquid Activation Enhancer

Without intending to be bound by any theory, it is believed that certain liquid materials may help maintain and/or promote the clay bulking and suspending benefit in an antiperspirant composition that comprises a non-volatile silicone liquid, and optionally a liquid fragrance material, by facilitating increased interaction or loose bonding between the non-volatile silicone fluid and the clay material. It is believed that the increased interaction may be facilitated, in some instances, when the liquid activation enhancer is soluble in the non-volatile silicone and has a Hansen Solubility Parameter for Hydrogen Bonding, $\delta_h$, between about 2 MPa$^{1/2}$ and about 6 MPa$^{1/2}$.

Liquid activation enhancers that are soluble in the non-volatile silicone fluid may advantageously: 1) disperse within the non-volatile silicone fluid, thereby promoting a more uniform interaction or loose bonding between the clay material and the non-volatile silicone fluid, and/or 2) minimize regions of high clay activation by increasing the solubility and/or disperseability of the clay activator and/or optional liquid fragrance material, thereby reducing the risk of locally high concentrations of the clay activator and/or liquid fragrance material which may result in clay precipitation. Solubility may be determined by measuring the amount of light transmittance (a light transmittance value) through a simple mixture of the non-volatile silicone fluid and liquid activation enhancer at the same weight/weight concentrations as in a final antiperspirant composition. For example, the solubility of a liquid activation enhancer at a concentration of 9% w/w in a final antiperspirant composition comprising a non-volatile silicone fluid having a concentration of 38% w/w can be determined by measuring the light transmittance of a simple mixture of the liquid activation enhancer at 19% w/w concentration in just the non-volatile silicone fluid. Light transmittance may be measured using a spectrophotometer, such as, for example, a Spectronic Genesys 10 Vis Spectrophotometer available from Thermo Electron Corp (USA), wherein a light transmittance value greater than 80%, 85%, 90% or 95% at 25° C. indicates sufficient solubility in the non-volatile silicone fluid.

It is also believed that a liquid activation enhancer having a $\delta_h$ value between 2 MPa$^{1/2}$ and 6 MPa$^{1/2}$ may also promote interaction or loose bonding between non-volatile silicone fluid and the clay material. It is believed that $\delta_h$ values less than about 2 MPa$^{1/2}$ may be insufficient to provide adequate interaction or loose bonding between the non-volatile silicone fluid and the clay material while values greater than about 6 may result in collapse of the three dimensional clay structure due to the creation of strong hydrogen bonding between the clay platelets. In some instances, it may also be desirable that the liquid activation enhancer is also capable of solubilizing both the liquid fragrance material and the clay activator in order to avoid regions of high/low clay activation, as these materials may not be easily solubilized in non-volatile silicone fluids.

An antiperspirant composition comprises at least one liquid activation enhancer. The at least one liquid activation enhancer, or the combination of a plurality of activation enhancers, may have a total concentration from about 2%, 4%, 6%, 8%, 10% to about 30%, 25%, 20%, 18%, 16%, 14%, 12%, 10% or 8% by weight of the antiperspirant composition. In some embodiments, the liquid activation enhancer has a concentration from about 2% to about 15% by weight of the antiperspirant composition. It is believed that concentrations higher than 30% may impact spreading of the antiperspirant composition on skin by increasing the surface tension of the composition, which is one mechanism by which a dry skin feel may be imparted in an antiperspirant composition comprising a non-volatile silicone fluid. It also believed that concentrations less than 2% may be too low to provide sufficient interaction between the clay material and the non-volatile silicone fluid Some preferred liquid activation enhancers are molecules comprising a fatty or hydrocarbon group and a functional group that is capable of hydrogen bonding near or at one terminus of the hydrocarbon group. The hydrocarbon chain may be from about 8 to about 20 carbon atoms in length ($C_8$ to $C_{20}$) to provide the desired solubility in the non-volatile silicone fluid. The hydrocarbon chain may be linear, branched, unbranched, saturated or unsaturated. The hydrogen bonding group may be selected from the group consisting of alcohol, ester, amide and aryl/aromatic groups. Most preferred are hydrogen bonding accepting groups such as esters and aromatic groups. Some non-limiting examples of these materials include esters and amides formed from the reaction of fatty acids, fatty amines, or fatty alcohols with alcohols, amines, or carboxylic acids. Some non-limiting examples of fatty acids, fatty amines, and fatty alcohols include stearic acid, palmitic acid, myristic acid, lauric acid, stearyl amine, palmityl amine, myristyl amine, stearyl alcohol, palmityl alcohol, myristyl alcohol and lauryl alcohol. Some non-limiting examples of alcohols, amines, or carboxylic acids include, methanol, ethanol, propanol, isopropanol, butanol, isobutanol, phenyl alcohol, benzyl alcohol, phenol, methyl amine, ethyl amine, propyl amine, butyl amine, benzyl amine, formic acid, acetic acid, propanoic acid, butyric acid and benzoic acid.

Some non-limiting examples of liquid activation enhancers include isopropyl myristate, isopropyl palmitate, ethyl stearate, methyl stearate, propyl stearate, butyl stearate, ethyl myristate, ethyl palmitate, butyl palmitate, propyl stearate, propyl palmitate, methyl stearamide, ethyl stearamide, isopropyl stearamide, ethyl palmitamide propyl palmitamide, stearyl benzoate, palmityl benzoate, C12-15 alkyl benzoate, benzyl palmitate, benzyl stearate, dodecylenbenezene and palmityl acetate. Liquid activation enhancers might also include fatty branched chain alcohols and ethoxylated fatty alcohols. The liquid activation enhancer may have the following formula (I):

wherein $R_1$ contains from about 8 to about 20 carbon atoms, X is selected from the group consisting of an alcohol, ester, amide and aryl groups, and $R_2$ is selected from the group consisting of null, hydrogen (H), 1 to 4 carbon atoms, and $C_6H_5$.

Figure 6:
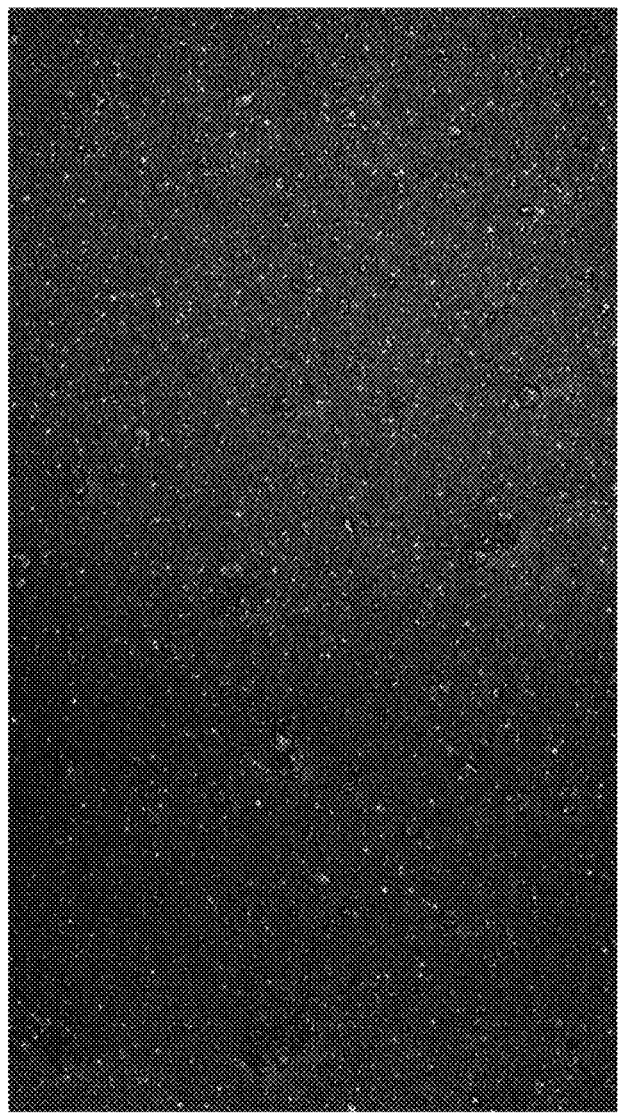
FIG. 6 is a 50× photomicrograph, taken using differential interference contrast, of a composition comprising 50 centistoke dimethicone, disteardimonium hectorite, triethyl citrate and isopropyl myristate.
Figure 7:
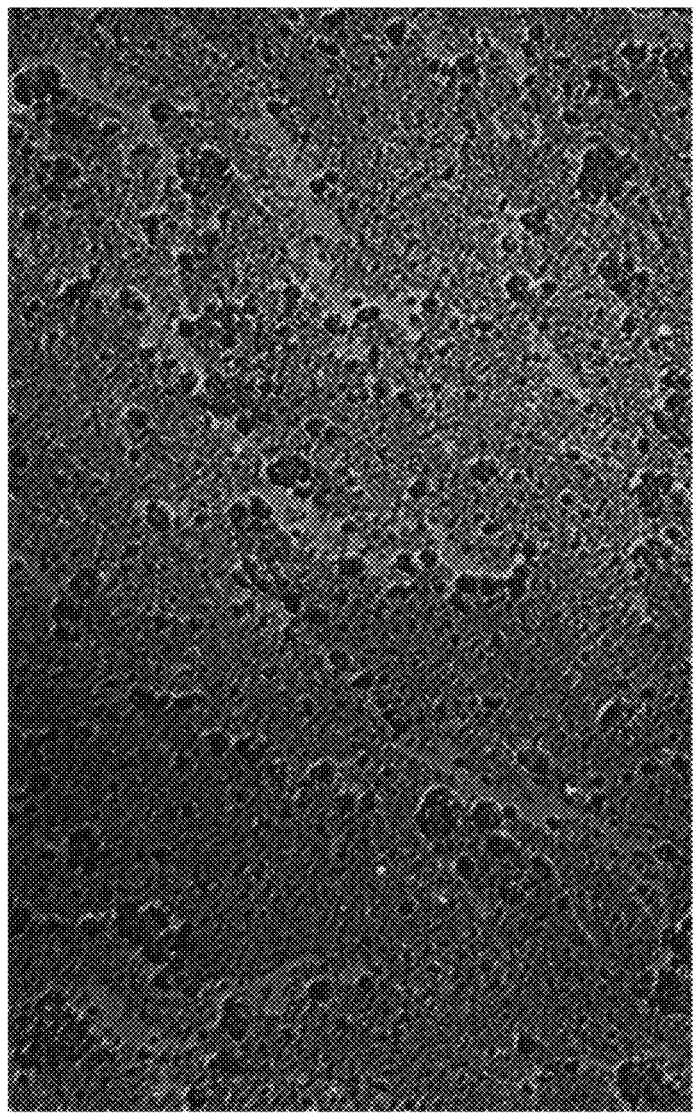
FIG. 7 is a 50× photomicrograph, taken using differential interference contrast, of a composition comprising 50 centistoke dimethicone, disteardimonium hectorite, triethyl citrate, a liquid fragrance material and isopropyl myristate.

Some particularly preferred non-limiting examples of liquid activation enhancers suitable for use include isopropyl myristate ($\delta_h$=about 2.95, light transmittance values about 101% at concentrations from 2% to 30% w/w in 50 centistoke dimethicone), isopropyl palmitate ($\delta_h$=about 3.15, light transmittance values about 101% at concentrations from 2% to 30% w/w in 50 centistoke dimethicone), butyl stearate ($\delta_h$=about 3.45, light transmittance values about 100% at concentrations from 2% to 30% w/w in 50 centistoke dimethicone) and, in some instances, C12-15 alkyl benzoate (available under the trade name Finsolv® from Innospec Performance Chemicals, USA) and combinations thereof. Turning first to isorpoyl myristate, FIG. 6 is a photomicrograph illustrating the nature of the clay activation in a composition comprising 50 centistoke dimethicone (65% w/w), disteardimonium hectorite (10.2% w/w), triethyl citrate (2.9% w/w) and isopropyl myristate (21.5% w/w). FIGS. 6 and 3 appear similar, thereby illustrating the beneficial effect of adding isopropyl myristate. FIG. 7 is a photomicrograph illustrating the nature of the clay activation in a composition comprising 50 centistoke dimethicone (about 57.4% w/w), disteardimonium hectorite (about 9% w/w), triethyl citrate (about 2.9% w/w/), a isopropyl myristate (about 19% w/w) and a liquid fragrance material (about 11.7% w/w). It is believed that the liquid fragrance material also contained small amounts (about 10% or less by w/w of the liquid fragrance material) of isopropyl myristate as a diluent. The addition of the liquid fragrance material degraded somewhat the clay activation compared to FIG. 6, as evidenced by some agglomeration of the clay material, however the addition of the isopropyl myristate significantly improved the clay activation compared to FIG. 4. The relatively better clay activation provided by the incorporation of isopropyl myristate is further illustrated by Examples 7 and 8. The composition of Example 7 comprised, in part, 50 centistoke dimethicone (about 43.5% w/w), isopropyl myrisate (about 9% w/w) and disteardimonium hectorite (about 4.25% w/w). The composition of Example 8 comprised, in part, 50 centistoke dimethicone (about 38% w/w), isopropyl myrisate (about 9% w/w), disteardimonium hectorite (about 4.25% w/w) and a liquid fragrance material (about 5.5% w/w). The antiperspirant composition of Example 7 redispersed well with an average (n=3) of 6.3 turns, a long term settling height of 17 mm and a short term settling height of 33 mm, which appear similar to the settling and redispersion characteristics of comparative Example 1. The addition of the liquid fragrance material in Example 8 resulted a long term settling height of 13 mm, an average (n=3) of 12 turns, and a short term settling height of 40 mm. These settling and redispersion characteristics appear to be an improvement over Example 5.

Turning now to Examples, 10 and 11, the relatively better clay activation provided by the incorporation of isopropyl palmitate and butyl stearate, respectively, are illustrated. The antiperspirant composition of Example 10 comprised, in part, 50 centistoke dimethicone (about 38% w/w), isopropyl palmitate (about 9% w/w), disteardimonium hectorite (about 4.25% w/w) and a liquid fragrance material (about 5.5% w/w). The antiperspirant composition of Example 11 comprised, in part, 50 centistoke dimethicone (about 38% w/w), butyl stearate (about 9% w/w), disteardimonium hectorite (about 4.25% w/w) and a liquid fragrance material (about 5.5% w/w). The antiperspirant composition of Example 10 redispersed well with an average (n=3) of 8 turns, a long term settling height of 14 mm and a short term settling height of 38 mm, which is similar to the settling and redispersion characteristics of Example 8. The antiperspirant composition of Example 11 also redispersed well with an average (n=3) of 9 turns, a long term settling height of 13 mm and a short term settling height of 35 mm, which is also similar to the settling and redispersion characteristics of Example 8. These settling and redispersion characteristics appear to be improved compared to Example 5 and comparable to Example 8.

In contrast, comparative Examples 14 and 15 illustrate the relatively poorer redispersion provided by the incorporation of mineral oil ($\delta_h$=about 0.54, light transmittance values of about 100% at concentrations from 2% and 15% w/w in 50 centistoke dimethicone and about 0.4% at 30% w/w in 50 centistoke dimethicone) and isohexadecane ($\delta_h$=about 0.21, light transmittance values of about 100% at concentrations from 2% to 30% w/w in 50 centistoke dimethicone). Isohexadecane is soluble in 50 centistoke dimethicone across the 2% to 30% w/w concentration range while mineral oil is soluble in 50 centistoke dimethicone at some (lower) concentrations. Both materials have $\delta_h$ values less than 2. The antiperspirant composition of Example 14 comprised, in part, 50 centistoke dimethicone (about 38% w/w), mineral oil (about 9% w/w), disteardimonium hectorite (about 4.25% w/w) and a liquid fragrance material (about 5.5% w/w). The antiperspirant composition of Example 15 comprised, in part, 50 centistoke dimethicone (about 38% w/w), isohexadecane (about 9% w/w), disteardimonium hectorite (about 4.25% w/w) and a liquid fragrance material (about 5.5% w/w). The antiperspirant compositions of Examples 14 and 15 fell off the bottom of the container in clumps and then redispersed with continued shaking, a less than desirable outcome compared to Example 8.

Figure 8:
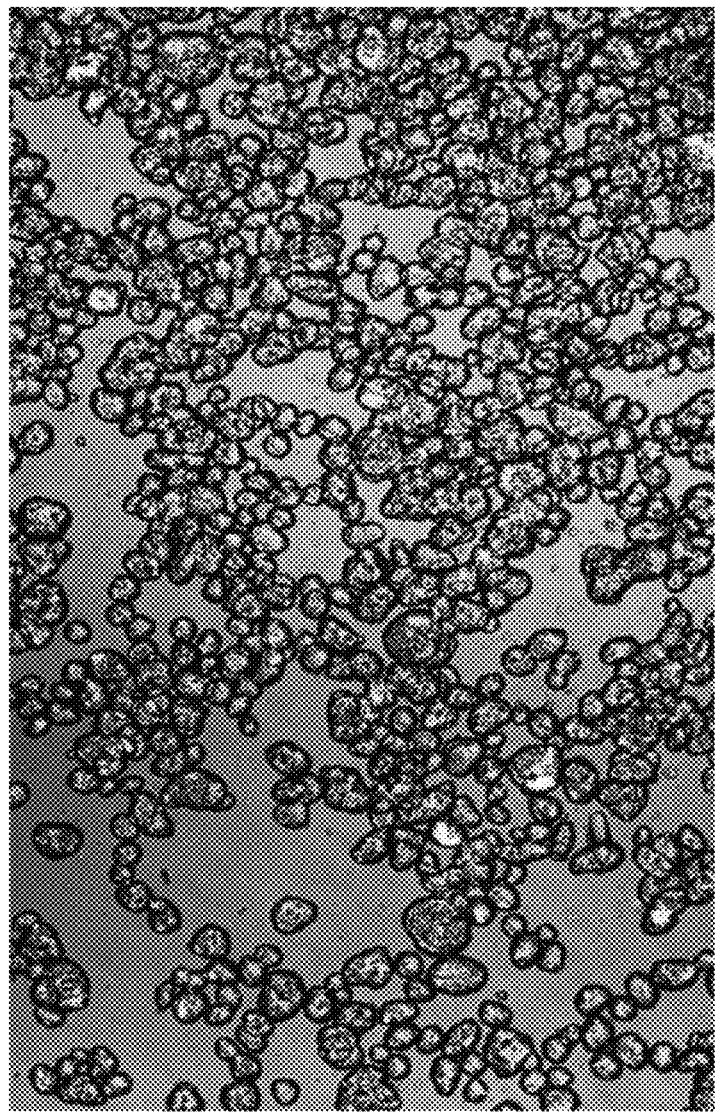
FIG. 8 is a 50× photomicrograph, taken using differential interference contrast, of a composition comprising 50 centistoke dimethicone, disteardimonium hectorite, triethyl citrate, a liquid fragrance material and octyldodecanol.
Figure 9:
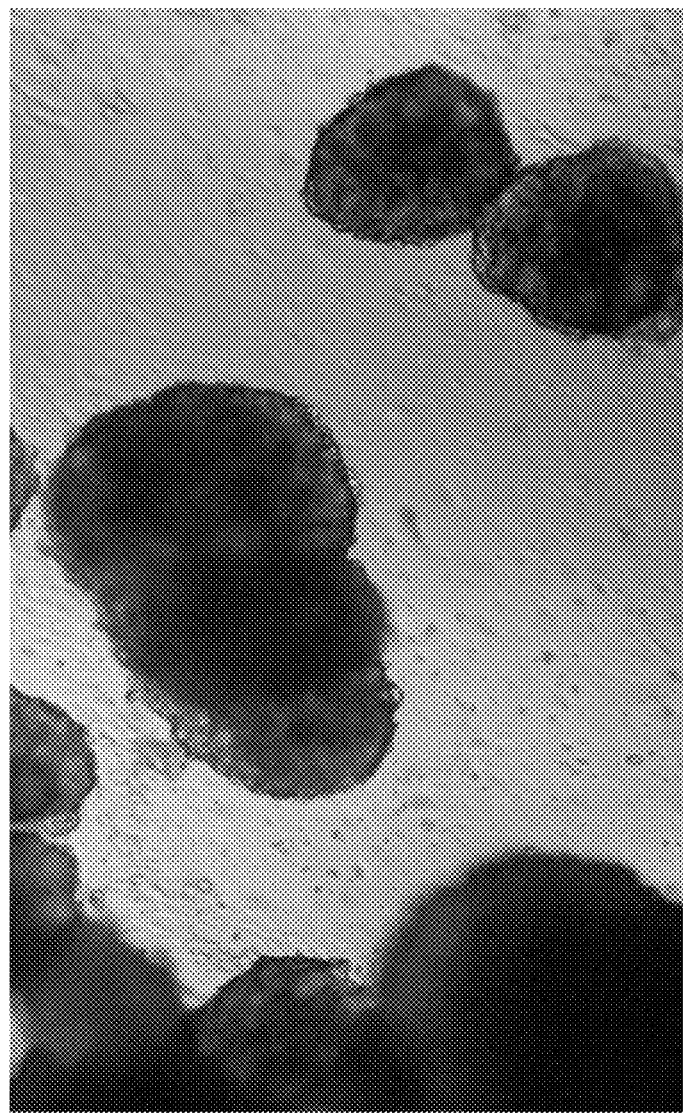
FIG. 9 is a 50× photomicrograph, taken using differential interference contrast, of a composition comprising 50 centistoke dimethicone, disteardimonium hectorite, triethyl citrate, a liquid fragrance material and PPG-14 butyl ether.

Comparative Examples 16 and 17 illustrate the relatively poorer redispersion provided by the incorporation of octyldodecanol ($\delta_h$=about 9.7, light transmittance values of about 100% at 2% w/w concentration in 50 centistoke dimethicone and about 0.8% and about 0.6% at 15% and 30%, respectively, w/w concentration in 50 centistoke dimethicone) and PPG-14 butyl ether ($\delta_h$=about 6.52, light transmittance values of about 15% and about 0.9% at 2% to 30% w/w concentrations in 50 centistoke dimethicone). Both of these materials have $\delta_h$ values greater than 6. Octydodecanol is soluble in the 50 centistoke dimethicone at some (lower) concentrations. PPG-14 butyl ether is insoluble in 50 centistoke dimethicone across the 2% to 30% w/w concentration range. The antiperspirant compositions of Examples 16 and 17 fell off the bottom of the container in clumps and then redispersed with continued shaking, a less than desirable outcome compared to Example 8. In addition, the antiperspirant composition of Examples 16 and 17 appeared grainy and non-homogenous to the naked eye. FIG. 8 is a photomicrograph illustrating the nature of the clay activation in a composition comprising 50 centistoke dimethicone (about 57.4% w/w), disteardimonium hectorite (about 9% w/w), triethyl citrate (about 2.9% w/w), octyldodecanol (about 19% w/w) and a liquid fragrance material (about 11.7%). It is believed that the liquid fragrance material also contained small amounts (about 10% or less by w/w of the liquid fragrance material) of isopropyl myristate as a diluent. In FIG. 8, the clay collapsed into clumps with no fine particles visible. This is arguably worse than shown in FIG. 4, where at least some fine particles are still visible. FIG. 8 is also markedly worse than the composition shown in FIG. 7. FIG. 9 is a photomicrograph illustrating the nature of the clay activation in a composition comprising 50 centistoke dimethicone (about 57.4% w/w), disteardimonium hectorite (about 9% w/w), triethyl citrate (about 2.9% w/w), PPG-14 butyl ether (about 19% w/w) and a liquid fragrance material (about 11.7%). It is believed that the liquid fragrance material also contained small amounts (about 10% or less by w/w of the liquid fragrance material) of isopropyl myristate as a diluent. This composition resulted in macro agglomerates that were visible to the naked eye and no fine particles, again markedly worse than the composition shown in FIG. 7.

Figure 10:
FIG. 10 is a photograph showing three mixtures comprising 50 centistoke dimethicone and C12-15 alkyl benzoate.

Some liquid materials may have a $\delta_h$ between 2 and 6 and straddle the line between soluble and not soluble in the non-volatile silicone fluid, depending on the w/w concentration of the material in the non-volatile silicone fluid and/or the viscosity/molecular weight of the non-volatile silicone fluid. One such material is C12-15 alkyl benzoate ($\delta_h$=about 4.7), available under the trade name Finsolv®. C12-15 alkyl benzoate has light transmittance values of about 101%, about 102%, about 1.4% and about 0.2% at concentrations of 2%, 9%, 15% and 30% w/w, respectively, in 50 centistoke dimethicone. Referring to FIG. 10, four mixtures of 50 centistoke dimethicone and C12-15 alkyl benzoate at 2%, 9%, 15% and 30% w/w concentrations were prepared and are shown in the FIG. 10. The 2% w/w mixture is shown at the far left of FIG. 10 while the 30% w/w mixture is shown at the far right. The 9% and 15% w/w mixtures are shown sequentially to the right of the 2% w/w mixture in FIG. 10. The change in solubility between 9% w/w concentration and 15% w/w concentration is apparent from the change from relatively clear to a more milky appearance of the mixture. Referring to Example 23, an antiperspirant composition comprising, in part, 50 centistoke dimethicone (about 38% w/w), C12-15 alkyl benzoate (about 9% w/w, which would be insoluble in the non-volatile silicone fluid at this concentration), disteardimonium hectorite (about 4.25% w/w) and a liquid fragrance material (about 5.5% w/w) was prepared. The antiperspirant composition exhibited poorer redispersion, with the antiperspirant composition falling off the bottom of the container in clumps.

In some instances, the liquid activation enhancer may also sufficiently activate the organoclay material without the need for a separate clay activator, such as propylene carbonate, triethyl citrate, methanol, ethanol, acetone and mixtures and derivatives thereof. A non-limiting example of one such material is C12-15 alkyl benzoate. Referring to Examples 21 and 22, two antiperspirant composition comprised, in part, 20 centistoke dimethicone and C12-15 alkyl benzoate (9% w/w). The antiperspirant composition of Example 21 comprised triethyl citrate and the antiperspirant composition of Example 22 did not. Both antiperspirant compositions had a powdery redispersion, indicating that the organoclay material was activated in both.

Figure 11:
FIG. 11 is a photograph showing three mixtures comprising 5 centistoke dimethicone and C12-15 alkyl benzoate.
Figure 12:
FIG. 12 is a photograph showing five mixtures comprising 5 centistoke, 10 centistoke, 20 centistoke, 50 centistoke or 350 centistoke dimethicone and C12-15 alkyl benzoate.

It is also believed that the viscosity of the non-volatile silicone fluid may in some instances impact the solubility of the liquid activation enhancer in the non-volatile silicone fluid. In some embodiments, the viscosity of the non-volatile silicone fluid is from about 3 centistokes, 5 centistokes, 10 centistokes, 15 centistokes, 20 centistokes, 50 centistokes and 100 centistokes to about 350 centistokes, 200 centistokes, 100 centistokes or 50 centistokes. Preferably, the viscosity of the non-volatile silicone fluid is from about 5 centistokes to about 100 centistokes, more preferably between about 5 centistokes and about 50 centistokes. In some embodiments, the non-volatile silicone fluid has a viscosity from about 5 centistokes to about 30 centistokes. In contrast to FIG. 10, FIG. 11 illustrates three mixtures of 5 centistoke dimethicone and C12-15 alkyl benzoate at 2%, 15% and 30% w/w concentrations in the dimethicone. The 2% w/w mixture is shown at the far left of FIG. 11 while the 30% w/w mixture is shown at the far right. The 15% w/w mixture is shown in the middle of FIG. 11. All the mixtures were relatively clear, and all of the mixtures have light transmittance values of about 102%. Referring to FIG. 12, four mixtures of 5 centistokes, 10 centistokes, 20 centistokes, 50 centistokes and 350 centistokes dimethicone and C12-15 alkyl benzoate at 15% w/w concentration were prepared. The 5 centistokes mixture is shown at the far left of FIG. 12 while the 350 centistokes mixture is shown at the far right. The 10 centistokes, 20 centistokes and 50 centistokes mixtures are shown sequentially to the left of the 5 centistokes mixture in FIG. 12. The 5 centistokes mixture has a light transmittance value of about 102%, and the 10 centistokes mixture has a light transmittance value of about 100%. The 20 centistokes mixture has a light transmittance value of about 99%, and the 50 centistokes mixture has a light transmittance value of about 1.4%. The 350 centistokes mixture had a light transmittance value of about 0.4%. Referring to Examples 19, 20, 21 and 23, these antiperspirant compositions comprised, in part, C12-15 alkyl benzoate (about 9% w/w) in 5 centistoke dimethicone, 10 centistoke dimethicone, 20 centistoke dimethicone and 50 centistoke dimethicone, respectively. The antiperspirant compositions of Examples 19, 20 and 21 (in which the C12-15 alkyl benzoate was soluble in the non-volatile silicone fluid) exhibited powdery redispersions while the antiperspirant composition of Example 23 (in which the C12-15 alkyl benzoate was not soluble in the non-volatile silicone fluid) fell off the bottom of the container in clumps.

Since both a non-volatile silicone fluid and a liquid fragrance material may negatively affect clay activation, it is believed that the at least one liquid activation enhancer may be most beneficial in those instances where the concentration of the liquid fragrance material exceeds the concentration of the clay material and/or where the concentration of the liquid fragrance material exceeds the concentration of the clay activator. In some embodiments, the ratio of total concentration of non-volatile silicone fluid to the total concentration of liquid activation enhancer is from about 2:1 to about 10:1, or about 3:1 to about 5:1.

F. Order of Addition of the Liquid Fragrance Materials and Non-Volatile Silicone Fluid It is believed that the clay activation and desired bulking benefit may be optionally further improved by controlling the order of addition of the liquid fragrance material and/or the clay material in the making of an antiperspirant composition, particularly at liquid fragrance concentrations greater than 2% by weight of the antiperspirant composition. Without intending to be bound by any theory, it is believed that managing how the liquid fragrance material (particularly those that are highly polar) is added/solubilized may reduce regions of high strong interaction between the liquid fragrance material and the clay material that are believed to result in agglomeration of the clay material and/or precipitation thereof. In one non-limiting embodiment and with reference to FIG. 13, a making and filling process for an antiperspirant composition may comprise a plurality of steps. The first step comprises optionally mixing a first portion of the non-volatile silicone fluid (e.g., 10% to 30% of the total concentration of the final antiperspirant composition) with the clay material and the liquid activation enhancer. The second step comprises adding a clay activator to the mixture of the first step. It will be appreciated that, in some instances, a clay activator may not be needed and this step may be skipped. This is followed by adding a second portion of the non-volatile silicone fluid in a third step, after which the particulates are added in a fourth step to form a first composition. In this embodiment, the first composition is then ready for the filling operation.

In the filling operation, the first composition from the making operation is filled into a reservoir of the spray device, after which the liquid fragrance material is added to the reservoir of the spray device to form the antiperspirant composition. When the liquid fragrance material and the first composition are added separately, as shown by way of example in FIG. 13, there is believed to be little mixing between the liquid fragrance material and the antiperspirant composition due to the large viscosity difference between the two. The valve assembly is then attached to the spray device after which the propellant is added to the reservoir through the valve assembly. Significant mixing of the liquid fragrance material and the first composition is not believed to occur until the addition of the propellant, which beneficially dilutes both the liquid fragrance material and the first composition thereby minimizing regions of high liquid fragrance material concentration that may negatively impact the desired bulking benefit of the clay material. The last step may comprise attaching the actuator to the valve assembly. It will be appreciated that other ingredients may be added to the various mixtures at various points in either the making or filling processes, including after the liquid fragrance material is added to the reservoir if desired.

Figure 13:
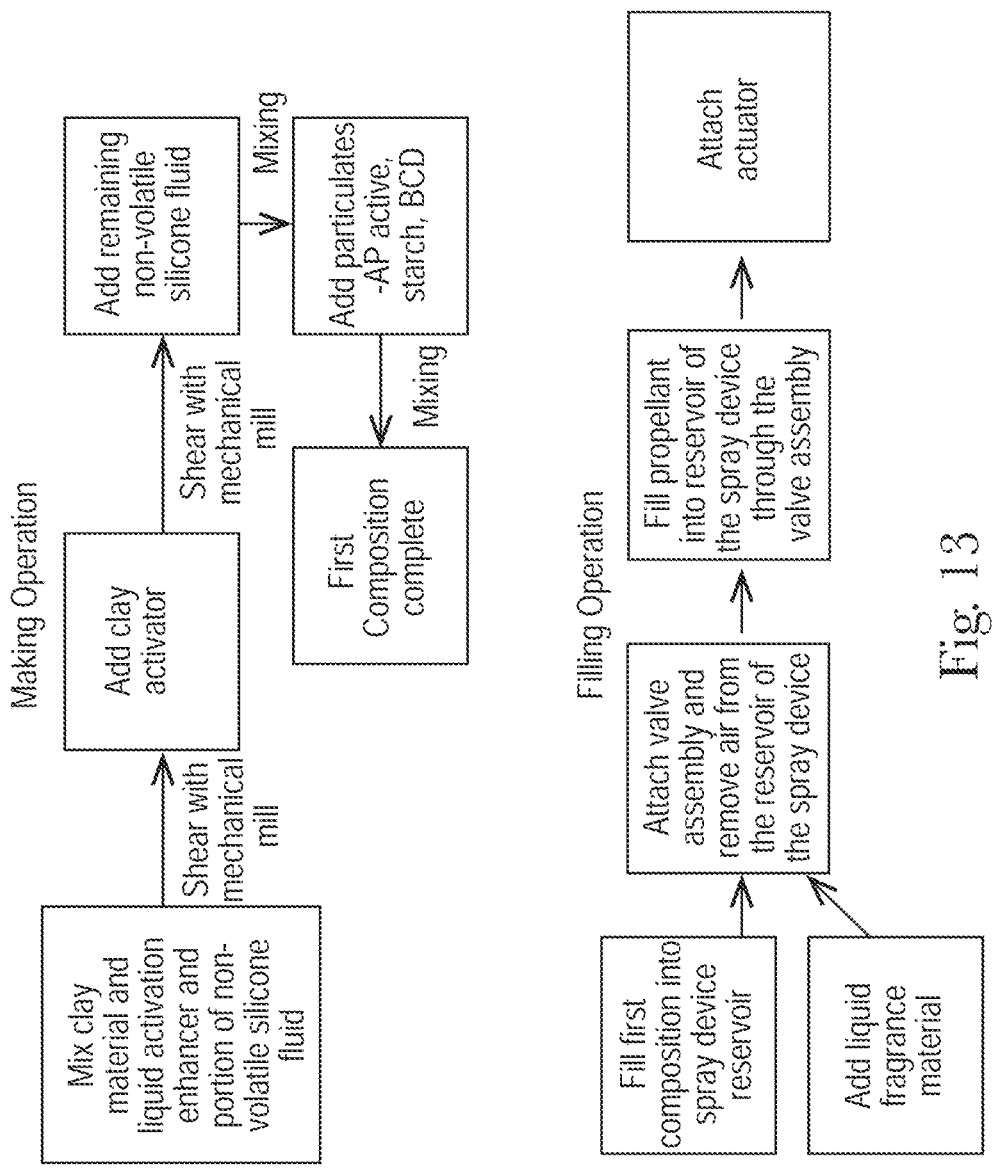
FIG. 13 is a schematic illustration of a non-limiting example for making an antiperspirant composition and the filling thereof into a reservoir.

Examples 3, 6 and 9 were made generally according to the process of FIG. 13. The antiperspirant composition of Example 3 comprised, in part, cyclopentasiloxane (about 47% w/w/), distrearimonium hectorite (about 4.25% w/w), triethyl citrate (about 1.38% w/w) and a liquid fragrance material (about 5.5% w/w). The antiperspirant composition had a powdery redispersion with average number of turns=7.3, a long term settling height of 14 mm and a short term settling height of 39 mm. The antiperspirant composition of Example 6 comprised, in part, 50 centistoke dimethicone (about 47% w/w), disteardimonium hectorite (about 4.25% w/w), triethyl citrate (about 1.38% w/w) and a liquid fragrance material (about 5.5% w/w). The antiperspirant composition had poor redispersion with a majority of the composition still packed on the bottom of the bottle after 5 turns, a longer term settling height of 10 mm and a short term settling height of 21 mm. The antiperspirant composition of Example 9 comprised, in part, 50 centistoke dimethicone (about 38% w/w), isopropyl myristate (about 9% w/w), distrearimonium hectorite (about 4.25% w/w), triethyl citrate (1.38% w/w) and a liquid fragrance material (about 5.5% w/w). The composition had a powdery redispersion with an average number of turns=8, a long term settling height of 15 mm and a short term settling height of 40 mm. Notably, Example 9 appears to result in redispersion and settling characteristics comparable to Example 3 and improved versus Example 6.

Figure 14:
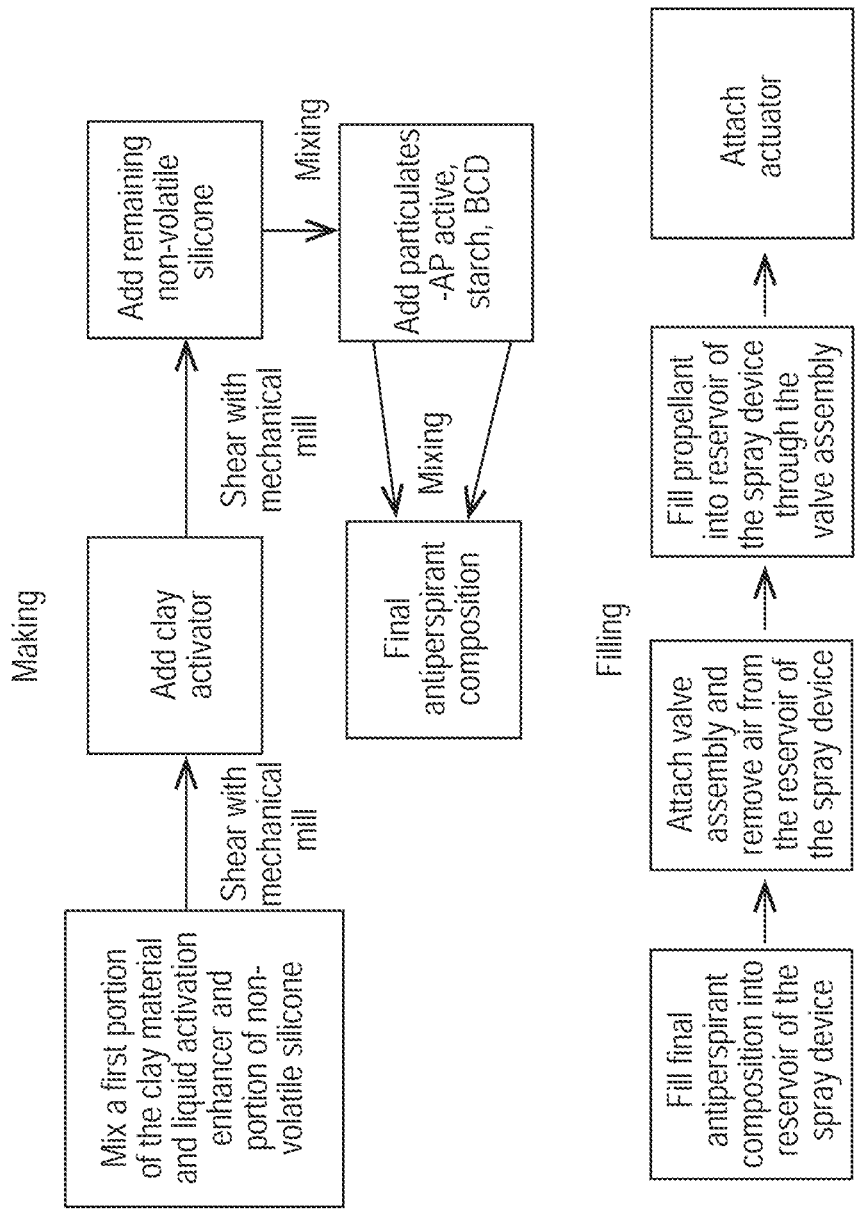
FIG. 14 is a schematic illustration of another non-limiting example for making an antiperspirant composition and the filling thereof into a reservoir.

In another non-limiting embodiment and with reference to FIG. 14, a making and filling process for an antiperspirant composition may comprise a plurality of steps. The first step comprises optionally mixing a first portion of the non-volatile silicone fluid (e.g., 10% to 30% of the total concentration of the final antiperspirant composition) with the clay material and the liquid activation enhancer. In some embodiments, the amount of clay material added in the first step is from about 50%, 60% or 70% to about 80% of the total amount of clay material in the final antiperspirant composition post filling. In these embodiments, from about 2.3% to about 3.75% of the clay material, by weight of the antiperspirant composition post filling, is added in the first step. The second step comprises adding a clay activator to the mixture of the first step. It will be appreciated that, in some instances, a clay activator may not be needed and this step may be skipped. This is followed by adding a second portion of the non-volatile silicone fluid in a third step, after which the particulates together with a liquid fragrance material and a second portion of the clay material (the liquid fragrance material and the second portion of the clay material having been pre-mixed) are added in a fourth step to form the antiperspirant composition. Without intending to be bound by any theory, it is believed that the perfume components of the liquid fragrance material that strongly interact with the second portion of the clay material may do so prior to mixing into the final antiperspirant composition and separate from the first portion of the clay material that was activated previously. It is believed that the bulking and suspending benefit provided by the first portion of the clay material may not be significantly diminished. In this embodiment, the final antiperspirant composition is then ready for the filling operation. In the filling operation, the final antiperspirant composition from the making operation is filled into a reservoir of the spray device. The last step may comprise attaching the actuator to the valve assembly. It will be appreciated that other ingredients may be added to the various mixtures at various points in either the making or filling processes if desired.

Example 24 was made generally according to the process of FIG. 14. The antiperspirant composition of Example 24 comprised, in part, 50 centistoke dimethicone (about 38% w/w/), distrearimonium hectorite (about 4.25% w/w), triethyl citrate (about 1.38% w/w) and a liquid fragrance material (about 5.5% w/w). The antiperspirant composition had a powdery redispersion with average number of turns=6, a long term settling height of 12 mm and a short term settling height of 31 mm.

Figure 15:
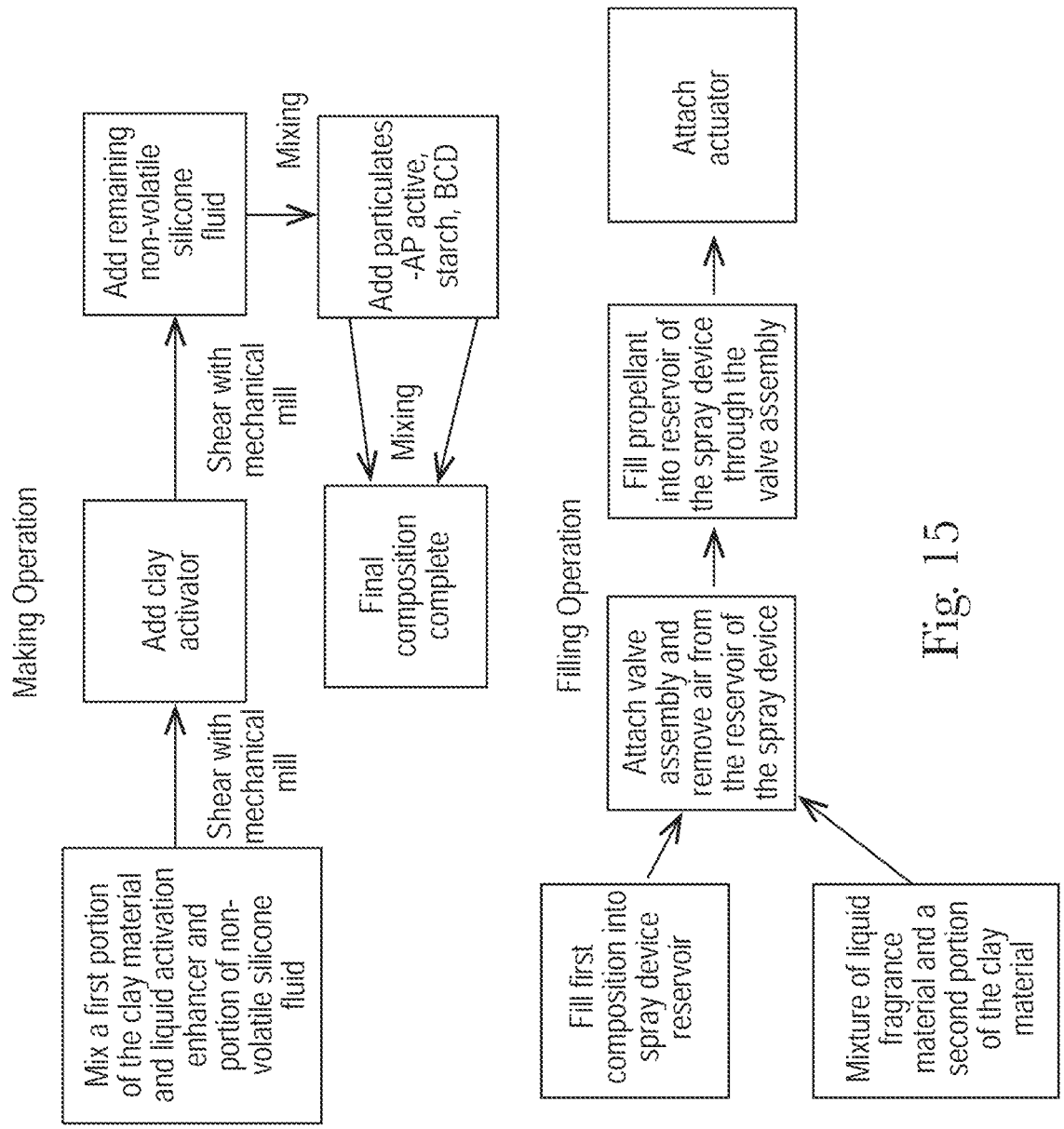
FIG. 15 is a schematic illustration of yet another non-limiting example for making an antiperspirant composition and the filling thereof into a reservoir.

In yet another non-limiting embodiment and with reference to FIG. 15, a making and filling process for an antiperspirant composition may comprise a plurality of steps. The first step comprises mixing a first portion of the clay material and optionally a first portion of the non-volatile silicone fluid (e.g., 10% to 35% of the total concentration) together with a liquid activation enhancer. The clay activator may be added as second step followed by a second portion of the non-volatile silicone fluid as a third step. It will be appreciated that, in some instances, a clay activator may not be needed and this step may be skipped. The particulates are added as a fourth step to form a first composition. In this embodiment, the first composition is then ready for the filling operation. In some embodiments, the amount of clay material added in the making process is from about 50%, 60% or 70% to about 80% of the total amount of clay material in the final antiperspirant composition post filling. In these embodiments, from about 2.3% to about 3.75% of the clay material, by weight of the antiperspirant composition post filling, is added during the making process.

In the filling operation, the first composition from the making operation is filled into a reservoir of the spray device, after which the liquid fragrance material together with a second portion of the clay material (the liquid fragrance material and the second portion of the clay material having been premixed) are added to the reservoir of the spray device to form the antiperspirant composition. The second portion of the clay material and the liquid fragrance material are milled prior to adding to the reservoir as part of the filling operation. Without intending to be bound by any theory, it is believed that the perfume components of the liquid fragrance material that strongly interact with the second portion of the clay material may do so prior to filling the reservoir and separate from the first portion of the clay material that was activated as part of the making process. It is believed that the bulking and suspending benefit provided by the first portion of the clay material activated as part of the making process may not be significantly diminished. The valve assembly is then attached to the spray device after which the propellant is added to the reservoir thru the valve assembly. The last step may comprise attaching the actuator to the valve assembly. It will be appreciated that other ingredients may be added to the various mixtures at various points in either the making or filling processes if desired.

The final antiperspirant compositions described in this Section F may have the same concentrations of ingredients, post filling (meaning after all filling steps are complete), as otherwise described for antiperspirant compositions throughout this specification.

G. Particulate Materials

In one embodiment while the combination of low propellant concentration and a high concentration of non-volatile silicone fluids may provide a number of benefits, this combination may also involve a number of tradeoffs. For example, higher antiperspirant active deposition (facilitated by a low propellant concentration) in combination with a high concentration of a non-volatile silicone fluid may result in a wet and/or sticky skin feel. In addition, a non-volatile silicone fluid may tend to impede release of the antiperspirant active more so than a volatile liquid carrier, as a volatile liquid carrier eventually evaporates leaving behind the antiperspirant active and the other non-volatile components, which are easily wetted by perspiration thereby releasing the antiperspirant active. In contrast, non-volatile silicones do not evaporate as easily and tend to be hydrophobic, thereby potentially decreasing antiperspirant active release.

Delivering a sufficient concentration of particulates to the skin is believed to improve the skin feel of an antiperspirant composition comprising a high concentration of a non-volatile silicone fluid. It is believed that an antiperspirant composition comprising a total non-volatile liquid material to total particulate material ratio (L/P ratio) from about 0.6, 0.8, 1, 1.2, or 1.4 to about 2.3, 2.2, 2.1, 2, 1.9, 1.8 or 1.6 may balance the tradeoff between enough particulates to provide acceptable skin feel while minimizing the appearance of residue. An antiperspirant composition may have a total particulate concentration from about 30%, 35%, or 40% to about 60%, 55%, or 50% by weight of the antiperspirant composition, in keeping with the total liquid to total particulate (L/P) ratios previously described. While increasing the concentration of particulates may improve skin feel, it may also lead to an increased risk of clogging especially at low propellant concentrations.

The antiperspirant composition may comprise a variety of particulate materials. However, it is believed that the type (e.g., hydrophilic v. hydrophobic) and concentrations of particulate materials included in an antiperspirant composition may, in some instances, impact skin feel, release of the antiperspirant active, and the propensity for clogging in the spray device. For example, too much antiperspirant active may result in a wet or sticky skin feel due to the propensity of antiperspirant actives to become sticky when hydrated (e.g., by perspiration) even within the L/P ratios previously described. In addition, too much of a hydrophobic particulate material may reduce release of the antiperspirant active from the composition. Conversely, inclusion of a hydrophilic particulate material may advantageously aid release of the antiperspirant active, which may be beneficial in a composition comprising a high concentration of a non-volatile silicone fluid. However, hydrophilic materials may increase the risk of clogging in the presence of water. Therefore, it may be desirable to balance these and other design considerations when incorporating particulate materials in an antiperspirant composition comprising a non-volatile silicone fluid that is in turn used in a spray device especially those with low propellant concentration.

Some examples of particulate materials include, but are not limited to, antiperspirant actives, powders (e.g., starch materials), encapsulated fragrance materials and bulking or suspending agents (e.g., clay materials). Other types of particulates may also be incorporated in an antiperspirant composition.

Antiperspirant Actives

An antiperspirant composition comprises one or more antiperspirant actives. The antiperspirant active may be any particle having antiperspirant activity. The antiperspirant active is preferably insoluble in the liquid components of the antiperspirant composition. Since the amount of antiperspirant active may significantly impact skin feel, an antiperspirant composition may comprise from about 14% 16%, 18%, 20%, 22%, or 24% to about 38%, 36%, 34%, 32%, 30%, 28%, or 26% by weight of a particulate antiperspirant active. In some instances, it may be desirable to utilize a low concentration of the antiperspirant active, such as less than 20% or 18% by weight of the antiperspirant composition. The antiperspirant active concentrations refer to the anhydrous amount that is added. The antiperspirant active may represent the highest concentration of particulate materials in the antiperspirant composition. For example, the antiperspirant active (on an anhydrous basis) may comprise from about 50% to about 80%, or from about 50% to about 75%, or from about 55% to about 70% of the total particulate materials in the antiperspirant composition. The balance of the total particulate concentration comprises non-antiperspirant active particulates.

Some examples of suitable antiperspirant actives include astringent metallic salts, particularly including the inorganic and organic salts of aluminum. Some non-limiting examples exemplary aluminum salts that can be used include aluminum chloride and the aluminum hydroxyhalides having the general formula $Al_2(OH)_aQ_b \cdot XH_2O$ where Q is chloride, bromide, or iodide (preferably chloride), a is from about 2 to about 5, and a+b=about 6, and a and b do not need to be integers, and where X is from about I to about 6, and X does not need to be an integer. Particularly preferred are the aluminum chlorhydroxides referred to as "5/6 basic chlorhydroxide" wherein "a" is 5 and "2/3 basic chlorhydroxide" wherein "a" is 4. Aluminum salts of this type can be prepared in the manner described more fully in U.S. Pat. Nos. 3,887,692; 3,904,741; and 4,359,456. Preferred compounds include the 5/6 basic aluminum salts of the empirical formula $Al_2(OH)_5D \cdot I2H_2O$; mixtures of $AlCl_3 \cdot 6H_2O$ and $Al_2(OH)5Cl_2H_2O$ with aluminum chloride to aluminum hydroxychloride weight ratios of up to about 0.5.

The aluminum salt may be prepared by methods well known in the art. In some embodiments, the aluminum salts may be made by applying heat to a dilute aqueous solution of an aluminum salt (e.g., less than 20% of an aluminum salt by weight of the dilute solution) to form a solid aluminum salt comprising aluminum hydrolysis polymers. Some non-limiting examples of such methods are described in U.S. Pat. Nos. 4,871,525 and 4,359,456.

Substantially Inert Particulate Materials

The balance of the total particulate concentration of an antiperspirant composition may comprise excipient particulate materials that are substantially inert with respect to the non-volatile silicone fluid. The excipient particulate materials may be either hydrophilic or hydrophobic (including hydrophobically modified, which tend to be moderately hydrophobic). Some non-limiting examples of substantially inert excipient particulate materials that may be included in an antiperspirant composition include, but are not limited to, encapsulated fragrance materials; native starches such as tapioca, corn, oat, potato, and wheat starch particulates; talc; calcium carbonate; perlite; mica and polyethylene beads.

The substantially inert particulates may be free flowing. An antiperspirant composition may comprise from about 0.25%, 0.5%, 1%, 5%, 10%, 12%, or 14% to about 25%, 22%, 20%, 18%, or 16% by weight of the antiperspirant composition of substantially inert particulates.

One substantially inert particulate material believed to be suitable for use is a hydrophilic or hydrophobically modified tapioca material. A tapioca material may be particularly beneficial as it is unlikely to induce an allergic reaction if inhaled. Tapioca is a starch which may be extracted from the cassava plant, typically from the root, which may then be processed or modified as known in the art. Tapioca starches are, advantageously, substantially non-allergenic. One non-limiting example of a hydrophobically modified tapioca material suitable for use comprises a silicone grafted tapioca starch, which is available under the trade name Dry Flo TS from AkzoNobel of the Netherlands. The INCI name is tapioca starch polymethylsilsesquioxane and may be produced by a reaction of methyl sodium siliconate (polymethylsilsesquioxane) and tapioca starch. This silicone grafted tapioca material is commercially available as CAS No. 68989-12-8. The silicone grafted tapioca material can be formed using any known means, including, but not limited to those methods described in U.S. Pat. Nos. 7,375,214, 7,799,909, 6,037,466, 2,852,404, 5,672,699, and 5,776,476. Other non-limiting examples of hydrophobically modified tapioca materials that are suitable for use include Dry Flo AF (silicone modified starch from Akzo Nobel), Rheoplus PC 541 (Siam Modified Starch), Acistar RT starch (available from Cargill) and Lorenz 325, Lorenz 326, and Lorenz 810 (available from Lorenz of Brazil). In some specific embodiments, the tapioca material may be hydrophilic in order to facilitate release of the antiperspirant active during use. One non-limiting example of a hydrophilic tapioca material suitable for use is available under the trade name Tapioca Pure available from Akzo Nobel. In some specific embodiments, the substantially inert particulate material comprises a hydrophilic tapioca material, a hydrophobic tapioca material or a mixture thereof.

An antiperspirant composition may optionally comprise one or more particulate fragrance carriers. Fragrance carriers are typically particulates, which would be considered part of the total particulate concentration of the antiperspirant composition. The fragrance carriers are preferably hydrophobic in order to minimize particle-to-particle interactions. The fragrance carriers may be either full or empty. A full fragrance carrier is a fragrance carrier that encapsulates or otherwise contains a perfume component while the fragrance carrier is stored within the spray device. Full fragrance carriers may release their perfume components by a variety of mechanisms post delivery from the spray device to provide a desired aroma or fragrance experience for a user. For example, the perfume components may be released by moisture upon wetting of the fragrance carrier, e.g., by perspiration or other body fluids. Alternatively or in addition thereto, the perfume components may be released by fracture of the carrier, such as by the application of pressure or a shearing force. An empty fragrance carrier is a fragrance carrier that does not contain a perfume component while stored within the spray device. One non-limiting example of an empty fragrance carrier is an uncomplexed cyclodextrin material.

Some non-limiting examples of fragrance carriers suitable for encapsulating a perfume component include, but are not limited to, oligosaccharides (e.g., cyclodextrins), starches, polyethylenes, polyamides, polystyrenes, polyisoprenes, polycarbonates, polyesters, polyacrylates, vinyl polymers, silicas, and aluminosilicates. Some examples of fragrance carriers are described in USPNs 2010/0104611; 2010/0104613; 2010/0104612; 2011/0269658; 2011/0269657; 2011/0268802; U.S. Pat. Nos. 5,861,144; 5,711,941; 8,147,808; and 5,861,144.

An antiperspirant composition may comprise from about 0.25%, 0.5%, 0.75%, 1%, or 2% to about 20%, 16%, 12%, 10%, 8%, 6% or 4% by weight of the antiperspirant composition of fragrance carriers. In some instances, the substantially inert excipient particles of the antiperspirant composition consist essentially of or completely of full fragrance carriers, empty fragrance carrier, or mixtures thereof. An antiperspirant may comprise from about 0.25%, 0.5%, 0.75%, or 1% to about 6%, 4% or 2% by weight of the antiperspirant composition of full fragrance carriers. An antiperspirant composition may comprise from about 0.25%, 0.5%, 1%, or 2% to about 16%, 12%, 10%, 8%, 6% or 4% by weight of the antiperspirant composition of empty fragrance carriers. In some instances, it may be desirable to incorporate a mixture of empty fragrance carriers and full fragrance carriers in the antiperspirant composition, wherein the empty fragrance carriers may be included to achieve the desired overall particulate concentration without the risk of perfume over-dosing.

In some instances, it may be desirable to provide a mixture of fragrance carriers and native starch powders to achieve the desired particle concentration. For example, from about a 20:80 to 80:20 (fragrance carrier to starch) mixture might be utilized. In some instances, a 50:50 mixture might be utilized and in other instances the native starch powders might have a concentration equal to about or less than 6% by weight of the antiperspirant composition while the concentration of the fragrance carriers might be equal to about or less than 9% by weight of the antiperspirant composition.

A wide variety of perfume components may be used with the fragrance carriers, including but not limited to volatile perfume components having a boiling point at normal pressure of less than about 260° C., more preferably less than about 250° C., and perfume components having significant low odor detection threshold, and mixtures thereof. The boiling points of many perfume components are given in, e.g., "Perfume and Flavor Chemicals (Aroma Chemicals)," Steffen Arctander, published by the author, 1969.

H. Other Liquid Materials

While it may be desirable for the liquid materials of the antiperspirant composition to consist essentially of or be primarily formed from non-volatile silicone fluids, the liquid activation enhancer and optionally liquid fragrance materials, it is contemplated that other liquid materials may be optionally included in an antiperspirant composition. The liquid materials of the antiperspirant composition may comprise less than 30%, 20%, 10%, or less than 5% by weight of liquid materials other than non-volatile, silicone fluids. Said in another way, the liquid materials of the antiperspirant composition may comprise more than 70%, 75%, 80%, 85%, 90% or about 100% by weight of non-volatile silicone fluids.

It is believed that an antiperspirant composition whose liquid materials comprise too much of a volatile silicone fluid may lead to an increased propensity for the appearance of a residue due to the evaporation of the volatile silicone fluid. An antiperspirant composition may comprise less than 10%, 5%, 1%, or 0.5% by weight of a volatile silicone fluid. An antiperspirant composition may be substantially or completely free of a volatile silicone fluid.

An antiperspirant composition may optionally comprise one or more silicone gums. A silicone gum may be added to an antiperspirant composition to further increase substantivity of the antiperspirant composition and/or increase the drop size of the aerosol spray particles and/or increase deposition on the skin. However, formulating an antiperspirant composition with a silicone gum in combination with relatively high concentrations of a non-volatile silicone fluid and/or relatively high concentrations of total particulates may involve a number of tradeoffs. For example, too much of a silicone gum may dramatically increase viscosity of the antiperspirant composition and the risk of clogging of the container actuator and/or valve, particularly where there is already a relatively high concentration of total particulates. Furthermore, too much of a silicone gum may reduce the diameter of the spray making it more difficult for a user to achieve complete coverage of an axillia (typically a 7.5 cm×12.5 cm area) during application as well as potentially creating regions of high antiperspirant composition dosage, thereby negatively impacting skin feel. Still further, the amount of gum required to control the deposition on skin and diameter of the spray pattern is dependent on the level and/or type of propellant, with the amount needed generally increasing as the propellant level and pressure increases.

Given the one or more potential challenges associated with incorporating a silicone gum, an antiperspirant composition may be substantially or completely free of silicone gum materials. When inclusion of a silicone gum is desirable for antiperspirant products with less than about 70% propellant, an antiperspirant composition may have a concentration from about 0.05% or 0.075% to about 0.75%, 0.5%, 0.4%, 0.3%, or 0.2% of a silicone gum by weight of the antiperspirant composition. When inclusion of a silicone gum is desirable for antiperspirant products with more than about 70% propellant, an antiperspirant composition may have a concentration from about 0.3% or 0.5% to about 3.0%, 2.5%, 2%, 1.5%, or 1.2% of a silicone gum by weight of the antiperspirant composition. The silicone gum material may have a viscosity from about 100,000 centistokes to about 10,000,000 centistokes at 25° C.

If a silicone gum is included, any silicone gum having a viscosity within the ranges described herein may be used, provided it is soluble in the liquid carrier, propellant or a combination thereof of the antiperspirant composition. Some suitable silicone gums include silicone polymers of the dimethyl polysiloxane type, which may have other groups attached, such as phenyl, vinyl, cyano, or acrylic, but the methyl groups should be in a major proportion. Silicone polymers having a viscosity below about 100,000 centistokes (molecular weight below about 100,000) at 25° C. are not considered silicone gums here but are rather, typically, considered a silicone fluid. One non-limiting example of silicone gum suitable for use is a silicone/gum fluid blend comprising a dimethiconol gum having a molecular weight form about 200,000 to 4,000,000 along with a silicone fluid carrier with a viscosity from about 0.65 to 100 mm$^2$ s$^{-1}$. An example of this silicone/gum blend is available from Dow Corning, Corp. of Michigan, USA under the trade name DC-1503 Fluid or XIAMETER® PMX-1503 FLUID (85% dimethicone fluid/15% dimethiconol). Other silicone gums materials include SF1236 Dimethicone, SF1276 Dimethicone, and CF1251 Dimethicone available from Momentive Performance Materials, Inc. of NY, USA.

An antiperspirant composition is preferably substantially or completely free of water added as separate ingredient (i.e., anhydrous), as too much added water may result in several deleterious effects such as: 1) increasing the propensity for antiperspirant active particulates to agglomerate (thereby increasing the propensity for clogging), and 2) reducing dry feel on skin. It will be appreciated that even an anhydrous antiperspirant composition may still contain some water that is bound with an ingredient (e.g., antiperspirant active, tapioca material, etc.) otherwise added to the antiperspirant composition.

III. Spray Devices

As discussed above, there may be a variety of benefits and tradeoffs associated with combining lower vs. higher propellant concentrations with an antiperspirant composition comprising a non-volatile silicone fluid. For example reducing propellant concentration may increase the amount of antiperspirant active and/or fragrance materials that are deposited on skin while enabling a more compact spray device. Regardless of the level of propellant incorporating a non-volatile silicone fluid may improve antiperspirant active substantivity on the skin. This may lead to an increase in antiperspirant efficacy or, alternatively, may permit lower concentrations of antiperspirant active to be employed in an antiperspirant composition while still achieving comparable antiperspirant efficacy.

However, incorporating a non-volatile silicone fluid can lead to a wet feeling in use, which may be disliked by some consumers. To compensate, sufficient particulate concentrations may improve skin feel to a point. However, a decrease in propellant concentration provides less dilution of the antiperspirant composition and may necessitate reducing some flow areas within the spray device to limit the mass flows and avoid over-dosing of the antiperspirant composition. Reducing spray device flow areas may increase the risk of clogging.

In one embodiment in order to avoid over-dosing of the antiperspirant composition, for propellant concentrations from about 30% to about 70%, by weight of total fill of material, it is desirable that the spray device have a total mass flow rate of the propellant/antiperspirant composition mixture of less than 0.5 grams/sec or from about 0.1 grams/sec to about 0.6 grams/sec, or from about 0.2 grams/sec to about 0.4 grams/sec, or from about 0.25 grams/sec to about 0.35 grams/sec. In another embodiment for higher propellant concentrations, e.g from about 70% to about 90%, or from about 75% to about 90% by weight of total fill of material, in order to avoid over-dosing of the antiperspirant composition, it is desirable that the spray device have a total mass flow rate of the propellant/antiperspirant composition mixture of less than 1.5 grams/sec or from about 0.5 grams/sec to about 1.25 grams/sec, or from about 0.7 grams/sec to about 1.1 grams/sec, or from about 0.8 grams/sec to about 1.0 grams/sec. The spray device may have an antiperspirant composition mass flow rate less than 0.3 grams/sec or from about 0.1 grams/sec to about 0.3 grams/sec or from about 0.1 grams/sec to 0.2 grams/sec or from about 0.15 grams/sec to about 0.2 grams/sec. It is believed that mass flow rates greater than described above may lead to a wet or sticky skin feel (even if the L/P ratio is within the ranges previously described), because the total amount of antiperspirant composition deposited on the skin may be too great.

The amount of antiperspirant active delivered to a target surface by a two second application from a spray device may be from about 40 mg, 50 mg, 60 mg, or 70 mg to about 110 mg, 100 mg, 90 mg, or 80 mg. The total amount of antiperspirant composition delivered to a target surface by a two second application of a spray device may be from about 0.1 grams to about 0.4 grams, or from about 0.2 grams to about 0.4 grams, or from about 0.2 grams to about 0.3 grams. The amount of liquid fragrance material delivered to a target surface by a two second application of a spray device may be from about 3 mg to about 20 mg, or from about 6 mg to about 15 mg, or from about 6 mg to about 12 mg. The amount of full fragrance carriers delivered to a target surface by a two second application of a spray device may be from about 0.75 mg to about 15 mg, or from about 1 mg to about 12 mg, or from about 1 mg to about 9 mg. The spray device may have a deposition efficiency, of either the antiperspirant composition and/or the antiperspirant active, that is from about 70% or 80% to about 95% or 90%.

Figure 16:
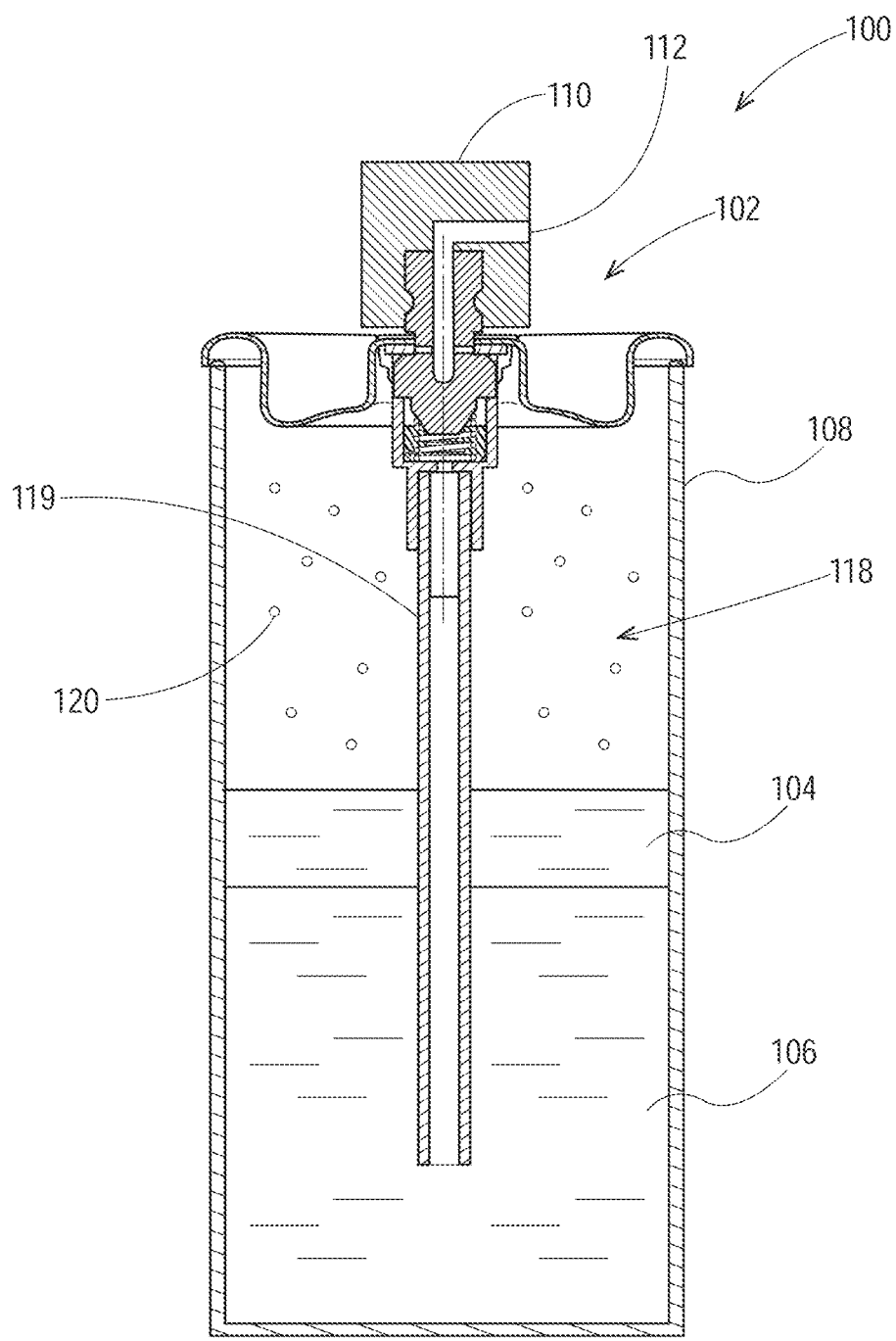
FIG. 16 is a cross-sectional side view of one non-limiting example of a novel spray device comprising an actuator, a valve assembly and a reservoir containing a liquid propellant, a gaseous propellant and an antiperspirant composition.

Referring to FIG. 16, one non-limiting example of a spray device that may help reduce clogging in some instances is shown. While it may be desirable to use the spray device shown in FIG. 16 to reduce the risk of clogging in some instances, it will be appreciated that other spray devices, including other types of actuators and valve assemblies, etc., may also be used with the antiperspirant compositions and propellants described herein. The spray device 100 comprises a container 102, a liquid propellant 104 and an antiperspirant composition 106. It will be appreciated that the propellant 104 and antiperspirant composition 106 are merely shown for purposes of illustration in FIG. 16, and FIG. 16 is not intended to limit in any way the type or arrangement of the propellant and antiperspirant composition within the container 102. For example, in some instances the propellant and the composition are miscible such that distinct layers may not be visible. The spray device 100 may be shaped and configured so that it is handholdable. The container 102 comprises a body 108, an actuator 110 having an actuator orifice 112, and a valve assembly 114 in fluid communication with a reservoir 118 storing the composition 106 and liquid propellant 104. The reservoir 118 may be defined by one or more interior surfaces of the body 108. The reservoir may have a volume from about 20 ml, 40 ml, or 60 ml to about 120 ml, 110 ml, 100 ml, or 90 ml. A dip tube 119 may extend into the reservoir 118 from the valve assembly 114. A gaseous propellant 120 may fill the headspace of the reservoir 118.

Figure 17:
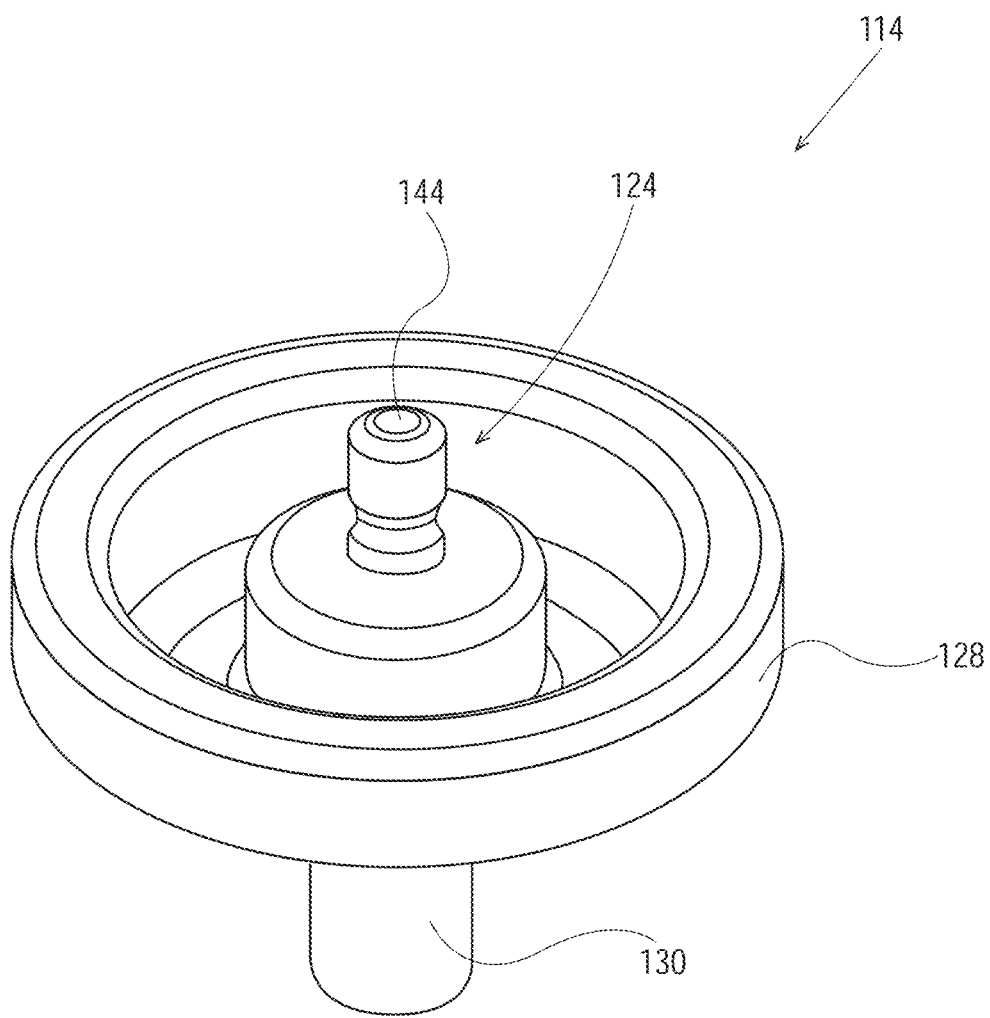
FIG. 17 is a perspective view of the valve assembly of FIG. 16.
Figure 18:
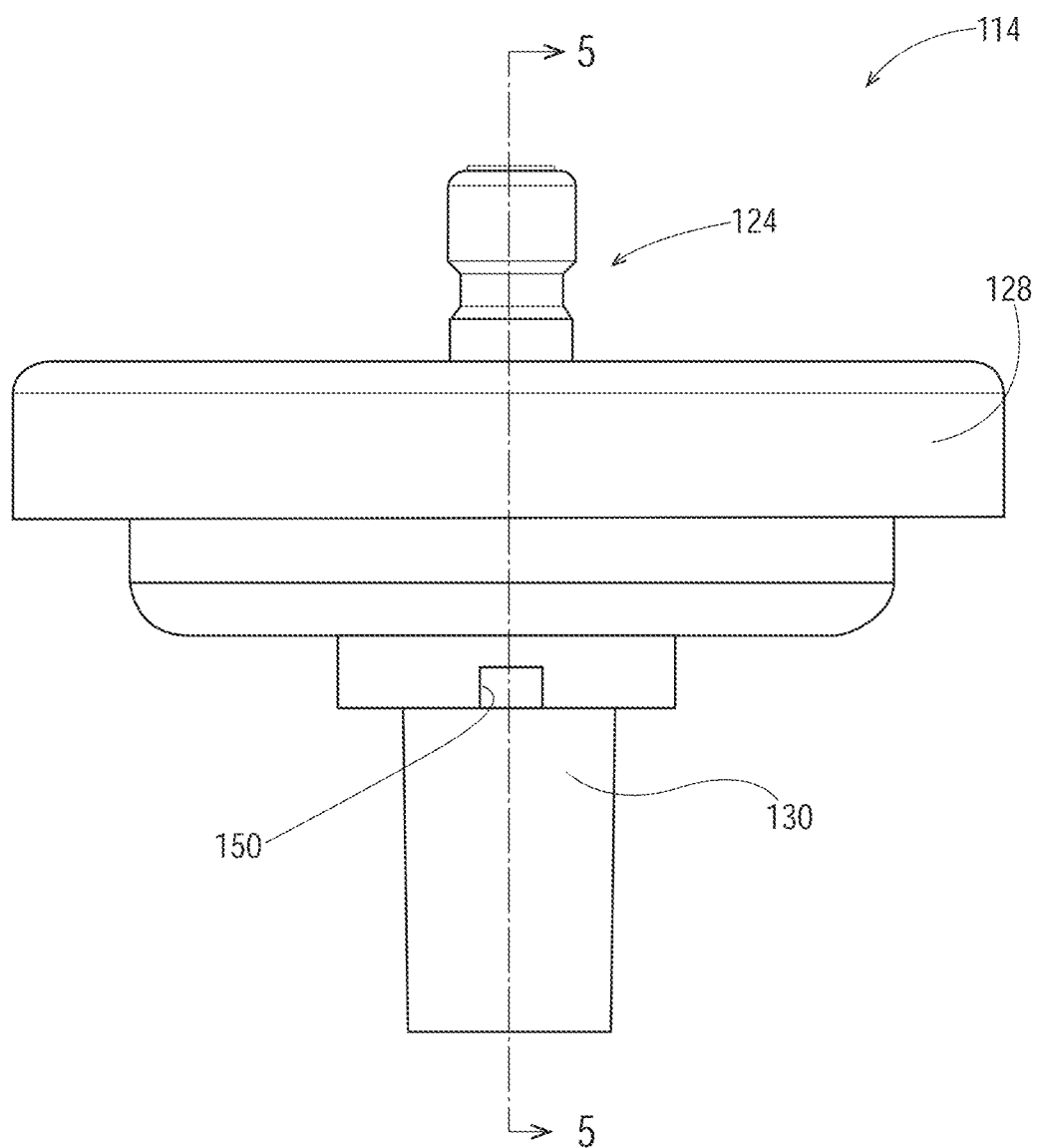
FIG. 18 is a side elevation view of the valve assembly of FIG. 17.
Figure 19:
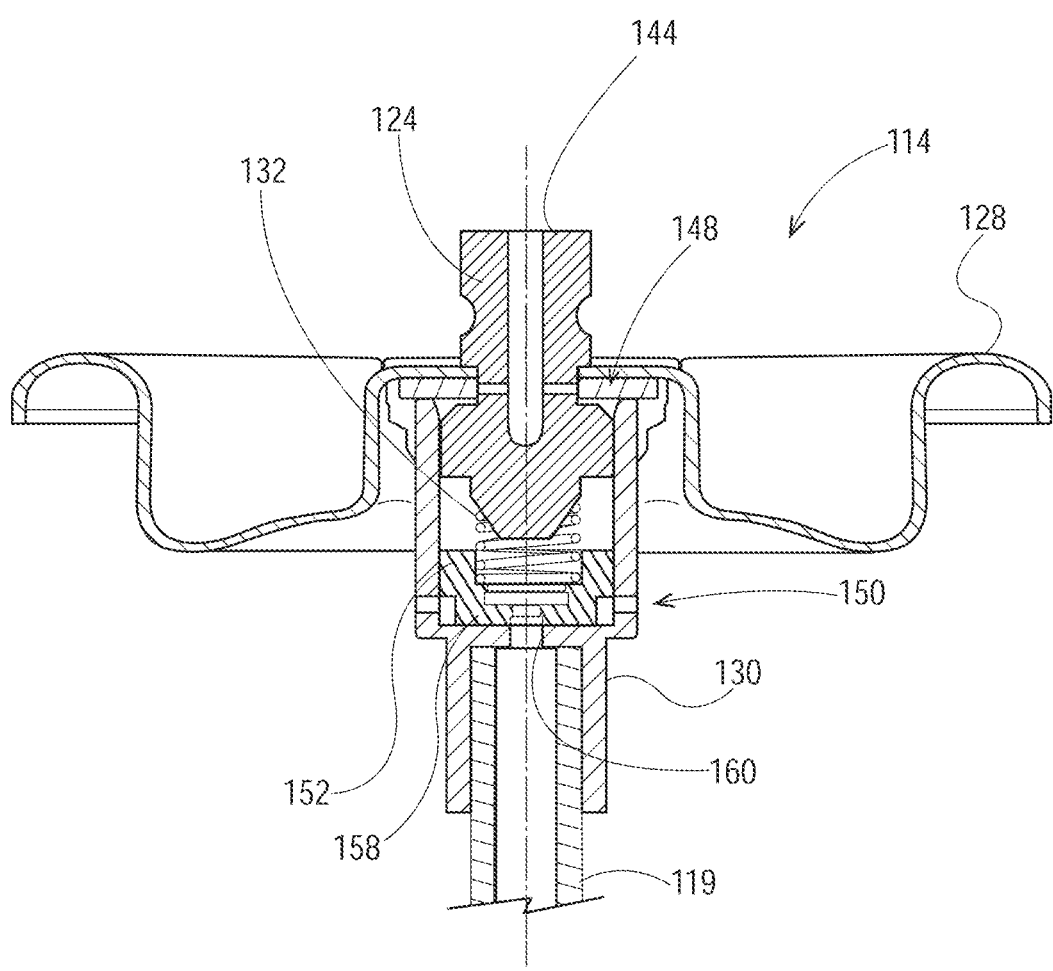
FIG. 19 is a cross-sectional view of the valve assembly of FIG. 18, taken along 5-5 thereof.

Referring to FIGS. 17 to 19, one non-limiting example of a valve assembly 114 which may be attached to the body 108 is shown. The valve assembly 114 comprises a slidably disposed valve stem 124 to which the actuator 110 attaches, a mounting flange 128 for attaching the valve assembly 114 to the body 108 (such as by crimping), and a housing 130 attached to the mounting flange 128. The valve assembly 114 also has an axial bore 144. The housing 130 may be attached by a variety of means to the mounting flange, as known in the art, including by a press fit, positive latching, welding, etc. The housing 130 contains a spring 132 that biases the valve stem 124. The spring 132 may comprise a plurality of coils.

Figure 20:
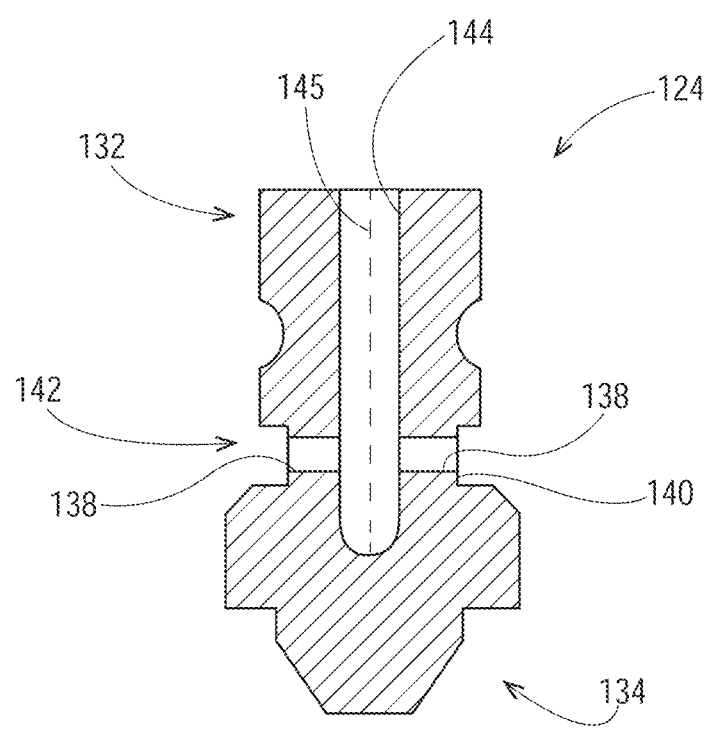
FIG. 20 is cross-sectional side elevation view of the valve stem of FIG. 19.

Turning to FIG. 20, the valve stem 124 comprises an upper portion 132 and a lower portion 134. The upper portion 132 has a distal end 136 and is configured to be attachable to the actuator 110. The lower portion 134 is configured to position at least a portion of the spring 132 there about. One or more valve stem orifices 138 (two being shown in the Figures) are disposed between the upper portion 132 and the lower portion 134. The valve stem orifices 138 are arranged in a radial direction with respect to the longitudinal axis 145 of the valve stem 124. The two or more valve stem orifices 138 open into a wall 140 of a groove 142 and communicate with an axial bore 144 that extends from the two or more valve stem orifices 138 to the distal end 136 of the upper portion 132. It will be appreciated that the terms "radial" and "axial", and derivatives thereof (e.g., radially and axially), are intended to merely refer to a general direction with respect to a feature or structure, and these terms are intended, unless expressly stated otherwise (e.g., solely axial or solely radial), to be fully inclusive of directions that are not purely radial or axial, such as substantially radial/axial directions and combinations of radial and axial directions where the net overall directional effect is more radial than axial or vice versa. The axial bore 144 in turn communicates with the actuator 110 when it is attached to the valve stem 124.

Figure 21:
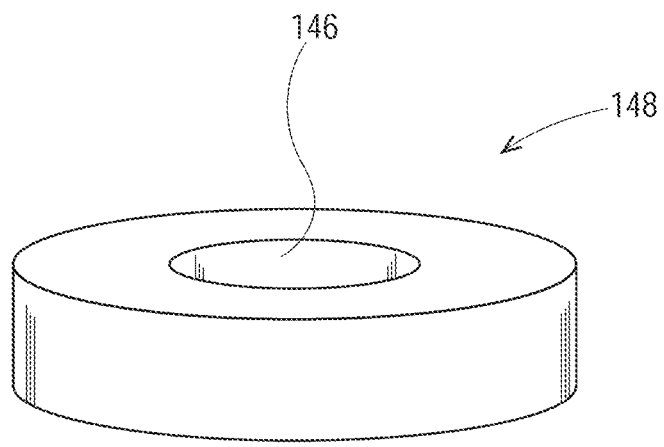
FIG. 21 is a perspective view of the seal of FIG. 19.
Figure 22:
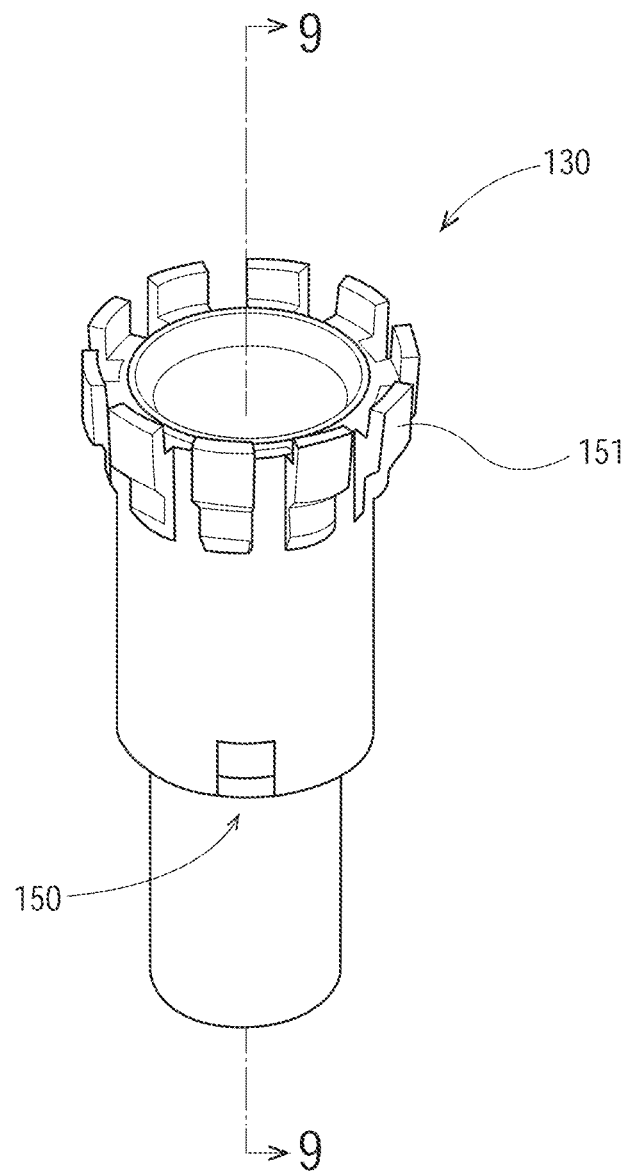
FIG. 22 is a perspective view of the housing of FIG. 19.
Figure 23:
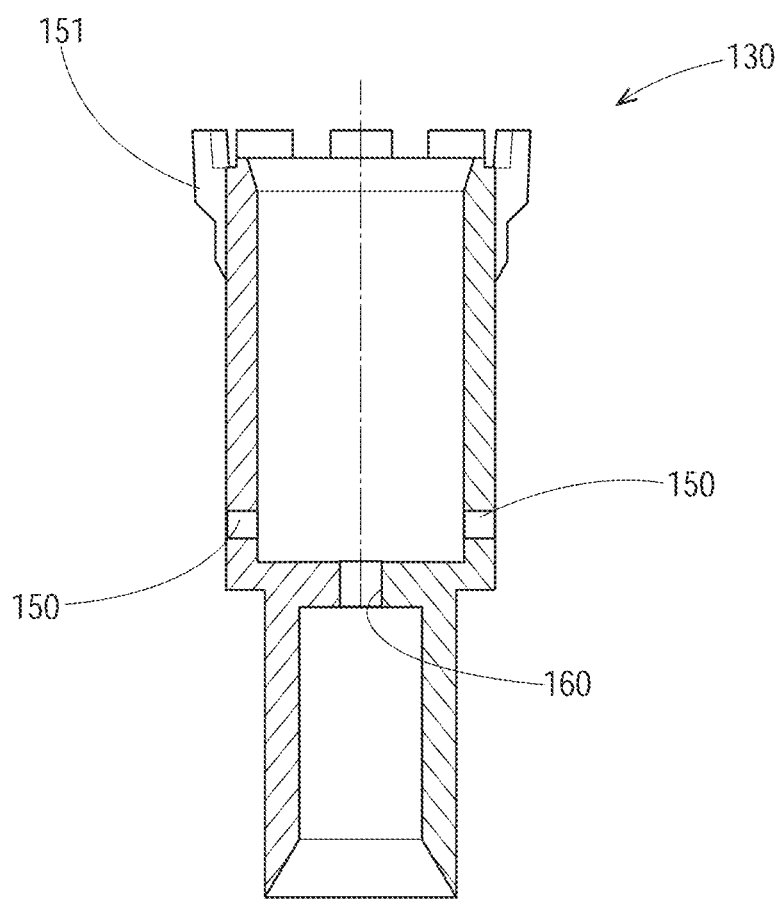
FIG. 23 is a cross-sectional side elevation view of the housing of FIG. 22, taken along line 9-9 thereof.
Figure 24:
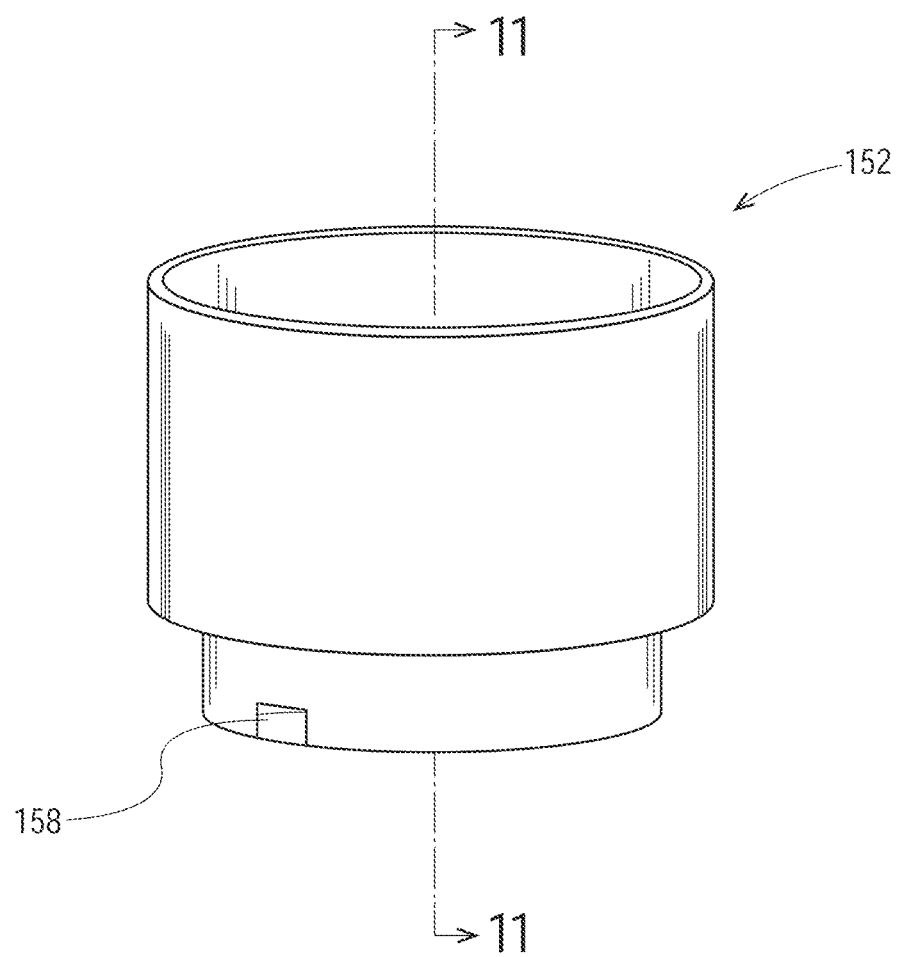
FIG. 24 is a perspective view of the insert of FIG. 19.
Figure 25:
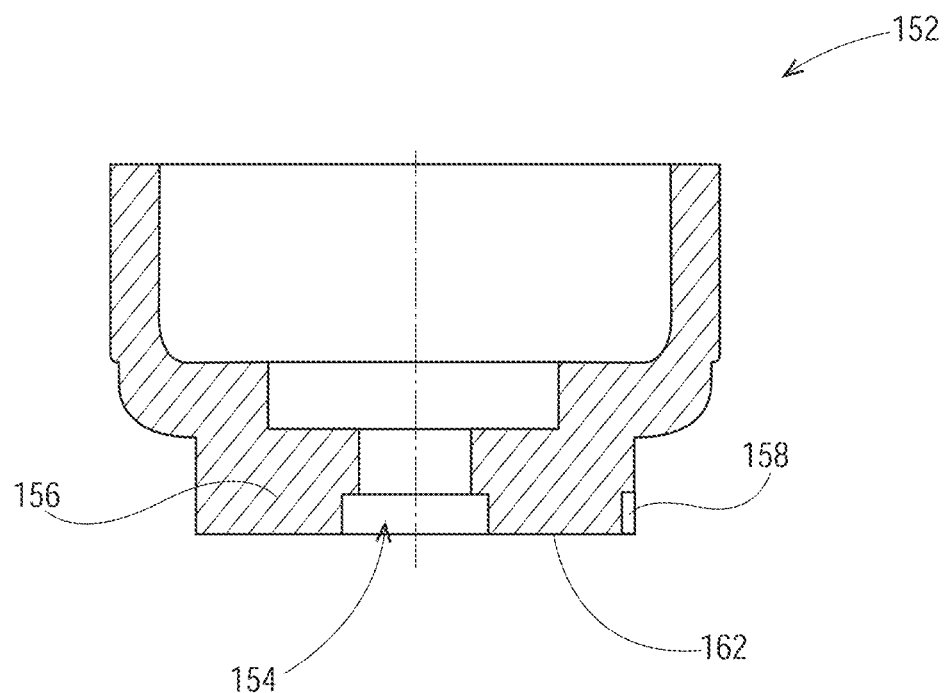
FIG. 25 is a cross-sectional side elevation view of the insert of FIG. 24, taken along line 11-11 thereof.

Referring to FIGS. 16, 19 and 21, mating sealing surfaces formed by an inner wall 146 of a substantially flat seal 148 and the wall 140 of the groove 142 form a valve that seals the valve stem orifices 138. The seal 148 may be formed from an elastomeric material, such as nitrile butadiene rubber (sometimes referred to as Buna-N). The seal 148 may be disposed about the valve stem and sandwiched between the mounting flange 128 and the housing 130, as shown by way of example in FIG. 17. The sealing surfaces are mated when the valve stem is not depressed, as shown in FIG. 17, thereby preventing flow of the antiperspirant composition/liquid propellant mixture thru the valve stem orifices 138. When the actuator 110 is depressed, the sealing surfaces separate, thereby permitting the antiperspirant composition/liquid propellant mixture to flow through the valve stem orifices 138 to the axial bore 144 and onto the actuator 110. As used herein, the term valve (as opposed to valve assembly) is intended to merely refer to the mating sealing surfaces that prevent flow of the antiperspirant composition/liquid propellant mixture from the reservoir 118 to the actuator 110. The mating sealing surfaces may be provided in configurations other than shown in the Figures and described herein. In some specific embodiments, the valve may be a continuous flow valve, meaning there is flow through the valve for as long as the actuator is depressed. In contrast, a non-continuous or metered valve allows only predetermined amount of flow thru the valve regardless how long the actuator is depressed.

Referring to FIGS. 18, 19 and 22 to 26, the housing 130 comprises a one or more holes 150 for permitting gaseous propellant to pass from the head space of the reservoir 118 into the interior of the housing 130. The housing 130 has a plurality of fingers 151 for attaching the housing to the mounting flange 128. An insert 152, which in some embodiments may be cup-shaped, may be installed within the housing 130 between the dip tube and the valve stem 124. The insert 152 may be press-fit within the housing 130 or otherwise retained within the housing by other means known in the art. The insert 152 may receive one end of the spring 132. The insert 152 has an insert bore 154 disposed in a bottom wall 156 of the insert 152. The insert bore 154 is in fluid communication with the dip tube 119 and the interior of the insert 152 so that the antiperspirant composition/liquid propellant mixture may flow from the dip tube 119 to the interior of the insert 152. The mixture then flows past the spring 132 and on to the valve.

Figure 26:
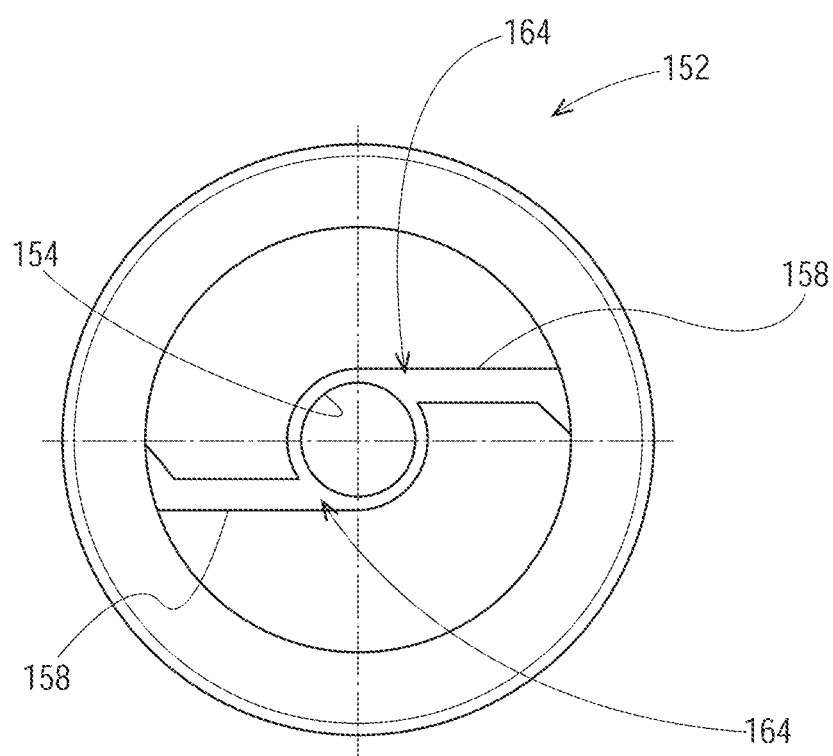
FIG. 26 is a bottom plan view of the insert of FIG. 24.

A plurality of passages 158 are disposed between the dip tube 119 and the distal end of the valve stem 124. While two passages are shown, it is contemplated that more than two passages may be provided. The passages 158 are disposed adjacent the dip tube exit and/or the tail orifice 160 (FIG. 19), the tail orifice 160 being disposed just downstream of the dip tube exit. For purposes of clarity, the passages 158 of valve assembly 114 are considered to be disposed adjacent the dip tube 119 even though there is an intervening tail orifice 160 located between the dip tube exit and the passages 158. The passages 158 are preferably located upstream of significant expansion of the antiperspirant composition/liquid propellant mixture. The passages 158 may be disposed in a bottom surface 162 of the bottom wall 156 of the cup-shaped insert 158, and passage exits 164 are disposed adjacent to the insert bore 154 and the tail orifice 160 so that gaseous propellant passing through the passages 158 impinges the antiperspirant composition/liquid propellant mixture exiting the tail orifice 160. In an embodiment, the passages 158 may be tangentially disposed the insert bore 154. The passages 158 are arranged in a manner to provide at least some, preferably significant, swirl or spin to the gaseous propellant as it exits the passages 158 and enters the insert bore 154 along with the antiperspirant composition/liquid propellant mixture. In some instances, the passages exits 164 direct the gaseous propellant in a direction substantially tangential to the flow of the antiperspirant composition/liquid propellant mixture exiting the dip tube 119 and/or tail orifice 160. The passages 158 may be arranged at an angle $\alpha$ from about 0 degrees (i.e., tangential, which is shown in FIG. 26) to about 80 degrees, or 60 degrees, or 40 degrees, or 20 degrees, the angle $\alpha$ representing the amount of angular deviation from a true tangentially arranged passage. The passages preferably have a length L sufficient to direct the gaseous propellant into swirling contact with the antiperspirant composition/liquid propellant mixture. While the passages 158 are shown disposed in the bottom surface 162 of the insert 188, it is contemplated that the passages 158 may be provided by other structures/arrangements. Without intending to be bound by any theory, it is believed that the risk of clogging may be reduced in some instances by one or more passages 158, disposed adjacent to the dip tube 119 and/or tail orifice 160, that direct at least some of the gaseous propellant from the reservoir into swirling contact (or which otherwise impart a spin to the gaseous propellant) with the antiperspirant composition/liquid propellant mixture. In some specific embodiments, the passages may have a width of 0.01 inches and a height of 0.01 inches (0.25 mm) or a width of 0.01 inches (0.25 mm) and height of 0.013 inches (0.33 mm).

While clogging may occur at various locations within a spray device flow path, the tail orifice 160, valve stem orifices 138, and actuator orifice 112 are believed to be some of the locations where clogging may occur. It is believed that balancing the flow area of the tail orifice 160 and the propellant pressure to achieve the mass flow rates described herein, rather than metering the flow rate at other locations in the flow path is, preferred as the size of the tail orifice 160 may still be large enough reduce the risk of clogging while still being small enough to effectively meter the mass flow rates to within the ranges described herein. Conversely, it is believed that attempting to meter the mass flow rates at the stem orifices 138 may lead to a higher risk of clogging than metering at the tail orifice 160. In some specific embodiments, the tail orifice 160 has a diameter (or equivalent diameter) from about 0.015 inches (0.38 mm) to 0.04 inches (1 mm) in combination with a propellant concentration from about 45% to about 65% and in further combination with a propellant pressure from about 15 psig (103 kPa) to about 46 psig (317 kPa). In some specific embodiments, the tail orifice 160 has a diameter (or equivalent diameter) from about 0.015 inches (0.38 mm) to 0.03 inches (0.76 mm), or in other embodiments from about 0.015 inches (0.38 mm) to 0.025 inches (0.64 mm), in combination with a propellant concentration from about 45% to about 55% and in further combination with a propellant pressure from about 15 psig (103 kPa) to about 32 psig (220 kPa), or in other embodiments from about 15 psig (103 kPa) to about 20 psig (138 kPa).

Turning to the valve stem orifices 138, it is believed that incorporating two opposing stem orifices having a diameter (or equivalent diameter) from about 0.012 inches (0.3 mm) to 0.016 inches (0.4 mm) in combination with the tail orifice diameters, propellant concentrations, and propellant pressure combinations previously described may, in some instances, reduce the risk for clogging at the valve stem while still achieving the desired mass flow rates.

The actuator exit orifice is another location that may be subject to clogging with the antiperspirant compositions, propellant concentrations, propellant pressures, and mass flow rates described herein. It is believed that an actuator orifice from about 0.014 inches (0.35 mm) to 0.02 inches (0.5 mm) or from about 0.014 inches (0.35 mm) to about 0.016 inches (0.4 mm) may reduce the risk for clogging at the actuator exit orifice while still achieving the desired mass flow rates.

One example of a valve assembly having the general configuration shown in FIG. 19 is available from the Precision Valve Company (USA) under the trade name Ecosol.

IV. Measurement Methods

Propellant Concentration

The overcap (if one is present) of the product container is removed, and the weight of the container and its contents (gross mass) is measured using any suitable scale, such as an analytical balance. The top of the container is punctured using any suitable tool, such as an AC-PD Aerosol Can Puncturing Device available from Aero-Tech Laboratory Equipment Company, LLC of Missouri, USA. The puncture needle is fully extended into the container, and the puncture needle is slowly retracted to permit the gaseous propellant to evacuate the container. Once the puncture needle is completely retracted from the container, the puncturing device can be removed from the container, and the propellant will continue to escape from the puncture in the container. All the propellant is allowed to evacuate from the container.

The mass of the container and the remaining contents (less the propellant) is measured using any suitable device, such as an analytical balance. The actuator is removed from the container using any suitable device, such as an Aero-Tech Can Decrimper available from Aero-Tech Laboratory Equipment Company, LLC of Missouri, USA. The inside of the container is rinsed with ethanol until visually clean and the container is allowed to dry for at least 2 hours. The mass of the empty container and actuator is measured using any suitable device, such as an analytical balance. The propellant mass and concentration may be determined using the following equations:

$$\text{Propellant Mass (g)} = \text{Gross Mass} - \text{Mass After Propellant Evacuation}$$

$$\text{Propellant Concentration \%} = \frac{\text{Propellant Mass}}{\text{Gross Mass} - \text{Mass of Empty Container}}$$

Total Mass Flow Rate

This measurement method is preferably utilized with aerosol antiperspirant products comprising a continuous actuator, meaning actuating the actuator results in a continuous rather than intermittent spray. At least four aerosol antiperspirant product samples are tested. The product samples are shaken as directed and the actuator is actuated for 2 to 3 seconds, after which each product sample is weighed to measure its mass using any suitable device, such as an analytical balance. The product samples are then immersed in a constant-temperature (25° C.) bath until the internal pressure stabilizes at a temperature of 25° C. The product samples are then removed from the bath and excess moisture is removed by blotting with a paper towel. The products samples are shaken if directed and the actuator is actuated for 5 seconds, which may be accurately timed by use of a stopwatch. Each product sample is again weighed, after which the product samples are returned to the constant-temperature bath. The process of bathing, actuating, and weighing is repeated three times for each product sample. The average total mass flow rate may be calculated from the spray time period (5.0 seconds) and the difference in mass before and after each five second spray, averaged across the four product samples and three repetitions per product sample.

Antiperspirant Composition Mass Flow Rate

This measurement method is preferably utilized with aerosol antiperspirant products comprising a continuous actuator, meaning actuating the actuator results in a continuous rather than intermittent spray. At least four aerosol antiperspirant product samples are tested. The product samples are shaken if directed and then immersed in a constant-temperature (25 C) bath until the internal pressure stabilizes at a temperature of 25° C. The product samples are then removed from the bath and excess moisture is removed by blotting with a paper towel. Each product sample is weighed to measure its mass using any suitable device, such as an analytical balance. Twelve large plastic bags (one for each product sample times three repetitions) having a suitable volume, such as a 1 L Ziploc brand bag (or a Whirl-Pak Write-on 55 ounce bag, Part # B01195WA available from Nasco, Inc), are weighed to measure their mass using any suitable device, such as an analytical balance. Each product sample is shaken if directed and sprayed into one of the bags for a period of 5 seconds in a manner that minimizes antiperspirant composition from exiting the bag. For example, the opening thru which the spray enters the bag may be limited to about 5 cm. The 5 second spray time period may be accurately measured using a stopwatch. Following the 5 second spray period, the antiperspirant composition is allowed to settle within the bag and the bag remains open for at least 1 minute but not longer than 2 minutes in order to allow the liquid propellant to evaporate. The weight of the bags and their contents are weighed to measure their mass, and the product samples are also weighed. The average mass flow rate of the antiperspirant composition may be determined using the following equation which is averaged across the four product samples and the three repetitions per product sample:

Mass Flow Rate of Antiperspirant Composition (g/sec)=Weight of Bag and Antiperspirant Composition−Weight of Bag/5 seconds Antiperspirant Composition Deposition Efficiency, Amount Dispensed, and Amount Deposited At least four aerosol antiperspirant product samples are tested. The product samples are shaken if directed and the actuator is actuated for 2 to 3 seconds, after which each product sample is weighed to measure its mass using any suitable device, such as an analytical balance. The product samples are then immersed in a constant-temperature (25° C.) bath until the internal pressure stabilizes at a temperature of 25° C. as determined by constancy of internal pressure. At least twelve filter papers, such as Whatman 150 mm (diameter) Filter Paper available under the catalog number 1003-150 from the Whatman Company of the UK, are weighed to measure the mass of the filter using any suitable device, such as an analytical balance. The product samples are removed from the bath, and any excess moisture is removed by blotting with a paper towel. The product samples are shaken if directed, and the product sample is positioned approximately 15 cm away from one of the filter papers, which is preferably weighted and/or fixtured to assure the filter paper does not move during spraying. The actuator of the product sample is actuated for 5 seconds which may be accurately timed using a stopwatch. It will be appreciated, however, that other spray times may be substituted. For example, a two second spray time period might be used to better approximate the amount dispensed/deposited during a typical use cycle by a consumer. The spray from the product sample should be centered on the center of the filter paper. After spraying, the filter paper and product sample are weighed to measure the mass using any suitable device, such as an analytical balance. The steps of bathing, weighing, and actuating are repeated three times for each of the product samples. The average antiperspirant composition efficiency may be calculated using the following equations, averaged across the four product samples and the three repetitions per product sample:

$$\text{Amount Dispensed (g)} = \text{Product Sample Weight Before Spraying} - \text{Product Sample Weight After Spraying}$$

$$\text{Amount Deposited (g)} = \text{Filter Paper Weight After Spraying} - \text{Filter Paper Weight Before Spraying}$$

$$\text{Antiperspirant Composition Deposition Efficiency (\%)} = 100 \times \frac{\text{Amount Deposited}}{\text{Amount Dispensed} * \text{Antiperspirant Composition Weight \%}}$$

Antiperspirant Active Deposition Efficiency, Amount Dispensed, and Amount Deposited At least four aerosol antiperspirant product samples are tested. The product samples are shaken if directed and the actuator is actuated for 2 to 3 seconds, after which each product sample is weighed to measure its mass using any suitable device, such as an analytical balance. The product samples are then immersed in a constant-temperature (25° C.) bath until the internal pressure stabilizes at a temperature of 25° C. The product samples are then removed from the bath and excess moisture is removed by blotting with a paper towel. At least twelve filter papers, such as Whatman 150 mm Filter Paper available under the catalog number 1003-150 from the Whatman Company of the UK, are weighed to measure the mass of the filter using any suitable devices, such as an analytical balance. The product samples are removed from the bath, and any excess moisture is removed by blotting with a paper towel. The product samples are shaken if directed, and the product sample is positioned approximately 15 cm away from one of the filter papers, which is preferably weighted and/or fixtured to assure the filter paper does not move during spraying. The actuator of the product sample is actuated for 5 seconds which may be accurately timed using a stopwatch. It will be appreciated that other spray times may be substituted. For example, a two second spray time period might be used to better approximate the amount dispensed/deposited during a typical use cycle by a consumer. The spray from the product sample should be centered on the center of the filter paper. After spraying, the filter paper and product sample are weighed to measure the mass using any suitable device, such as an analytical balance. The steps of bathing, weighing, and actuating are repeated three times for each of the product samples. The amount of antiperspirant active deposited on a filter paper may be determined using an automated titrator, such as MettlerDL-70 equipped with Mettler DM141C combination silver-silver chloride electrode available from Mettler, Inc. Alternatively, the amount of antiperspirant active deposited on a filter paper may be determined using the Content of Chloride Method set forth in the USP monograph for aluminum chlorohydrate (USP 35) or an equivalent method. The average antiperspirant active deposition efficiency may be calculated using the following equations, averaged across the four product samples and the three repetitions per product sample:

$$\text{Amount Dispensed (g)} = \text{Product Sample Weight Before Spraying} - \text{Product Sample Weight After Spraying}$$

$$\text{Amount Deposited (gm)} = \text{Filter Paper Weight Before Spraying} - \text{Filter Paper Weight After Spraying}$$

$$\text{Antiperspirant Composition Efficiency (\%)} = 100 \times \frac{\text{Amount Deposited}}{\text{Amount Dispensed} * \text{Antiperspirant Composition Weight \%}}$$

Long Term Settling Height and Short Term Settling Height

Long term settling height and short term settling height are directionally quantitative measures of the amount of bulking/suspending provided by a clay materials in an antiperspirant composition. Long term settling height is the height of the antiperspirant composition after settling for 24 hours after shaking while short term settling height is the height of the antiperspirant composition 2 minutes after shaking. 20 grams of the antiperspirant composition into a clear glass aerosol container (part number—ATL-SC4-48 from Aero-Tech Laboratory Equipment Company, LLC). The glass container had a diameter of 55 mm and a height of 107 mm. The glass container is sealed with an appropriate valve. 40 gms of isobutane propellant is added to the glass container through the valve. The glass containers are shaken to completely disperse the antiperspirant composition and the glass containers are then hot tanked for 4 minutes (130 F) to confirm the unit is completely sealed. After cooling, the glass containers are shaken again and allowed to stand for 24 hrs.

To evaluate antiperspirant compositions that have been previously packed in other aerosol containers, the antiperspirant composition may be acquired by the following process. The overcap of the container is removed. The top of the container is punctured using any suitable tool, such as an AC-PD Aerosol Can Puncturing Device available from Aero-Tech Laboratory Equipment Company, LLC of Missouri, USA. The puncture needle is fully extended into the container, and the puncture needle is slowly retracted to permit the gaseous propellant to evacuate the container. Once the puncture needle is completely retracted from the container, the puncturing device can be removed from the container, and the propellant will continue to escape from the puncture in the container. All the propellant is allowed to evacuate from the container before removing 20 grams of the remaining antiperspirant composition for addition to the glass container. It may be necessary to combine antiperspirant composition from multiple containers should there not be 20 grams of material in a single package.

The long term settling height is then easily measured using a clear ruler (although any appropriated measuring device is possible) and is defined as the distance from the top of the antiperspirant composition powder pack to its bottom. Care should be taken during this process to prevent significant agitation that would redisperse the powder pack. The short term settling height is measured by first shaking the glass container vigorously for 30 seconds to achieve complete dispersion of the antiperspirant composition. The glass container is then placed on a flat surface without further agitation for 2 minutes (±5 seconds). The short term settling height is then easily measured at that time using a clear ruler (although any appropriated measuring device is possible) and is defined as the distance from the top of the antiperspirant composition powder pack to its bottom.

Redispersion

The redispersion characteristics of a composition may be measured by the number of turns of a transparent container that are need to redisperse a composition that has undergone long term settling (24 hours per above). First, a composition is prepared and allowed to settle long term as provided above. The number of turns is determined by slowly rotating the container about its mid-point at a rate of approximately one full rotation in two seconds. The number of full rotations or turns required to fully disperse the composition is recorded. Preferably, at least three sets of rotational tests are conducted to obtain an average value for the number of turns needed to fully redisperse the composition given there is some subjectivity as to when full redispersion occurs. Compositions having a well activated clay material should result in powdery redispersion, meaning the particulates easily flowed away from the powder pack in a widely dispersed pattern during the first turn. In contrast, compositions that are highly caked following long term settling are more challenging to determine number of turns as clumps of the antiperspirant composition may fall off of the bottom and in the process aid break-up and redispersion. However, this phenomenon indicates a poorly activated clay material. For these reasons, the number of turns of a composition is one method for directionally assessing the activation of a clay material.

Light Transmittance Value

Solubility of a liquid activation enhancer in a non-volatile silicone may be determined by measuring the amount of light transmittance (light transmittance value) through a simple mixture of the non-volatile silicone fluid and liquid activation enhancer at the same weight/weight concentrations as in a final antiperspirant composition. For example, the solubility of a liquid activation enhancer at a concentration of 9% w/w in a final antiperspirant composition comprising a non-volatile silicone fluid having a concentration of 38% w/w can be determined by measuring the light transmittance of a simple mixture of the liquid activation enhancer at 19% w/w concentration in just the non-volatile silicone fluid.

The light transmittance value using a spectrophotometer, such as, for example, a Spectronic Genesys 10 Vis Spectrophotometer available from Thermo Electron Corp (USA) or other similar spectrophotometer. The Spectronic Genesys 10 Vis utilizes a tungsten-halogen light source and has a spectral bandwidth of 5 nm, a wavelength range of 325 to 1100 nm, accuracy of ±1 nm and a repeatability of ±0.5 nm. Readouts include absorbance, transmittance and concentration. The spectrophotometer is set to 640 nm wavelength and the percent transmittance mode/readout. Polystyrene spectrometer cuvettes having a 1 cm optical light path and transmittance between ~340 nm and ~900 nm are used. One suitable example of a spectrometer cuvette is available from VWR International LLC under Catalog #97000-584 having a 2.5 to 4.5 ml capacity. The spectrophotometer is calibrated according to the manufacturer's instructions using a reference cuvette and composition comprised of just the non-volatile silicone fluid of interest. For example, if the test composition comprises 50 centistoke dimethicone and 15% w/w of isopropyl myristate, then the spectrometer is calibrated using a cuvette containing just 50 centistoke dimethicone. Sample cuvettes are filled sufficiently with a test composition of a non-volatile silicone fluid and liquid activation enhancer so that the light path of the spectrophotometer passes through the test composition in the cuvette. The sample cuvettes are shaken well just prior to taking a light transmittance reading. Light transmittance values greater than 80%, 85%, 90% or 95% at 25° C. indicates solubility of the liquid activation enhancer in the non-volatile silicone fluid of the final antiperspirant composition.

V. EXAMPLES

The following examples are given solely for the purpose of illustration and are not to be construed as limitations of the invention as many variations thereof are possible without departing from the spirit and the scope of the invention.

Examples 1 to 9

Examples 1 to 6 describe some non-limiting comparative examples of antiperspirant compositions, while Examples 7 to 9 describe some non-limiting examples of antiperspirant compositions comprising a liquid activation enhancer.

| Ingredient | EX 1 | EX 2 | EX 3 | EX 4 | EX 5 | EX 6 | EX 7 | EX 8 | EX 9 |
|---|---|---|---|---|---|---|---|---|---|
| Aluminum Chlorohydrate[1] | 26.37% | 26.37% | 26.37% | 26.37% | 26.37% | 26.37% | 26.37% | 26.37% | 26.37% |
| Cyclopentasiloxane | 52.5% | 47% | 47% | 0% | 0% | 0% | 0% | 0% | 0% |
| Dimethicone[2] | 0% | 0% | 0% | 52.5% | 47% | 47% | 43.5% | 38% | 38% |
| Isopropyl Myristate | 0% | 0% | 0% | 0% | 0% | 0% | 9% | 9% | 9% |
| Hydrophilic tapioca material[3] | 12% | 12% | 12% | 12% | 12% | 12% | 12% | 12% | 12% |
| Stearalkonium Hectorite[4] | 4.25% | 4.25% | 4.25% | 4.25% | 4.25% | 4.25% | 4.25% | 4.25% | 4.25% |
| Triethyl Citrate | 1.38% | 1.38% | 1.38% | 1.38% | 1.38% | 1.38% | 1.38% | 1.38% | 1.38% |
| Silicone Gum[5] | 0.5% | 0.5% | 0.5% | 0.5% | 0.5% | 0.5% | 0.5% | 0.5% | 0.5% |
| Liquid Fragrance Material[6] | 0% | 5.5% | 5.5% | 0% | 5.5% | 5.5% | 0% | 5.5% | 5.5% |
| Complexed Beta Cyclodextrin | 3% | 3% | 3% | 3% | 3% | 3% | 3% | 3% | 3% |
| Total | 100 | 100 | 100 | 100 | 100 | 100 | 100 | 100 | 100 |

[1]86% assay of anhydrous active, average particle size approximately 15 microns.
[2]DC 200 Fluid (50 centistoke) available from Dow Corning
[3]Tapioca Pure from Akzo Nobel
[4]Bentone 38 available from Elementis
[5]DC1503 (a mixture of dimethicone and dimethiconol) available from Dow Corning
[6]Is believed to have contained isopropyl myristate at less than 10% w/w of the liquid fragrance material Examples 1, 2, 4, 5, 7 and 8 were prepared by mixing a first portion of the cyclopentasiloxane or dimethicone, isopropyl myristate (if present) and disteardimonium hectorite by lightly stirring followed by milling for at least 1 minute using a single head Silverson mill. The triethyl citrate was added next followed by at least five minutes of milling, followed by addition of the aluminum chlorohydrate, a second portion of the dimethicone, the complexed BCDs, tapioca material, dimethicone/dimethiconol and liquid fragrance material. After making the composition, approximately 20 gms thereof was added to a clear glass aerosol bottle (Part # ATL-SC4-48 available from Aero-Tech Laboratory Equipment Co of USA). The glass bottle was sealed with a valve assembly and then approximately 40 gms of isobutane propellant was added to the bottle thru the valve assembly. Each sample was shaken to disperse the composition and hot tanked for four minutes at 130° F. After cooling, the samples were shaken again and allowed to stand for 24 hrs (long term settling) prior to rotational and short term settling testing. Examples 3, 6 and 9 were prepared by mixing a first portion of the cyclopentasiloxane or dimethicone, isopropyl myristate (if present) and disteardimonium hectorite by lightly stirring followed by milling for at least 1 minute using a single head Silverson Mill. The triethyl citrate was added next followed by at least five minutes of milling, followed by addition of the aluminum chlorohydrate, a second portion of the dimethicone, the complexed BCDs, tapioca material and dimethicone/dimethiconol. Approximately 18.9 gms of this mixture was then added to a clear glass aerosol bottle (Part # ATL-SC4-48 available from Aero-Tech Laboratory Equipment Co of USA) followed by approximately 1.1 gms of the liquid fragrance material. The glass bottle was sealed with a valve assembly and then approximately 40 gms of isobutane propellant was added to the bottle thru the valve assembly. Each sample was shaken to disperse the composition and hot tanked for four minutes at 130 F. After cooling, the samples were shaken again and allowed to stand for 24 hrs (long term settling) prior to rotational and short term settling testing. Table 3 below sets forth the long term settling height, short term settling height, average turns and observations related thereto for Examples 1 to 9.

TABLE 3

| | Long Term Settling Height (mm) | Short Term Settling Height (mm) | Average Turns (N = 3) | Observations |
|---|---|---|---|---|
| EX 1 | 17 | 32 | 6.3 | Powdery redispersion |
| EX 2 | 15 | 40 | 10 | Powdery redispersion |
| EX 3 | 14 | 39 | 7.3 | Powdery redispersion |
| EX 4 | 12 | 14 | 8 | Composition falls off of the bottom in clumps and then redisperses |
| EX 5 | 10 | 19 | 26 | Majority of composition still packed on bottom after 5 turns |
| EX 6 | 10 | 21 | 22 | Majority of composition still packed on bottom after 5 turns |
| EX 7 | 17 | 33 | 6.3 | Powdery redispersion |
| EX 8 | 13 | 40 | 12 | Powdery redispersion |
| EX 9 | 15 | 40 | 8 | Powdery redispersion |

Examples 10 to 17

Examples 10 to 13 describe some non-limiting examples of antiperspirant compositions comprising a liquid activation enhancer, while Examples 14 to 17 describe some non-limiting comparative examples of antiperspirant compositions.

| Ingredient | EX 10 | EX 11 | EX 12 | EX 13 | EX 14 | EX 15 | EX 16 | EX 17 |
|---|---|---|---|---|---|---|---|---|
| Aluminum Chlorohydrate[1] | 26.5% | 26.5% | 16.32% | 26.37% | 26.5% | 26.5% | 26.5% | 26.5% |
| Dimethicone[2] | 38.18% | 38.18% | 32.14% | 43% | 38.18% | 38.18% | 38.18% | 38.18% |
| Isopropyl Palmitate | 9.05% | 0% | 0% | 0% | 0% | 0% | 0% | 0% |
| Butyl Stearate | 0% | 9.05% | 0% | 0% | 0% | 0% | 0% | 0% |

-continued

| Ingredient | EX 10 | EX 11 | EX 12 | EX 13 | EX 14 | EX 15 | EX 16 | EX 17 |
|---|---|---|---|---|---|---|---|---|
| Isopropyl Myristate | 0% | 0% | 29.98% | 4% | 0% | 0% | 0% | 0% |
| Mineral Oil | 0% | 0% | 0% | 0% | 9.05% | 0% | 0% | 0% |
| Isohexadecane | 0% | 0% | 0% | 0% | 0% | 9.05% | 0% | 0% |
| Octyldodecanol | 0% | 0% | 0% | 0% | 0% | 0% | 9.05% | 0% |
| PPG-14-Butyl Ether | 0% | 0% | 0% | 0% | 0% | 0% | 0% | 9.05% |
| Hydrophilic tapioca material[3] | 12.06% | 12.06% | 7.43% | 12% | 12.06% | 12.06% | 12.06% | 12.06% |
| Stearalkonium Hectorite[4] | 4.27% | 4.27% | 4.25% | 4.25% | 4.27% | 4.27% | 4.27% | 4.27% |
| Triethyl Citrate | 1.39% | 1.39% | 1.38% | 1.38% | 1.39% | 1.39% | 1.39% | 1.39% |
| Silicone Gum[5] | 0% | 0% | 0% | 0.5% | 0% | 0% | 0% | 0% |
| Liquid Fragrance Material[6] | 5.53% | 5.53% | 5.5% | 5.5% | 5.53% | 5.53% | 5.53% | 5.53% |
| Complexed Beta Cyclodextrin | 3.02% | 3.02% | 3% | 3% | 3.02% | 3.02% | 3.02% | 3.02% |
| Total | 100 | 100 | 100 | 100 | 100 | 100 | 100 | 100 |

[1] 86% assay of anhydrous active, average particle size approximately 15 microns.
[2] DC 200 Fluid (50 centistoke) available from Dow Corning
[3] Tapioca Pure from Akzo Nobel
[4] Bentone 38 available from Elementis
[5] DC1503 (a mixture of dimethicone and dimethiconol) available from Dow Corning
[6] Is believed to have contained isopropyl myristate at less than 10% w/w of the liquid fragrance material Examples 10 to 17 were prepared by mixing a first portion of the dimethicone; one of isopropyl myristate, isopropyl palmitate, butyl stearate, mineral oil, isohexadecane, octyldodecanol and PPG-14-butyl ether; and disteardimonium hectorite by lightly stirring followed by milling for at least 1 minute using a single head Silverson mill. The triethyl citrate was added next followed by at least five minutes of milling, followed by addition of the aluminum chlorohydrate, a second portion of the dimethicone, the complexed BCDs, tapioca material, dimethicone/dimethiconol and liquid fragrance material. After making the composition, approximately 20 gms thereof was added to a clear glass aerosol bottle (Part # ATL-SC4-48 available from Aero-Tech Laboratory Equipment Co of USA). The glass bottle was sealed with a valve assembly and then approximately 40 gms of isobutane propellant was added to the bottle thru the valve assembly. Each sample was shaken to disperse the composition and hot tanked for four minutes at 130° F. After cooling, the samples were shaken again and allowed to stand for 24 hrs (long term settling) prior to rotational and short term settling testing. Table 4 below sets forth the long term settling height, short term settling height, average turns and observations related thereto for Examples 10 to 17.

TABLE 4

| | Long Term Settling Height (mm) | Short Term Settling Height (mm) | Average Turns (N = 3) | Observations |
|---|---|---|---|---|
| EX 10 | 14 | 38 | 8 | Powdery redispersion |
| EX 11 | 13 | 35 | 9 | Powdery redispersion |
| EX 12 | 10 | 25 | 7 | Powdery redispersion |
| EX 13 | 15 | 38 | 6 | Powdery redispersion |
| EX 14 | 12 | 22 | 6 | Composition falls off of the bottom in clumps and then redisperses |
| EX 15 | 12 | 35 | 15 | Composition falls off of the bottom in clumps and then redisperses. |
| EX 16 | 11 | 24 | 9 | Composition falls off of the bottom in clumps and then redisperses. Composition was grainy - not homogenous |
| EX 17 | 11 | 34 | 15 | Composition falls off of the bottom in clumps and then redisperses. Composition was grainy - not homogenous |

Examples 18 to 23

Examples 18 and 23 describe some non-limiting examples of antiperspirant compositions comprising C12-15 alkyl benzoate and isopropyl myristate.

| Ingredient | EX 18 | EX 19 | EX 20 | EX 21 | EX 22 | EX 23 | EX 24 |
|---|---|---|---|---|---|---|---|
| Aluminum Chlorohydrate[1] | 26.5% | 26.5% | 26.5% | 26.5% | 26.5% | 26.5% | 26.37% |
| 5 Centistoke Dimethicone[2] | 45.22% | 38.18% | 0% | 0% | 0% | 0% | 0% |
| 10 Centistoke Dimethicone[2] | 0% | 0% | 38.18% | 0% | 0% | 0% | 0% |
| 20 Centistoke Dimethicone[2] | 0% | 0% | 0% | 38.18% | 39.57% | 0% | 0% |

-continued

| Ingredient | EX 18 | EX 19 | EX 20 | EX 21 | EX 22 | EX 23 | EX 24 |
|---|---|---|---|---|---|---|---|
| 50 Centistoke Dimethicone[2] | 0% | 0% | 0% | 0% | 0% | 38.18% | 38% |
| C12-15 Alkyl Benzoate | 2.01% | 9.05% | 9.05% | 9.05% | 9.05% | 9.05% | 0% |
| Isopropyl Myristate | 0% | 0% | 0% | 0% | 0% | 0% | 9% |
| Hydrophilic tapioca material[3] | 12.06% | 12.06% | 12.06% | 12.06% | 12.06% | 12.06% | 12% |
| Stearalkonium Hectorite[4] | 4.27% | 4.27% | 4.27% | 4.27% | 4.27% | 4.27% | 4.25% |
| Triethyl Citrate | 1.39% | 1.39% | 11.39% | 1.39% | 0% | 1.39% | 1.38% |
| Silicone Gum[5] | -none | none | none | none | none | none | 0.5% |
| Liquid Fragrance Material[6] | 5.53% | 5.53% | 5.53% | 5.53% | 5.53% | 5.53% | 5.5% |
| Complexed Beta Cyclodextrin | 3.02% | 3.02% | 3.02% | 3.02% | 3.02% | 3.02% | 3% |
| Total | 100 | 100 | 100 | 100 | 100 | 100 | 100 |

[1]86% assay of anhydrous active, average particle size approximately 15 microns.
[2]DC 200 Fluid (5, 10, 20 or 50 centistoke) available from Dow Corning
[3]Tapioca Pure from Akzo Nobel
[4]Bentone 38 available from Elementis
[5]DC1503 (a mixture of dimethicone and dimethiconol) available from Dow Corning
[6]Is believed to have contained isopropyl myristate at less than 10% w/w of the liquid fragrance material Examples 18 to 23 were prepared by mixing a first portion of the dimethicone, C12-15 alkyl benzoate, and disteardimonium hectorite by lightly stirring followed by milling for at least 1 minute using a single head Silverson mill. The triethyl citrate was added next followed by at least five minutes of milling, followed by addition of the aluminum chlorohydrate, a second portion of the dimethicone, the complexed BCDs, tapioca material, dimethicone/dimethiconol and liquid fragrance material. After making the composition, approximately 20 gms thereof was added to a clear glass aerosol bottle (Part # ATL-SC4-48 available from Aero-Tech Laboratory Equipment Co of USA). The glass bottle was sealed with a valve assembly and then approximately 40 gms of isobutane propellant was added to the bottle thru the valve assembly. Each sample was shaken to disperse the composition and hot tanked for four minutes at 130° F. After cooling, the samples were shaken again and allowed to stand for 24 hrs (long term settling) prior to rotational and short term settling testing. Table 5 below sets forth the long term settling height, short term settling height, average turns and observations related thereto for Examples 18 to 23. Example 24 was prepared according to the process shown in FIG. 14.

TABLE 5

| | Long Term Settling Height (mm) | Short Term Settling Height (mm) | Average Turns (N = 3) | Observations |
|---|---|---|---|---|
| EX 18 | 12 | 25 | 15 | Some clumping during redispersion |
| EX 19 | 15 | 40 | 7 | Powdery redispersion |
| EX 20 | 14 | 39 | 5 | Powdery redispersion |
| EX 21 | 13 | 35 | 9 | Powdery redispersion |
| EX 22 | 15 | 33 | 10 | Powdery redispersion |
| EX 23 | 9 | 10 | 15 | Product falls off bottom in clumps and then redisperses |
| EX 24 | 12 | 31 | 6 | Powdery redispersion |

Examples 25 to 35 describe some non-limiting examples of combinations of antiperspirant compositions and propellants. The concentration of particulates by weight of the total fill of materials (e.g., antiperspirant composition plus propellant) is also set forth in Examples 25 to 35.

| Ingredient | EX 25 | EX 26 | EX 27 | EX 28 | EX 29 | EX 30 | EX 31 | EX 32 | EX 33 | EX 34 | EX 35 |
|---|---|---|---|---|---|---|---|---|---|---|---|
| Propellant (A-46) | 50 | 50 | 50 | 0 | 0 | 0 | 0 | 0 | 0 | 0 | 0 |
| Propellant (A-31) | 0 | 0 | 0 | 50 | 0 | 50 | 50 | 65 | 65 | 65 | 65 |
| Propellant (A-17) | 0 | 0 | 0 | 0 | 50 | 0 | 0 | 0 | 0 | 0 | 0 |
| Aluminum Chlorohydrate[1] | 14 | 14 | 9.5 | 14 | 13.19 | 9.5 | 9.5 | 6.65 | 9.8 | 6.65 | 6.65 |
| Dimethicone[2] | 24.19 | 26.15 | 30.62 | 23.5 | 24.72 | 28 | 28 | 19.6 | 16.45 | 19.6 | 19.6 |
| Empty Beta Cylcodextrin | 0 | 0 | 0 | 6 | 0 | 6 | 3 | 0 | 4.2 | 4.2 | 2.1 |
| Hydrophilic tapioca material[3] | 0 | 6 | 6 | 0 | 6 | 0 | 3 | 4.2 | 0 | 0 | 2.1 |
| Hydrophobic tapioca material[4] | 6 | 0 | 0 | 0 | 0 | 0 | 0 | 0 | 0 | 0 | 0 |
| Stearalkonium Hectorite[5] | 1 | 0 | 0 | 1.5 | 2.13 | 1.5 | 1.5 | 1.05 | 1.05 | 1.05 | 1.05 |
| Triethyl Citrate | 0.335 | 0 | 0 | 0.5 | 0.69 | 0.5 | 0.5 | 0.35 | 0.35 | 0.35 | 0.35 |
| Hydrophilic Silica | 0 | 0.5 | 0.5 | 0 | 0 | 0 | 0 | 0 | 0 | 0 | 0 |
| Hydrophobic Silica | 0 | 0.125 | 0.125 | 0 | 0 | 0 | 0 | 0 | 0 | 0 | 0 |
| Silicone Gum[6] | 0.5 | 0 | 0 | 0.25 | 0.03 | 0.25 | 0.25 | 0.18 | 0.18 | 0.18 | 0.18 |
| Lauryl Alcohol | 0 | 0 | 0 | 1 | 0 | 1 | 1 | 0.7 | 0.7 | 0.7 | 0.7 |

-continued

| Ingredient | EX 25 | EX 26 | EX 27 | EX 28 | EX 29 | EX 30 | EX 31 | EX 32 | EX 33 | EX 34 | EX 35 |
|---|---|---|---|---|---|---|---|---|---|---|---|
| Fragrance | 1.75 | 1.75 | 1.75 | 1.75 | 1.75 | 1.75 | 1.75 | 1.22 | 1.22 | 1.22 | 1.22 |
| Complexed Beta Cyclodextrin | 1.5 | 1.5 | 1.5 | 1.5 | 1.5 | 1.5 | 1.5 | 1.05 | 1.05 | 1.05 | 1.05 |
| Total | 100 | 100 | 100 | 100 | 100 | 100 | 100 | 100 | 100 | 100 | 100 |
| % Total Particulates | 22.5 | 22.125 | 18 | 23 | 22.5 | 19 | 19 | 13 | 16 | 13 | 13 |

[1] 86% assay of anhydrous active, average particle size approximately 15 microns.
[2] DC 200 Fluid (50 centistoke) available from Dow Corning
[3] Tapioca Pure from Akzo Nobel
[4] Dry Flo TS from Akzo Nobel
[5] Bentone 38 available from Elementis
[6] DC1503 (a mixture of dimethicone and dimethiconol) available from Dow Corning
7 Aerosil A300 silica from Evonik
8 Aerosil A300 silica from Evonik The antiperspirant compositions of Examples 25 to 35 were made using the following general batch method: the non-volatile silicone fluid was added to an appropriately sized container followed by the silica or clay and the mixture was milled for at least 1 minute at a speed of 10,000 to 12,000 rpm using a hand held miller. If clay was added, triethyl citrate was also added to the mixture and milled for at least 5 minutes. The antiperspirant active particles were added to the mixture and milled for at least 1 minute. The tapioca material, empty beta cyclodextrin material and beta cyclodextrin fragrance materials as appropriate were added to the mixture and milled for at least one minute. The liquid fragrance material was then added along with a silicone gum, if desired, and milled for at least one minute.

The antiperspirant composition of Example 25 had an average viscosity of approximately 4,200 centipoise. The antiperspirant composition of Example 26 had an average viscosity of approximately 3,000 centipoise, and the antiperspirant composition of Example 27 had an average viscosity of approximately 1,500 centipoise. The viscosity measurements were made using a Brookfield RVT Viscometer Model using an RV-4 spindle and techniques well known in the art.

Spray devices may be filled by transferring the desired weight (approximately 15 g) of the antiperspirant composition to a 55 ml container and affixing a valve assembly. An appropriate amount of (A-46, A-31 or A-17) was propellant is added to the containers to achieve a 50% or 65% propellant concentration by weight of the total fill of materials.

In Vivo Testing of Examples 25, 26, 27, Comparative Example 36 and a Commercial Product Spray devices comprising the propellants and antiperspirant compositions of Examples 25, 26, 27 and comparative Example 36 were prepared. The antiperspirant composition of comparative Example 36 was made in a manner generally similar to that previously described for Examples 25 to 27.

| Ingredient | EX 36 |
|---|---|
| Propellant (A-46) | 50 |
| Aluminum Chlorohydrate | 14 |
| Dimethicone | 2.5 |
| Cyclopentasiloxane | 23.75 |
| Hydrophilic Tapioca Material | 6 |
| Hydrophilic Silica | 0.5 |
| Hydrophobic Silica | 0.125 |
| Fragrance | 1.75 |
| Complexed Beta Cyclodextrin | 1.5 |
| Total | 100 |
| % Total Particulates | 22.125 |

An in vivo study was conducted with spray devices comprising the antiperspirant compositions and propellant combinations of Examples 25, 26, 27, comparative example 36 and a commercially available aerosol antiperspirant product. The packaging for the commercially available aerosol antiperspirant product listed the following ingredients: butane, isobutene, propane, cyclomethicone, aluminum chlorohydrate, parfum, disteardimonium hectorite, dimethiconol, PVM/MA copolymer, sodium starch octenylsuccinate, mannitol, alpha-isomethyl ionone, butylphenyl methylpropional, citronellol, eugenol, geraniol, hexyl cinnamal, 1-limonene and linalool. The commercially available aerosol antiperspirant product had an average propellant concentration of approximately 85% (believed to be A-46 propellant) and an average reservoir pressure of approximately 410 kPa. The commercially available antiperspirant product also had an average total mass flow rate of approximately 1.02 g/sec, and an average antiperspirant composition mass flow rate of approximately 0.20 g/sec.

Spray devices comprising the antiperspirant composition of Example 25 had an average total mass flow rate of approximately 0.37 g/sec and an average antiperspirant composition flow rate of approximately 0.17 g/sec. The spray devices comprising the antiperspirant composition of Example 26 had an average total mass flow rate of approximately 0.38 g/sec and an average antiperspirant composition flow rate of approximately 0.18 g/sec. The spray devices comprising the antiperspirant composition of Example 27 had an average total mass flow rate of approximately 0.36 g/sec and an average antiperspirant composition flow rate of approximately 0.17 g/sec. The spray devices comprising the antiperspirant composition of comparative Example 36 had an average total mass flow rate of approximately 0.39 g/sec and an average antiperspirant composition flow rate of approximately 0.18 g/sec.

Forty-eight subjects were enrolled in the study, of which 45 completed the study. The study lasted 26 days, comprising a 21 day washout period in which the subjects used no antiperspirant products (deodorant products only were applied) followed by a 5 day treatment period with the aerosol antiperspirant products. The antiperspirant products were applied once each morning during the 5 day treatment period. Hot room evaluations for sweat production were conducted prior to start of the 5 day treatment period (baseline) and 12 hours post the $5^{th}$ day of the treatment period. The adjusted mean sweat values (mg sweat) at the start of the study (baseline) and twelve hours post treatment day 5 are shown below.

|  | Mean Sweat at Baseline (mg of sweat collected) | Baseline Adjusted Mean Sweat Value 12 hrs Post Treatment Day #5 (mg of sweat collected) |
|---|---|---|
| Spray Devices with Antiperspirant Composition of Example 25 | 595 | 382 |
| Spray Devices with Antiperspirant Composition of Example 26 | 591 | 362 |
| Spray Devices with Antiperspirant Composition of Example 27 | 665 | 343 |
| Spray Devices with Antiperspirant Composition of Comparative Example 36 | 676 | 405 |
| Commercially Available Aerosol Antiperspirant Product | 591 | 439 |

After five days of treatment, the spray devices comprising the antiperspirant compositions/propellants of Examples 25, 26 and 27 resulted in lower mean sweat values (mg of sweat) twelve hours post treatment day #5 than both the commercially available antiperspirant product and comparative Example 36. A lower mean sweat value means less perspiration was released from the eccrine glands in the underarm area, resulting in a higher antiperspirant efficacy. The results for the spray devices comprising the antiperspirant compositions of Examples 26 and 27 were statistically significant (with at least a 90% confidence level). The results for the composition of Example 27 are particularly notable, as this composition had the lowest concentration of antiperspirant active among Examples 25, 26 and 27 and yet had the lowest mean sweat value post treatment among the tested antiperspirant compositions. This may be due to the higher dimethicone concentration, which may have increased substantivity of the antiperspirant active on skin compared to the antiperspirant compositions of Examples 25 and 26. The commercially available product, which had the highest propellant concentration, had the highest mean sweat value post treatment despite having the highest antiperspirant mass flow rate among the products. This may be due, at least in part, to the low deposition efficiency of the commercially available product in combination with a lack of antiperspirant active substantivity resulting from the use of a volatile silicone fluid as the liquid carrier. The mean sweat value post treatment for the antiperspirant compositions of Example 26 were directionally better than the value for the compositions of Example 27, possibly due to the hydrophilic tapioca material enabling better antiperspirant active release compared to the hydrophobically modified tapioca material of Example 27. The mean sweat value post treatment for antiperspirant compositions of comparative Example 36 was directionally worse than the value for the antiperspirant composition of Example 26. This may be due to reduced antiperspirant active substantivity resulting from use of the volatile silicone fluid in the antiperspirant composition of comparative Example 36 compared to use of a non-volatile silicone fluid in the antiperspirant compositions of Example 26.

Examples 37 to 48 describe some non-limiting examples of combinations of antiperspirant compositions and propellants. The concentration of particulates by weight of the total fill of materials (e.g., antiperspirant composition plus propellant) is also set forth in Examples 37 to 48.

|  | EX 37 | EX 38 | EX 39 | EX 40 | EX 41 | EX 42 |
|---|---|---|---|---|---|---|
| Propellant A46 | 85.00 | 85.00 | 85.00 | 85.00 | 85.00 | 85.00 |
| Dimethicone 50 cst[2] | 5.03 | 4.58 | 3.68 | 5.43 | 5.26 | 5.03 |
| Aluminum Chlorohydrate[1] | 4.20 | 4.20 | 4.20 | 4.20 | 4.20 | 4.20 |
| Tapioca Starch | 1.80 | 1.80 | 1.80 | 1.80 | 1.80 | 1.80 |
| C12-C15 Alkyl Benzoate | 1.02 | 1.02 | 1.02 | 1.02 | 1.02 | 1.02 |
| Fragrance | 1.05 | 1.05 | 1.05 | 1.05 | 1.05 | 1.05 |
| PMX 1503 dimethicone and Dimethiconol[6] | 0.45 | 0.90 | 1.80 |  |  |  |
| Dimethicone 330M cps |  |  |  | 0.05 | 0.22 | 0.45 |
| BCDs | 0.45 | 0.45 | 0.45 | 0.45 | 0.45 | 0.45 |
| Disteardimonium Hectorite | 0.45 | 0.45 | 0.45 | 0.45 | 0.45 | 0.45 |
| Isopropyl Myristate | 0.41 | 0.41 | 0.41 | 0.41 | 0.41 | 0.41 |
| Triethyl Citrate | 0.14 | 0.14 | 0.14 | 0.14 | 0.14 | 0.14 |
| Total | 100.00 | 100.00 | 100.00 | 100.00 | 100.00 | 100.00 |

|  | EX 43 | EX 44 | EX 45 | EX 46 | EX 47 | EX 48 |
|---|---|---|---|---|---|---|
| Propellant A46 | 80.00 | 85.00 | 90.00 | 90.00 | 85.00 | 75.00 |
| Dimethicone 50 cst[2] | 5.94 | 4.46 | 3.35 | 2.45 | 5.03 | 8.13 |
| Aluminum Chlorohydrate[1] | 6.67 | 5.00 | 2.80 | 2.80 | 4.20 | 7.25 |
| Dry Flo Pure | 1.40 | 1.05 | 1.20 | 1.20 | 1.80 | 3.00 |
| C12-C15 Alkyl Benzoate | 1.22 | 0.92 | 0.68 | 0.68 | 1.02 | 1.70 |
| Fragrance | 1.60 | 1.20 | 0.70 | 0.70 | 1.05 | 1.75 |
| PMX 1503 dimethicone and Dimethiconol[6] | 0.60 | 0.45 | 0.30 | 1.20 | 0.45 | 0.75 |
| BCDs | 0.60 | 0.45 | 0.30 | 0.30 | 0.45 | 0.75 |
| Disteardimonium Hectorite | 0.80 | 0.60 | 0.30 | 0.30 | 0.45 | 0.75 |
| Isopropyl Myristate | 0.90 | 0.67 | 0.27 | 0.27 | 0.41 | 0.68 |
| Triethyl Citrate | 0.27 | 0.20 | 0.10 | 0.10 | 0.14 | 0.23 |
| Total | 100.00 | 100.00 | 100.00 | 100.00 | 100.00 | 100.00 |

Examples 37 to 48 are made generally according to FIG. 13. The first step comprises optionally mixing a first portion of the non-volatile silicone fluid (e.g., 10% to 30% of the total concentration of the final antiperspirant composition) with the clay material and the liquid activation enhancer. The second step comprises adding a clay activator to the mixture of the first step. This is followed by adding a second portion of the non-volatile silicone fluid in a third step, after which the particulates are added in a fourth step to form a first composition. The first composition is filled into a reservoir of the spray device, after which the liquid fragrance material is added to the reservoir of the spray device to form the antiperspirant composition. The valve assembly is then attached to the spray device after which the propellant is added to the reservoir through the valve assembly. Significant mixing of the liquid fragrance material and the first composition is not believed to occur until the addition of the propellant, which beneficially dilutes both the liquid fragrance material and the first composition thereby minimizing regions of high liquid fragrance material concentration that may negatively impact the desired bulking benefit of the clay material. Then the actuator is attached to the valve assembly.

Figure 27:
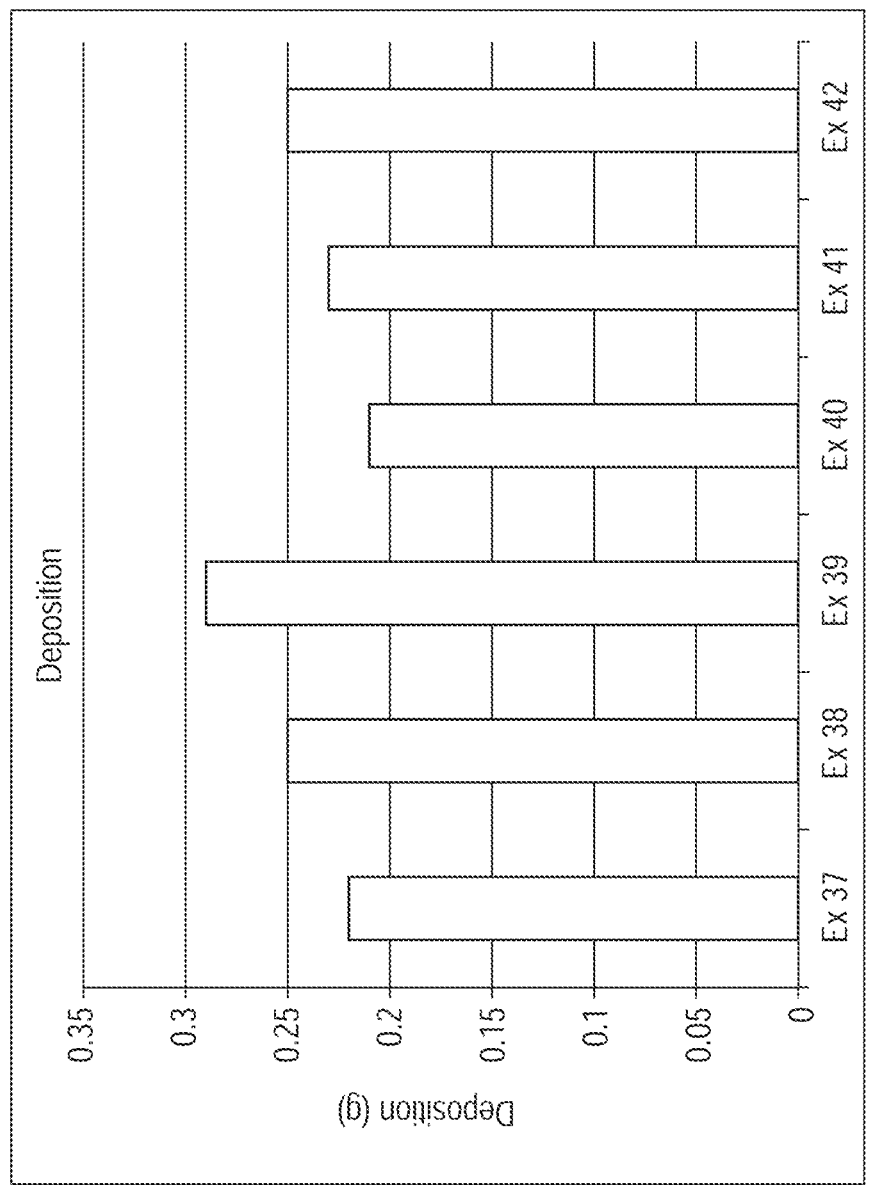
FIG. 27 is a bar graph illustrating formulations with various gum concentrations v. percent deposition of antiperspirant composition in grams.

FIG. 27 is a bar graph illustrating formulations with various silicone gum concentrations v. percent deposition of antiperspirant composition in grams. The actual level of silicone gum (PMX 1503 dimethicone and Dimethiconol and Dimethicone 330M cps) in finished product in examples 37 to 42 are: EX 37 (0.054%); Ex 38 (0.108%); EX 39 (0.216%); EX 40 (0.05%); EX 41 (0.22%) and EX 42 (0.45%). The deposition in grams are: EX 37 (0.22 grams); Ex 38 (0.25 grams); EX 39 (0.29 grams); EX 40 (0.21 grams); EX 41 (0.23 grams) and EX 42 (0.25 grams). The bar graph in FIG. 27 demonstrates the increase in the deposition in grams of antiperspirant composition with increasing level of gum in finished product, and also demonstrates that a higher molecular weight gum, PMX 1503, is more efficient than a lower molecular weight gum, Dimethicone 330M cps. The amount of deposition is measured according to the methods in section "Antiperspirant Active Deposition Efficiency, Amount Dispensed, and Amount Deposited".

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm". All numeric values (e.g., dimensions, flow rates, pressures, concentrations, etc.) recited herein may be modified by the term "about", even if not expressly so stated with the numeric value.

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A hand held spray device, comprising:
   a body comprising a reservoir to house a total fill of material;
   an actuator comprising an actuator exit orifice;
   a valve in fluid communication with the actuator exit orifice and the reservoir;
   a propellant stored in the reservoir;
   an antiperspirant composition stored in the reservoir, the antiperspirant composition comprising a non-volatile silicone fluid having a concentration from about 30% to about 50% by weight of the antiperspirant composition, an antiperspirant active, an organoclay material and at least one liquid having a concentration of about 2% to about 30% by weight of the antiperspirant composition and having a Hansen Solubility Parameter for Hydrogen Bonding, $\delta_h$, between about 2 and about 6 and a light transmittance value greater than 90% ; wherein the at least one liquid comprises a combination of a first liquid selected from the group consisting of ethyl stearate, propyl stearate, butyl stearate, ethyl myristate, isopropyl myristate, ethyl palmitate, isopropyl palmitate, butyl palmitate and combinations thereof and a second liquid that is selected from the group consisting of stearyl benzoate, palmityl benzoate, C12-15 alkyl benzoate, and combinations thereof,
   wherein the non-volatile silicone fluid comprises an average viscosity from about $3 \times 10^{-6}$ m$^2$/s to about $350 \times 10^{-6}$ m$^2$/s; and
   wherein the antiperspirant composition further comprises a silicone gum having a concentration of 0.3% to 1.2% by weight of the antiperspirant composition; and
   wherein the antiperspirant composition further comprises a liquid fragrance material having a concentration from about 4% to about 10% by weight of the antiperspirant composition; and
   wherein the viscosity of the antiperspirant composition is from about 2,000 centipoise to about 50,000 centipoise.

2. The method according to claim 1, wherein the first liquid is selected from the group consisting of isopropyl myristate, isopropyl palmitate, butyl stearate, and combinations thereof, and the second liquid is C12-15 alkyl benzoate.

3. The hand held spray device according to claim 1, wherein the organoclay material is selected from the group consisting of stearalkonium bentonite, disteardimonium hectorite, quaternium 90-bentonite, and combinations thereof.

4. The hand held spray device according to claim 1, further comprising a clay activator wherein the clay activator is selected from the group consisting of propylene carbonate, triethyl citrate, methanol, ethanol, acetone, water and combinations thereof.

5. The hand held spray device according to claim 1, wherein the organoclay material has a concentration from about 1% to about 8% by weight of the antiperspirant composition.

6. The hand held spray device according to claim 1, wherein the non-volatile silicone fluid has a viscosity at the time of making from about $5 \times 10^{-6}$ m$^2$/s to about $350 \times 10^{-6}$ m$^2$/s.

7. The hand held spray device according to claim 6, wherein the non-volatile silicone fluid has a viscosity at the time of making from about $5 \times 10^{-6}$ m$^2$/s to about $100 \times 10^{-6}$ m$^2$/s.

8. The hand held spray device according to claim 1, wherein the non-volatile silicone fluid comprises a polydimethylsiloxane fluid having an average molecular weight from about 500 to about 13,700 at the time of making.

9. The hand held spay device according to claim 8, wherein the polydimethylsiloxane fluid has the following formula (II):

$$M\text{-}D_X\text{-}M$$

wherein M is $(CH_3)_3SiO$, D is $((CH_3)_2SiO)$ and X is from about 4 to about 183.

10. The hand held spray device according to claim 1, wherein the antiperspirant composition is substantially free of a volatile silicone fluid.

11. The hand held spray device according to claim 1, wherein the second liquid is C12-15 alkyl benzoate and the non-volatile silicone fluid comprises a polymethylsiloxane fluid.

12. The hand held spray device according to claim 1, wherein the antiperspirant composition is substantially free of mineral oil, isohexadecane, PPG-14 butyl ether and octyldodecanol.

13. The hand held spray device according to claim 1, wherein the non-volatile silicone fluid comprises a polymethylsiloxane, wherein the first liquid is isopropyl myristate having a concentration from about 2% to about 10% by weight of the antiperspirant composition and wherein the liquid fragrance material has a concentration from about 4% to about 6% by weight of the antiperspirant composition.

14. A hand held spray device, comprising:
a body comprising a reservoir to house a total fill of materials;
an actuator comprising an actuator exit orifice;
a valve in fluid communication with the actuator exit orifice and the reservoir;
a propellant stored in the reservoir;
an antiperspirant composition stored in the reservoir, the antiperspirant composition comprising a non-volatile silicone fluid having a concentration from about 30% to about 50% by weight of the antiperspirant composition, an antiperspirant active, an organoclay material having a concentration from 1% to about 8% by weight of the antiperspirant composition, at least one liquid having a concentration of about 2% to about 30% by weight of the antiperspirant composition; and having a Hansen Solubility Parameter for Hydrogen Bonding, $\delta_h$, between about 2 and about 6 and a light transmittance value greater than 90% in the non-volatile silicone fluid, wherein the at least one liquid comprises a combination of a first liquid selected from the group consisting of ethyl stearate, propyl stearate, butyl stearate, ethyl myristate, isopropyl myristate, ethyl palmitate, isopropyl palmitate, butyl palmitate and combinations thereof and a second liquid that is selected from the group consisting of stearyl benzoate, palmityl benzoate and C12-15 alkyl benzoate, and combinations thereof, and a liquid fragrance material having a concentration from about 4% to about 10% by weight of the antiperspirant composition;
wherein the non-volatile silicone fluid comprises an average viscosity from about $3 \times 10^{-6}$ m$^2$/s to about $350 \times 10^{-6}$ m$^2$/s; and wherein the antiperspirant composition further comprises a silicone gum having a concentration of 0.3% to 1.2% by weight of the antiperspirant composition; and
wherein the viscosity of the antiperspirant composition is from about 2,000 centipoise to about 50,000 centipoise.

15. The hand held spray device according to claim 14, wherein the concentration of the liquid fragrance material by weight of the antiperspirant composition is greater than the concentration of the organoclay material.

16. The method according to claim 14, wherein the first liquid is selected from the group consisting of isopropyl myristate, isopropyl palmitate, butyl stearate, and combinations thereof, and the second liquid is C12-15 alkyl benzoate.

17. The hand held spray device according to claim 14, wherein the organoclay material is selected from the group consisting of stearalkonium bentonite, disteardimonium hectorite, quaternium 90-bentonite, and combinations thereof.

18. The hand held spray device according to claim 14, further comprising a clay activator wherein the clay activator is selected from the group consisting of propylene carbonate, triethyl citrate, methanol, ethanol, acetone, water and combinations thereof.

19. The hand held spray device of claim 18, wherein the concentration of the liquid fragrance material by weight of the antiperspirant composition is greater than the concentration of the clay activator.

20. The hand held spray device according to claim 14, wherein the non-volatile silicone fluid has a viscosity at the time of making from about $5 \times 10^{-6}$ m$^2$/s to about $350 \times 10^{-6}$ m$^2$/s.

21. The hand held spray device according to claim 20, wherein the non-volatile silicone fluid has a viscosity at the time of making from about $5 \times 10^{-6}$ m$^2$/s to about $100 \times 10^{-6}$ m$^2$/s.

22. The hand held spray device according to claim 14, wherein the non-volatile silicone fluid comprises a polydimethylsiloxane fluid having an average molecular weight from about 500 to about 13,700 at the time of making.

23. The hand held spray device according to claim 22, wherein the polydimethylsiloxane fluid has the following formula (II):

$$M\text{-}D_X\text{-}M$$

wherein M is $(CH_3)_3SiO$, D is $((CH_3)_2SiO)$ and X is from about 4 to about 183.

24. The hand held spray device according to claim 14, wherein the antiperspirant composition is substantially free of a volatile silicone fluid.

25. The hand held spray device according to claim 14, wherein the second liquid is C12-15 alkyl benzoate and the non-volatile silicone fluid comprises a polymethylsiloxane fluid.

26. The hand held spray device according to claim 14, wherein the antiperspirant composition is substantially free of mineral oil, isohexadecane, PPG-14 butyl ether and octyldodecanol.

27. The hand held spray device according to claim 14, wherein the non-volatile silicone fluid comprises a polymethylsiloxane having a viscosity about $50 \times 10^{-6}$ m$^2$/s, wherein the first liquid is isopropyl myristate having a concentration from about 2% to about 10% by weight of the antiperspirant composition and wherein the liquid fragrance material has a concentration from about 4% to about 6% by weight of the antiperspirant composition.

28. The hand held spray device according to claim 14, wherein the non-volatile silicone comprises polydimethylsiloxane fluid having a viscosity less than or equal to about 20 centistokes, the second liquid is C12-15 alkyl benzoate; and wherein the antiperspirant composition is substantially or completely free of a clay activator selected from the group consisting of propylene carbonate, triethyl citrate, methanol, ethanol, acetone and mixtures thereof.

29. The hand held spray device according to claim 28, wherein the C12-15 alkyl benzoate has a concentration from 2% to about 30% by weight of the antiperspirant composition.

30. The device of claim 14, wherein the non-volatile silicone fluid comprises an average viscosity from about $50 \times 10^{-6}$ m$^2$/s to about $350 \times 10^{-6}$ m$^2$/s.

31. The device of claim 14, wherein the non-volatile silicone fluid comprises an average viscosity from about $100 \times 10^{-6}$ m$^2$/s to about $350 \times 10^{-6}$ m$^2$/s.

32. The device of claim 31, wherein the first liquid is isopropyl myristate.

* * * * *